US008183005B1

(12) United States Patent  (10) Patent No.: US 8,183,005 B1
Sudo et al.  (45) Date of Patent: May 22, 2012

(54) PHARMACEUTICAL AGENTS FOR TREATING HCV INFECTIONS

(75) Inventors: Masayuki Sudo, Kanagawa (JP); Hiroshi Sakamoto, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 1159 days.

(21) Appl. No.: 11/659,779

(22) PCT Filed: Aug. 11, 2005

(86) PCT No.: PCT/JP2005/014767
§ 371 (c)(1), (2), (4) Date: Aug. 9, 2007

(87) PCT Pub. No.: WO2006/016657
PCT Pub. Date: Feb. 16, 2006

(30) Foreign Application Priority Data

Aug. 11, 2004 (JP) .................................. 2004-234900

(51) Int. Cl.
*C12Q 1/48* (2006.01)
*C12Q 1/00* (2006.01)
(52) U.S. Cl. .............. 435/15; 435/4; 435/7.91; 435/193
(58) Field of Classification Search ............. 435/4, 7.91, 435/15, 193
See application file for complete search history.

(56) References Cited

U.S. PATENT DOCUMENTS

| | | | |
|---|---|---|---|
| 3,000,910 A | 9/1961 | Birkenmeyer et al. | |
| 3,210,386 A | 10/1965 | Birkenmeyer et al. | |
| 3,389,051 A | 6/1968 | Fred | |
| 3,928,572 A * | 12/1975 | Kluepfel et al. | 424/122 |
| 5,518,879 A * | 5/1996 | Merrill et al. | 435/4 |
| 5,863,716 A * | 1/1999 | Haldar et al. | 435/4 |
| 5,976,781 A * | 11/1999 | Haldar et al. | 435/4 |
| 6,303,350 B1 | 10/2001 | Takesako et al. | |
| 7,217,793 B2 * | 5/2007 | Kobayashi et al. | 530/350 |
| 7,378,446 B2 | 5/2008 | Sudoh et al. | |
| 7,776,918 B2 | 8/2010 | Aoki et al. | |
| 2002/0127203 A1 | 9/2002 | Albrecht | |
| 2006/0128617 A1 | 6/2006 | Kohara et al. | |
| 2006/0194870 A1 | 8/2006 | Sudoh et al. | |
| 2006/0217434 A1 | 9/2006 | Aoki et al. | |
| 2006/0264389 A1 | 11/2006 | Bhat et al. | |
| 2007/0087984 A1 * | 4/2007 | Hu et al. | 514/44 |
| 2008/0027088 A1 * | 1/2008 | Homan et al. | 514/275 |
| 2009/0022687 A1 | 1/2009 | Matsumoto et al. | |

FOREIGN PATENT DOCUMENTS

| | | |
|---|---|---|
| CA | 2 652 333 | 11/2007 |
| EP | 1 593 378 | 11/2005 |
| EP | 1 795 206 | 6/2007 |
| JP | 07-173123 A | 7/1995 |
| JP | 2004-511513 | 4/2004 |
| JP | 2005-533108 | 11/2005 |
| JP | 2005-533824 | 11/2005 |
| JP | 2006-077004 | 3/2006 |
| JP | 3921227 | 5/2007 |
| WO | WO 94/18157 | 8/1994 |
| WO | WO 98/56755 | 12/1998 |
| WO | WO 00/37097 | 6/2000 |
| WO | WO 0180903 A1 * | 11/2001 |
| WO | WO 02/32414 | 4/2002 |
| WO | WO 02/48325 | 6/2002 |
| WO | WO 2004/002422 | 1/2004 |
| WO | WO 2004/007512 | 1/2004 |
| WO | WO 2004/071503 | 8/2004 |
| WO | WO 2004/078127 | 9/2004 |
| WO | WO 2004/078974 | 9/2004 |
| WO | WO 2005/005372 | 1/2005 |
| WO | 2005019268 A1 | 3/2005 |
| WO | WO 2005/062949 | 7/2005 |
| WO | WO 2006/016657 | 2/2006 |
| WO | WO 2006/123724 | 11/2006 |
| WO | WO 2007/132882 | 11/2007 |

OTHER PUBLICATIONS

Futerman et al. Trends in Cell Biology (Jun. 2005) 15(6): 312-318.*
Balsano, C. Mini-Reviews in Medicinal Chemistry (2008) 8: 307-318.*
Bordier et al., "A Prenylation Inhibitor Prevents Production of Infectious Hepatitis Delta Virus Particles," *J. Virol.*, 76:10465-10472 (2002).
Guillas et al., "Human Homologues of LAG1 Reconstitute Acyl-CoA-dependent Ceramide Synthesis in Yeast," *J. Biol. Chem.*, 278:37083-37091 (2003).
Leu et al., "Anti-HCV activities of selective polyunsaturated fatty acids," *Biochem. Biophys. Res. Commun.*, 318:275-280 (2004).
Lohmann et al., "Replication of Subgenomic Hepatitis C Virus RNAs in a Hepatoma Cell Line," *Science*, 285:110-113 (1999).
Lucero et al., "Lipid rafts-protein association and the regulation of protein activity," *Arch. Biochem. Biophys.*, 426:208-224 (2004).
Mandala et al., "Viridiofungins, Novel Inhibitors of Sphingolipid Synthesis," *J. Antibiot.* (Tokyo), 50:339-343 (1997).
Miyake et al., "Serine palmitoyltransferase is the primary target of a sphingosine-like immunosuppressant, ISP-1/myriocin," *Biochem. Biophys. Res. Commun.*, 211:396-403 (1995).

(Continued)

*Primary Examiner* — Susan Hanley
(74) *Attorney, Agent, or Firm* — Fish & Richardson P.C.

(57) ABSTRACT

The present inventors examined the inhibitory activity against HCV replicon of myriocin, fumonisin B1, and ceramide trafficking inhibitor HPA-12, which are compounds derived from microorganisms such as those of the genus *Aureobasidium*, and found that these compounds have the effect of inhibiting the replication of HCV replicon RNAs or inhibiting the expression of HCV proteins. The present inventors further performed serine palmitoyltransferase knockdown experiments using siRNAs, and results showed that HCV replicon activity and HCV protein expression were significantly inhibited in cells with suppressed LCB1 expression. Thus, sphingolipid biosynthesis was found to be involved in HCV infection. This showed that HCV infection can be treated or prevented by inhibiting enzyme activities involved in the process of sphingolipid biosynthesis by adding compounds or knocking down a gene.

29 Claims, 17 Drawing Sheets

OTHER PUBLICATIONS

Onishi et al., "Antimicrobial Activity of Viridiofungins," *J. Antibiot.* (Tokyo), 50:334-338 (1997).

Riebeling et al., "Two Mammalian Longevity Assurance Gene (LAG1) Family Members, *trh1* and *trh4*, Regulate Dihydroceramide Synthesis Using Different Fatty Acyl-CoA Donors," *J. Biol. Chem.*, 278:43452-43459 (2003).

Simons et al., "Functional rafts in cell membranes," *Nature*, 387:569-572 (1997).

Takeda et al., "Influenza virus hemagglutinin concentrates in lipid raft microdomains for efficient viral fusion," *Proc. Natl. Acad. Sci. USA*, 100:14610-14617.(2003).

Worgall et al., "Ceramide Synthesis Correlates with the Post-transcriptional Regulation of the Sterol-Regulatory Element-Binding Protein," *Arterioscler. Thromb. Vasc. Biol.*, 24:943-948 (2004).

Yamaoka et al., "Expression Cloning of a Human cDNA Restoring Sphingomyelin Synthesis and Cell Growth in Sphingomyelin Synthase-defective Lymphoid Cells," *J. Biol. Chem.*, 279:18688-18693 (2004).

Zweerink et al., "Characterization of a Novel, Potent, and Specific Inhibitor of Serine Palmitoyltransferase," *J. Biol. Chem.*, 267:25032-25038 (1992).

Aizaki et al., "Characterization of the hepatitis C virus RNA replication complex associated with lipid rafts," *Virology*, 324:450-461 (2004).

Fujita et al., "Fungal Metabolites. Part 11. A Potent Immunosuppressive Activity Found in *Isaria sinclairii* Metabolite," *J. Antibot.* (Tokyo), 47:208-215 (1994).

Gao et al., "Interactions between Viral Nonstructural Proteins and Host Protein hVAP-33 Mediate the Formation of Hepatitis C Virus RNA Replication Complex on Lipid Raft," *J Virol.*, 78:3480-88 (2004).

Glue et al., "A Dose-Ranging Study Pegylated Interferon Alfa-2b and Ribavirin in Chronic Hepatitis C," *Hepatol.*, 32:647-653 (2000).

Ni and Wagman, "Progress and development of small molecule HCV antivirals," *Curr. Opin. Drug Discov. Devel.*, 7(4):446-459 (2004).

Reddy et al., "Efficacy and Safety of Pegylated (40-kd) Interferon α-2a Compared With Interferon α-2a in Noncirrhotic Patients With Chronic Hepatitis C," *Hepatol.*, 33:433-438 (2001).

Rosenberg, "Recent Advances in the Molecular Biology of Hepatitis C Virus," *J. Mol. Biol.*, 313:451-464 (2001).

Sakamoto et al., "Host sphingolipid biosynthesis as a target for hepatitis C virus therapy," *Nat. Chem. Biol.*, 1(6):333-337 (2005).

Umehara et al., "Serine palmitoyltransferase inhibitor suppresses HCV replication in a mouse model," *Biochem. Biophys. Res. Commun.*, 346(1):67-73 (2006).

International Preliminary Report on Patentability for App. Ser. No. PCT/JP2007/060016, dated Dec. 10, 2008, 8 pages.

Japanese Patent Office, International Search Report for App. Ser. No. PCT/JP2007/060016, mailed Jun. 19, 2007, 2 pages.

International Preliminary Report on Patentability for App. Ser. No. PCT/JP2005/014767, dated Feb. 20, 2007, 8 pages.

Japanese Patent Office, International Search Report for App. Ser. No. PCT/JP2005/014767, mailed Nov. 15, 2005, 3 pages.

European Search Report for App. Ser. No. EP 05 77 0415, dated Jun. 16, 2009 (3 pages).

Bae et al., "Cholesterol biosynthesis from lanosterol: development of a novel assay method and characterization of rat liver microsomal lanosterol delta 24-reductase," Biochem J., 326(Pt 2):609-16 (1997).

Di Stasi et al., "DHCR24 gene expression is upregulated in melanoma metastases and associated to resistance to oxidative stress-induced apoptosis," Int. J. Cancer., 115(2):224-30 (2005).

Mahfoud et al., "Identification of a common sphingolipid-binding domain in Alzheimer, prion, and HIV-1 proteins," J. Biol. Chem., 277(13):11292-6 (2002).

Nehete et al., "A post-CD4-binding step involving interaction of the V3 region of viral gp120 with host cell surface glycosphingolipids is common to entry and infection by diverse HIV-1 strains," Antiviral Res., 56(3):233-51 (2002).

Sakamoto et al., "Identification of a novel small molecule hepatitis C virus replication inhibitor that targets host sphingolipid biosynthesis," Hepatology, 42(4)(Suppl. 1) 535A:863 (2005).

Shi et al., "Hepatitis C virus RNA replication occurs on a detergent-resistant membrane that cofractionates with caveolin-2," J. Virol., 77(7):4160-8 (2003).

Ye et al., "Disruption of hepatitis C virus RNA replication through inhibition of host protein geranylgeranylation," *Proc. Natl. Acad. Sci. U.S.A.*, 100(26):15865-70 (2003).

Choo et al., "Genetic organization and diversity of the hepatitis C virus," *Proc. Natl. Acad. Sci. U.S.A.*, 88(6):2451-5 (1991).

Fire et al., "Potent and specific genetic interference by double-stranded RNA in *Caenorhabditis elegans*," *Nature*, 391(6669):806-11 (1998).

Honda et al., "Stability of a stem-loop involving the initiator AUG controls the efficiency of internal initiation of translation on hepatitis C virus RNA," *RNA*, 2(10):955-68 (1996).

Honda et al., "A phylogenetically conserved stem-loop structure at the 5' border of the internal ribosome entry site of hepatitis C virus is required for cap-independent viral translation," *J Virol.*, 73(2):1165-74 (1999).

Ito et al., "The 3'-untranslated region of hepatitis C virus RNA enhances translation from an internal ribosomal entry site," *J. Virol.*, 72(11):8789-96 (1998).

Kamoshita et al., "Genetic analysis of internal ribosomal entry site on hepatitis C virus RNA: implication for involvement of the highly ordered structure and cell type-specific transacting factors," *Virology*, 233(1):9-18 (1997).

Kato et al., "Molecular cloning of the human hepatitis C virus genome from Japanese patients with non-A, non-B hepatitis," *Proc. Natl. Acad. Sci. U.S.A.*, 87(24):9524-8 (1990).

Mandala et al., "Isolation and characterization of novel inhibitors of sphingolipid synthesis: australifungin, viridiofungins, rustmicin, and khafrefungin," *Methods Enzymol.*, 311:335-348 (2000).

Miyakawa et al., "Classifying hepatitis B virus genotypes," *Intervirology*, 46:329-338 (2003).

Okamoto et al., "Nucleotide sequence of the genomic RNA of hepatitis C virus isolated from a human carrier: comparison with reported isolates for conserved and divergent regions," *J. Gen. Virol.*, 72(Pt 11):2697-704 (1991).

Okamoto et al., "Full-length sequence of a hepatitis C virus genome having poor homology to reported isolates: comparative study of four distinct genotypes," *Virology*, 188(1):331-41 (1992).

Orito et al., "A case-control study for clinical and molecular biological differences between hepatitis B viruses of genotypes B and C. Japan HBV Genotype Research Group," *Hepatology*, 33(1):218-223 (2001).

Ozasa et al., "Influence of genotypes and precore mutations on fulminant or chronic outcome of acute hepatitis B virus infection," *Hepatology*, 44(2):326-334 (2006).

Sasano et al., "Sequence analysis of the IRES-Loop III region of hepatitis C virus," *Genome Inf. Ser.*, 9:395-6 (1998).

Sugiyama et al., "Influence of hepatitis B virus genotypes on the intra- and extracellular expression of viral DNA and antigens," *Hepatology*, 44(4):915-924 (2006).

Takamizawa et al., "Structure and organization of the hepatitis C virus genome isolated from human carriers," *J. Virol.*, 65(3):1105-13 (1991).

Tsukiyama-Kohara et al., "Internal ribosome entry site within hepatitis C virus RNA," *J. Virol.*, 66(3):1476-83 (1992).

Watanabe et al., "Intracellular-diced dsRNA has enhanced efficacy for silencing HCV RNA and overcomes variation in the viral genotype," *Gene Ther.*, 13(11):883-92 (2006).

Watanabe et al., "Therapeutic application of RNA interference for hepatitis C virus," *Adv. Drug Deliv. Rev.*, 59(12):1263-76 (2007).

International Search Report for App. Ser. No. PCT/JP2009/061087, mailed Aug. 11, 2009, 3 pages.

USPTO Restriction Requirement in U.S. Appl. No. 12/301,001, dated Aug. 16, 2011, 7 pages.

International Preliminary Report on Patentability for App. Ser. No. PCT/JP2009/069934, dated Jul. 5, 2011, 10 pages.

International Search Report for App. Ser. No. PCT/JP2009/069934, dated Feb. 16, 2010, 5 pages.

Supplementary European Search Report for App. Ser. No. EP 07 74 3451, mailed Oct. 17, 2011, 10 pages.

\* cited by examiner

FIG. 7
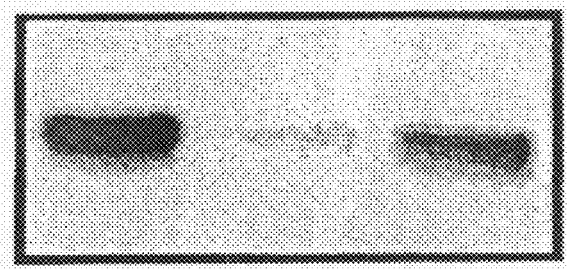
LCB1
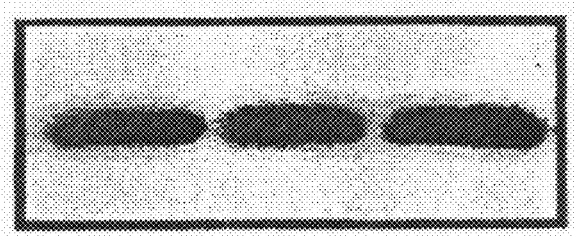
ACTIN

SEQUENCE LISTING

```
<160> NUMBER OF SEQ ID NOS: 11

<210> SEQ ID NO 1
<211> LENGTH: 21
<212> TYPE: DNA
<213> ORGANISM: Artificial Sequence
<220> FEATURE:
<223> OTHER INFORMATION: artificially synthesized primer sequence
<220> FEATURE:
<221> NAME/KEY: misc_feature
<222> LOCATION: (20)..(21)
<223> OTHER INFORMATION: synthetically generated DNA/RNA oligonucleotide

<400> SEQUENCE: 1
caucguuuca ggcccuccat t                                              21

<210> SEQ ID NO 2
<211> LENGTH: 21
<212> TYPE: DNA
<213> ORGANISM: Artificial Sequence
<220> FEATURE:
<223> OTHER INFORMATION: artificially synthesized primer sequence
<220> FEATURE:
<221> NAME/KEY: misc_feature
<222> LOCATION: (20)..(21)
<223> OTHER INFORMATION: synthetically generated DNA/RNA oligonucleotide

<400> SEQUENCE: 2
ugacauggcu gaccucgagt t                                              21

<210> SEQ ID NO 3
<211> LENGTH: 21
<212> TYPE: DNA
<213> ORGANISM: Artificial Sequence
<220> FEATURE:
<223> OTHER INFORMATION: artificially synthesized primer sequence
<220> FEATURE:
<221> NAME/KEY: misc_feature
<222> LOCATION: (20)..(21)
<223> OTHER INFORMATION: synthetically generated DNA/RNA oligonucleotide

<400> SEQUENCE: 3
ggacuuccag aagaacauct t                                              21

<210> SEQ ID NO 4
<211> LENGTH: 2742
<212> TYPE: DNA
<213> ORGANISM: Homo sapiens
<220> FEATURE:
```

<221> NAME/KEY: CDS
<222> LOCATION: (9)..(1550)

<400> SEQUENCE: 4

```
ggctaact atg gcg acc gcc acg gag cag tgg gtt ctg gtg gag atg gta      50
         Met Ala Thr Ala Thr Glu Gln Trp Val Leu Val Glu Met Val
         1               5                   10 cag gcg ctt tac gag gct cct gct tac cat ctt att ttg gaa ggg att      98
Gln Ala Leu Tyr Glu Ala Pro Ala Tyr His Leu Ile Leu Glu Gly Ile
15                  20                  25                  30 ctg atc ctc tgg ata atc aga ctt ctt ttc tct aag act tac aaa tta     146
Leu Ile Leu Trp Ile Ile Arg Leu Leu Phe Ser Lys Thr Tyr Lys Leu
                35                  40                  45 caa gaa cga tct gat ctt aca gtc aag gaa aaa gaa gaa ctg att gaa     194
Gln Glu Arg Ser Asp Leu Thr Val Lys Glu Lys Glu Glu Leu Ile Glu
            50                  55                  60 gag tgg caa cca gaa cct ctt gtt cct cct gtc cca aaa gac cat cct     242
Glu Trp Gln Pro Glu Pro Leu Val Pro Pro Val Pro Lys Asp His Pro
65                  70                  75 gct ctc aac tac aac atc gtt tca ggc cct cca agc cac aaa act gtg     290
Ala Leu Asn Tyr Asn Ile Val Ser Gly Pro Pro Ser His Lys Thr Val
        80                  85                  90 gtg aat gga aaa gaa tgt ata aac ttc gcc tca ttt aat ttt ctt gga     338
Val Asn Gly Lys Glu Cys Ile Asn Phe Ala Ser Phe Asn Phe Leu Gly
95                  100                 105                 110 ttg ttg gat aac cct agg gtt aag gca gca gct tta gca tct cta aag     386
Leu Leu Asp Asn Pro Arg Val Lys Ala Ala Ala Leu Ala Ser Leu Lys
                115                 120                 125 aag tat ggc gtg ggg act tgt gga ccc aga gga ttt tat ggc aca ttt     434
Lys Tyr Gly Val Gly Thr Cys Gly Pro Arg Gly Phe Tyr Gly Thr Phe
            130                 135                 140 gat gtt cat ttg gat ttg gaa gac cgc ctg gca aaa ttt atg aag aca     482
Asp Val His Leu Asp Leu Glu Asp Arg Leu Ala Lys Phe Met Lys Thr
145                 150                 155 gaa gaa gcc att ata tac tca tat gga ttt gcc acc ata gcc agt gct     530
Glu Glu Ala Ile Ile Tyr Ser Tyr Gly Phe Ala Thr Ile Ala Ser Ala
        160                 165                 170 att cct gct tac tct aaa aga ggg gac att gtt ttt gta gat aga gct     578
Ile Pro Ala Tyr Ser Lys Arg Gly Asp Ile Val Phe Val Asp Arg Ala
175                 180                 185                 190 gcc tgc ttt gct att cag aaa gga tta cag gca tcc cgt agt gac att     626
Ala Cys Phe Ala Ile Gln Lys Gly Leu Gln Ala Ser Arg Ser Asp Ile
                195                 200                 205 aag tta ttt aag cat aat gac atg gct gac ctc gag cga cta cta aaa     674
Lys Leu Phe Lys His Asn Asp Met Ala Asp Leu Glu Arg Leu Leu Lys
            210                 215                 220 gaa caa gag atc gaa gat caa aag aat cct cgc aag gct cgt gta act     722
Glu Gln Glu Ile Glu Asp Gln Lys Asn Pro Arg Lys Ala Arg Val Thr
225                 230                 235 cgg cgt ttc att gta gta gaa gga ttg tat atg aat act gga act att     770
Arg Arg Phe Ile Val Val Glu Gly Leu Tyr Met Asn Thr Gly Thr Ile
        240                 245                 250 tgt cct ctt cca gaa ttg gtt aag tta aaa tac aaa tac aaa gca aga     818
Cys Pro Leu Pro Glu Leu Val Lys Leu Lys Tyr Lys Tyr Lys Ala Arg
255                 260                 265                 270 atc ttc ctg gag gaa agc ctt tca ttt gga gtc cta gga gag cat ggc     866
Ile Phe Leu Glu Glu Ser Leu Ser Phe Gly Val Leu Gly Glu His Gly
                275                 280                 285 cga gga gtc act gaa cac tat gga atc aat att gat gat att gat ctt     914
Arg Gly Val Thr Glu His Tyr Gly Ile Asn Ile Asp Asp Ile Asp Leu
            290                 295                 300
```

```
atc agt gcc aac atg gag aat gca ctt gct tct att gga ggt ttc tgc      962
Ile Ser Ala Asn Met Glu Asn Ala Leu Ala Ser Ile Gly Gly Phe Cys
            305                 310                 315 tgt ggc agg tct ttt gta att gac cat cag cga ctt tcc ggc cag gga     1010
Cys Gly Arg Ser Phe Val Ile Asp His Gln Arg Leu Ser Gly Gln Gly
        320                 325                 330 tac tgc ttt tca gct tcg tta cct ccc ctg tta gct gct gca gca att     1058
Tyr Cys Phe Ser Ala Ser Leu Pro Pro Leu Leu Ala Ala Ala Ala Ile
335                 340                 345                 350 gag gcc ctc aac atc atg gaa gag aat cca ggt att ttt gca gtg ttg     1106
Glu Ala Leu Asn Ile Met Glu Glu Asn Pro Gly Ile Phe Ala Val Leu
                355                 360                 365 aag gaa aag tgc gga caa att cat aaa gct tta caa ggc att tct gga     1154
Lys Glu Lys Cys Gly Gln Ile His Lys Ala Leu Gln Gly Ile Ser Gly
            370                 375                 380 tta aaa gtg gtg ggg gag tcc ctt tct cca gcc ttt cac cta caa ctg     1202
Leu Lys Val Val Gly Glu Ser Leu Ser Pro Ala Phe His Leu Gln Leu
        385                 390                 395 gaa gag agc act ggg tct cgc gag caa gat gtc aga ctg ctt cag gaa     1250
Glu Glu Ser Thr Gly Ser Arg Glu Gln Asp Val Arg Leu Leu Gln Glu
400                 405                 410 att gta gat caa tgc atg aac aga agt att gca tta act cgg gcg cgc     1298
Ile Val Asp Gln Cys Met Asn Arg Ser Ile Ala Leu Thr Arg Ala Arg
415                 420                 425                 430 tac ttg gag aaa gaa gag aag tgt ctc cct cct ccc aga gga aga act     1346
Tyr Leu Glu Lys Glu Glu Lys Cys Leu Pro Pro Pro Arg Gly Arg Thr
                435                 440                 445 gga gag agc tgc gtc cac cat caa gga ggt agc cca ggc cgt cct gct     1394
Gly Glu Ser Cys Val His His Gln Gly Gly Ser Pro Gly Arg Pro Ala
            450                 455                 460 cta ggc aga gtc ccg gga cca tgg cct cct gcc aca caa cac gca gag     1442
Leu Gly Arg Val Pro Gly Pro Trp Pro Pro Ala Thr Gln His Ala Glu
        465                 470                 475 agg act caa gac tcc cgc tgg cca tgg agt ggc ctg aaa gag agc aag     1490
Arg Thr Gln Asp Ser Arg Trp Pro Trp Ser Gly Leu Lys Glu Ser Lys
480                 485                 490 aac atg tgg atc ttt gat agg att gtt acc aaa tgg tgt cag tat gga     1538
Asn Met Trp Ile Phe Asp Arg Ile Val Thr Lys Trp Cys Gln Tyr Gly
495                 500                 505                 510 cca att gtg tga ccatgagaag gatgcttatt ttttttaaaa agaaaacaca         1590
Pro Ile Val tctaaaagcc caggaactga ttttttttaag aggaaaacta atgacagtgt ataactgatg  1650
tttaaattgt gcatttagta ctatttaaat gttttcttat actagtattt tatattcttt   1710
tgttgtcgtt taaaactgga gcttcagtgt ctcttccctc cctctaatag taatggttca   1770
gtaagcactc cttaactcct tagtatttca tagaaaaatg actgcaacat taaagctaag   1830
aggaacactt caacatatgt ggtacaaatt tatattgaag atctaaataa accacgtatt   1890
ttccagtctt cgttgtgtga agctaaatgg tggctaaaag gaacactttt tgtgtgatta   1950
ttataaactt tgcattgtat ttgaatctta gaacttttgt acacactaaa tattgatgtc   2010
acaccatttc taatctgagc atccttagcc agagaatatt cattatactt cctaagtgag   2070
caataattta aatcagaagc tatttttattt taatgtaatt aacctttctt tacatttctt   2130
atgtgttcac ctctaatctg ttttaggaag agagttggtt attatgttga tcccataata   2190
taaatcatat cctttatatt ttagaatatc tcaaatgtat tccttttttg tatggtgggt   2250
ttgcctaggg acgtgtaact acaggctttt actaagccaa ggaaaagag aatttttctt    2310
```

-continued

```
ttcatcttac aaattccaga tatctacaaa agatgtgaaa gcactaaaaa taccatttt     2370 aagcagtact ttacctgttt tttctttagc aaaccaggtt atgtggtgta aaggtttgtt     2430
atacgtgcca caatatagca tataaatatt atgccatcat tccttctctt gttaaaggta     2490
gaagaataaa attgtgattt ttataacctg tgcttattac tcaaatggtc ttcaacatct     2550
ttttaaacaa cacatacttt ttgaatgttc agtttctatt ttgcttgagg tattttgtac     2610
atatgtgcct tgtgattgct gctgctttaa aggataaagt actctttggg ggatgagtct     2670
ggtttgtttt gttttatttt ttaatgaaat aaacctatat tcctgattat tagtccaaaa     2730
aaaaaaaaaa aa                                                        2742

<210> SEQ ID NO 5
<211> LENGTH: 513
<212> TYPE: PRT
<213> ORGANISM: Homo sapiens

<400> SEQUENCE: 5

Met Ala Thr Ala Thr Glu Gln Trp Val Leu Val Glu Met Val Gln Ala
1               5                   10                  15

Leu Tyr Glu Ala Pro Ala Tyr His Leu Ile Leu Glu Gly Ile Leu Ile
            20                  25                  30

Leu Trp Ile Ile Arg Leu Leu Phe Ser Lys Thr Tyr Lys Leu Gln Glu
        35                  40                  45

Arg Ser Asp Leu Thr Val Lys Glu Lys Glu Glu Leu Ile Glu Glu Trp
    50                  55                  60

Gln Pro Glu Pro Leu Val Pro Pro Val Pro Lys Asp His Pro Ala Leu
65                  70                  75                  80

Asn Tyr Asn Ile Val Ser Gly Pro Pro Ser His Lys Thr Val Val Asn
                85                  90                  95

Gly Lys Glu Cys Ile Asn Phe Ala Ser Phe Asn Phe Leu Gly Leu Leu
            100                 105                 110

Asp Asn Pro Arg Val Lys Ala Ala Ala Leu Ala Ser Leu Lys Lys Tyr
        115                 120                 125

Gly Val Gly Thr Cys Gly Pro Arg Gly Phe Tyr Gly Thr Phe Asp Val
    130                 135                 140

His Leu Asp Leu Glu Asp Arg Leu Ala Lys Phe Met Lys Thr Glu Glu
145                 150                 155                 160

Ala Ile Ile Tyr Ser Tyr Gly Phe Ala Thr Ile Ala Ser Ala Ile Pro
                165                 170                 175

Ala Tyr Ser Lys Arg Gly Asp Ile Val Phe Val Asp Arg Ala Ala Cys
            180                 185                 190

Phe Ala Ile Gln Lys Gly Leu Gln Ala Ser Arg Ser Asp Ile Lys Leu
        195                 200                 205

Phe Lys His Asn Asp Met Ala Asp Leu Glu Arg Leu Leu Lys Glu Gln
    210                 215                 220

Glu Ile Glu Asp Gln Lys Asn Pro Arg Lys Ala Arg Val Thr Arg Arg
225                 230                 235                 240

Phe Ile Val Val Glu Gly Leu Tyr Met Asn Thr Gly Thr Ile Cys Pro
                245                 250                 255

Leu Pro Glu Leu Val Lys Leu Lys Tyr Lys Tyr Lys Ala Arg Ile Phe
            260                 265                 270

Leu Glu Glu Ser Leu Ser Phe Gly Val Leu Gly Glu His Gly Arg Gly
        275                 280                 285

Val Thr Glu His Tyr Gly Ile Asn Ile Asp Asp Ile Asp Leu Ile Ser
    290                 295                 300
```

```
Ala Asn Met Glu Asn Ala Leu Ala Ser Ile Gly Gly Phe Cys Cys Gly
305                 310                 315                 320

Arg Ser Phe Val Ile Asp His Gln Arg Leu Ser Gly Gln Gly Tyr Cys
            325                 330                 335

Phe Ser Ala Ser Leu Pro Pro Leu Ala Ala Ala Ile Glu Ala
            340                 345                 350

Leu Asn Ile Met Glu Glu Asn Pro Gly Ile Phe Ala Val Leu Lys Glu
        355                 360                 365

Lys Cys Gly Gln Ile His Lys Ala Leu Gln Gly Ile Ser Gly Leu Lys
370                 375                 380

Val Val Gly Glu Ser Leu Ser Pro Ala Phe His Leu Gln Leu Glu Glu
385                 390                 395                 400

Ser Thr Gly Ser Arg Glu Gln Asp Val Arg Leu Leu Gln Glu Ile Val
            405                 410                 415

Asp Gln Cys Met Asn Arg Ser Ile Ala Leu Thr Arg Ala Arg Tyr Leu
            420                 425                 430

Glu Lys Glu Glu Lys Cys Leu Pro Pro Arg Gly Arg Thr Gly Glu
        435                 440                 445

Ser Cys Val His His Gln Gly Gly Ser Pro Gly Arg Pro Ala Leu Gly
        450                 455                 460

Arg Val Pro Gly Pro Trp Pro Pro Ala Thr Gln His Ala Glu Arg Thr
465                 470                 475                 480

Gln Asp Ser Arg Trp Pro Trp Ser Gly Leu Lys Glu Ser Lys Asn Met
            485                 490                 495

Trp Ile Phe Asp Arg Ile Val Thr Lys Trp Cys Gln Tyr Gly Pro Ile
                500                 505                 510

Val

<210> SEQ ID NO 6
<211> LENGTH: 7250
<212> TYPE: DNA
<213> ORGANISM: Homo sapiens
<220> FEATURE:
<221> NAME/KEY: CDS
<222> LOCATION: (189)..(1877)

<400> SEQUENCE: 6
ccttggccga gaccggtcct ctgcggagag ggccccgccc tctgtgaagg cccgcccggg      60
aattggcggc ggcgctgcag ccatttccgg tttcggggag gtgggtgggg tgcggagcgg     120
gacttggagc agccgccgcc gctgccaccg cctacagagc ctgccttgcg cctggtgctg     180 ccaggaag atg cgg ccg gag ccc gga ggc tgc tgc tgc cgc cgc acg gtg     230
         Met Arg Pro Glu Pro Gly Gly Cys Cys Cys Arg Arg Thr Val
         1               5                   10 cgg gcg aat ggc tgc gtg gcg aac ggg gaa gta cgg aac ggg tac gtg     278
Arg Ala Asn Gly Cys Val Ala Asn Gly Glu Val Arg Asn Gly Tyr Val
15                  20                  25                  30 agg agc agc gct gca gcc gca gcc gca gcc gcc gcc ggc cag atc cat     326
Arg Ser Ser Ala Ala Ala Ala Ala Ala Ala Ala Ala Gly Gln Ile His
                35                  40                  45 cat gtt aca caa aat gga gga cta tat aaa aga ccg ttt aat gaa gct     374
His Val Thr Gln Asn Gly Gly Leu Tyr Lys Arg Pro Phe Asn Glu Ala
        50                  55                  60 ttt gaa gaa aca cca atg ctg gtt gct gtg ctc acg tat gtg ggg tat     422
Phe Glu Glu Thr Pro Met Leu Val Ala Val Leu Thr Tyr Val Gly Tyr
    65                  70                  75 ggc gta ctc acc ctc ttt gga tat ctt cga gat ttc ttg agg tat tgg     470
```

```
Gly Val Leu Thr Leu Phe Gly Tyr Leu Arg Asp Phe Leu Arg Tyr Trp
         80                  85                  90 aga att gaa aag tgt cac cat gca aca gaa aga gaa gaa caa aag gac    518
Arg Ile Glu Lys Cys His His Ala Thr Glu Arg Glu Glu Gln Lys Asp
 95                 100                 105                 110 ttt gtg tca ttg tat caa gat ttt gaa aac ttt tat aca agg aat ctg    566
Phe Val Ser Leu Tyr Gln Asp Phe Glu Asn Phe Tyr Thr Arg Asn Leu
                115                 120                 125 tac atg agg ata aga gac aac tgg aat cgg cca atc tgt agt gtg cct    614
Tyr Met Arg Ile Arg Asp Asn Trp Asn Arg Pro Ile Cys Ser Val Pro
        130                 135                 140 gga gcc agg gtg gac atc atg gag aga cag tct cat gat tat aac tgg    662
Gly Ala Arg Val Asp Ile Met Glu Arg Gln Ser His Asp Tyr Asn Trp
            145                 150                 155 tcc ttc aag tat aca ggg aat ata ata aag ggt gtt ata aac atg ggt    710
Ser Phe Lys Tyr Thr Gly Asn Ile Ile Lys Gly Val Ile Asn Met Gly
160                 165                 170 tcc tac aac tat ctt gga ttt gca cgg aat act gga tca tgt caa gaa    758
Ser Tyr Asn Tyr Leu Gly Phe Ala Arg Asn Thr Gly Ser Cys Gln Glu
175                 180                 185                 190 gca gcc gcc aaa gtc ctt gag gag tat gga gct gga gtg tgc agt act    806
Ala Ala Ala Lys Val Leu Glu Glu Tyr Gly Ala Gly Val Cys Ser Thr
                195                 200                 205 cgg cag gaa att gga aac ctg gac aag cat gaa gaa cta gag gag ctt    854
Arg Gln Glu Ile Gly Asn Leu Asp Lys His Glu Glu Leu Glu Glu Leu
        210                 215                 220 gta gca agg ttc tta gga gta gaa gct gct atg gcg tat ggc atg gga    902
Val Ala Arg Phe Leu Gly Val Glu Ala Ala Met Ala Tyr Gly Met Gly
            225                 230                 235 ttt gca acg aat tca atg aac att cct gct ctt gtt ggc aaa ggt tgc    950
Phe Ala Thr Asn Ser Met Asn Ile Pro Ala Leu Val Gly Lys Gly Cys
240                 245                 250 ctg att ctg agt gat gaa ctg aat cat gca tca ctg gtt ctg gga gcc    998
Leu Ile Leu Ser Asp Glu Leu Asn His Ala Ser Leu Val Leu Gly Ala
255                 260                 265                 270 aga ctg tca gga gca acc att aga atc ttc aaa cac aac aat atg caa    1046
Arg Leu Ser Gly Ala Thr Ile Arg Ile Phe Lys His Asn Asn Met Gln
                275                 280                 285 agc cta gag aag cta ttg aaa gat gcc att gtt tat ggt cag cct cgg    1094
Ser Leu Glu Lys Leu Leu Lys Asp Ala Ile Val Tyr Gly Gln Pro Arg
        290                 295                 300 aca cga agg ccc tgg aag aaa att ctc atc ctt gtg gaa gga ata tat    1142
Thr Arg Arg Pro Trp Lys Lys Ile Leu Ile Leu Val Glu Gly Ile Tyr
            305                 310                 315 agc atg gag gga tct att gtt cgt ctt cct gaa gtg att gcc ctc aag    1190
Ser Met Glu Gly Ser Ile Val Arg Leu Pro Glu Val Ile Ala Leu Lys
320                 325                 330 aag aaa tac aag gca tac ttg tat ctg gat gag gct cac agc att ggc    1238
Lys Lys Tyr Lys Ala Tyr Leu Tyr Leu Asp Glu Ala His Ser Ile Gly
335                 340                 345                 350 gcc ctg ggc ccc aca ggc cgg gtg gtg gag tac ttt ggc ctg gat        1286
Ala Leu Gly Pro Thr Gly Arg Val Val Glu Tyr Phe Gly Leu Asp
                355                 360                 365 ccc gag gat gtg gat gtt atg atg gga acg ttc aca aag agt ttt ggt    1334
Pro Glu Asp Val Asp Val Met Met Gly Thr Phe Thr Lys Ser Phe Gly
        370                 375                 380 gct tct gga gga tat att gga ggc aag aag gag ctg ata gac tac ctg    1382
Ala Ser Gly Gly Tyr Ile Gly Gly Lys Lys Glu Leu Ile Asp Tyr Leu
            385                 390                 395 cga aca cat tct cat agt gca gtg tat gcc acg tca ttg tca cct cct    1430
```

-continued

```
              Arg Thr His Ser His Ser Ala Val Tyr Ala Thr Ser Leu Ser Pro Pro
                  400                 405                 410 gta gtg gag cag atc atc acc tcc atg aag tgc atc atg ggg cag gat         1478
Val Val Glu Gln Ile Ile Thr Ser Met Lys Cys Ile Met Gly Gln Asp
415                 420                 425                 430 ggc acc agc ctt ggt aaa gag tgt gta caa cag tta gct gaa aac acc         1526
Gly Thr Ser Leu Gly Lys Glu Cys Val Gln Gln Leu Ala Glu Asn Thr
                435                 440                 445 agg tat ttc agg aga cgc ctg aaa gag atg ggc ttc atc atc tat gga         1574
Arg Tyr Phe Arg Arg Arg Leu Lys Glu Met Gly Phe Ile Ile Tyr Gly
            450                 455                 460 aat gaa gac tct cca gta gtg cct ttg atg ctc tac atg cct gcc aaa         1622
Asn Glu Asp Ser Pro Val Val Pro Leu Met Leu Tyr Met Pro Ala Lys
                465                 470                 475 att ggc gcc ttt gga cgg gag atg ctg aag cgg aac atc ggt gtc gtt         1670
Ile Gly Ala Phe Gly Arg Glu Met Leu Lys Arg Asn Ile Gly Val Val
        480                 485                 490 gtg gtt gga ttt cct gcc acc cca att att gag tcc aga gcc agg ttt         1718
Val Val Gly Phe Pro Ala Thr Pro Ile Ile Glu Ser Arg Ala Arg Phe
495                 500                 505                 510 tgc ctg tca gca gct cat acc aaa gaa ata ctt gat act gct tta aag         1766
Cys Leu Ser Ala Ala His Thr Lys Glu Ile Leu Asp Thr Ala Leu Lys
                515                 520                 525 gag ata gat gaa gtt ggg gac cta ttg cag ctg aag tat tcc cgt cat         1814
Glu Ile Asp Glu Val Gly Asp Leu Leu Gln Leu Lys Tyr Ser Arg His
            530                 535                 540 cgg ttg gta cct cta ctg gac agg ccc ttt gac gag acg acg tat gaa         1862
Arg Leu Val Pro Leu Leu Asp Arg Pro Phe Asp Glu Thr Thr Tyr Glu
                545                 550                 555 gaa aca gaa gac tga gccttttgg tgctccctca gggaactct ccctcaccca           1917
Glu Thr Glu Asp
            560 ggacagcctg tggcctttgt gagccagttc caggaaccac acttctgtgg ccatctcacg       1977 tgaaagacat tgcctcagct actgaaggtg gccacctcca ctctaaatga cattttgtaa       2037 atagtaaaaa actgcttcta atccttcctt tgctaaatct cacctttaaa aacgaaggtg       2097 actcactttg cttttcagt ccattaaaaa aacattttat tttgcaacca ttctacttgt        2157 gaaatcacgc tgaccctagc ctgtctctgg ctaaccacac aggccattcc cctctcccag       2217 caccttgcag acttgggccc atcaagagct actgctggcc ctggctccgc agcctggata       2277 cttacctggc cctcctccct agggagcaag tgccttccac ttacttccca tccaggtctc      2337 agaggtctca aggccaacct tggaatcctt atttaaccat tcaagtaatc aacggaagtt       2397 ttcacccttt aatcttaagt ttagccttt aagaaaaaca gtaagcgatg actgctgaaa       2457 ggctcattgt gtaatctccc aagggtttgg tcttattcca ttttcttctg gtcaccagat      2517 gatttcttcc tttaccatca aatacttctt cataatggtc acagtctgag gatgtgcgca      2577 aattctggtt cttcccaagc tctaaccgta acacgtccca ccccctttt aaagcactta      2637 ctgttttcag agcacccata tcccaccctg tgagaaggc cactctcaca tctgagtgtt      2697 gggtacaaag ctgctccgta gagtgatgtg cactcctggt gggtgagggg caggggcagt      2757 ggcagtgtgc aaagaattga ttactccttg cagagcctgt ggcttgcatt tcctactgct      2817 ttctacgttt gaaaattatg acagtctctg gctaggtctg gtccagatt aggatttaaa      2877 ctgataaagg aaactgttgg taaatcctct gctcagaaag catttatcat gttcctattt      2937 aaggattagg tttattaatt taggcctctt agaagctaac ccactaaat attactcttc      2997 tgaatgctag ttctctttta ttcttgatgt cctaagtcaa ttgaatctgg catctggggc     3057
```

```
tagggtctgc ctgtctacat attttttatt tttttctgag aaattctgaa cacatagatc   3117
tctttcctaa actgacattt tctattttga ctgttttcat actataacca ggtaaaggga   3177
cttcttttcag agagctttat actgcctgac caaagaacaa atctgaaaat caccatttta  3237
aagttatttt ttcagttgaa ccaaagttta agtgaagagg acttttggca tattataccc   3297
aggatcagtt tgtcttttg tatccatcaa gtattacagg agaaggattg ggaacagaat    3357
ggaaaaacag tgtatgaaag tcatgttaca ggccgagtgc ggtggctcac acctgtaatc   3417
ctagcacttt gggaggctga ggcaggtggc tcacttgagg tcaggaattc aagaccagcc   3477
tggccaacat ggtgaaaccc cgtctctact aaaaagacaa aaaattagct gggcgtggtg   3537
gcgggcacct ataatcccac ctacttggta ggctgaggca ggagaatcgc ttgaacccag   3597
gaggcggagg ttgcagtgag acgagattgt gccactgcac tctagcctgg gtgacagagc   3657
aaaactgtgt ctcaaaaaaa aaagtcatgt tacacattta agtttttgaa attgctcctt   3717
ttatcggtaa agattctcaa tccaaattct cctgggtgtg ttgtcatcag ctgtgatatg   3777
tttgtgcaca ttacgtatag cagaggatgt aagcaatatt attgtttgtg aagttttgtt   3837
tttaatgtct tgagtatgag ttatgtttag tcactgtcag catctgagaa ctttaataag   3897
cccttgagat attccaaagt tttattttac ttttttaaag aacagaaaaa gatgaatgaa   3957
agaaccaagg agagatgcag agactatatt tagcatgtat aggttaaagt aagaaggagg   4017
ttgtggtaac taaataggag tcctataaaa tcaaatacat tgtcaacctt ttctgcacat   4077
ctagtttcct accatagaat cccactggaa taccacatag cttttgcact gcagttacta   4137
tttactaatg taaacgtagg gtttgtaaaa gtcacaaact tataagcaat gaacttacct   4197
gctagtcttt ttattttggc ttgcatgaag tcactgcaaa ttcaaatgtc agtaccggca   4257
tttaaaatat atctatatca ctttgttggt acaaagttat ttcaagataa gtgtaatttt   4317
gttacaagtt tattttgaag agacaaatct cctgtgatct atgcaggacc tctgtacttt   4377
ctaaagaaca aaatgttatg tagacattat acatggttgg ttgtctcttc ttgaaactgt   4437
aatgtaaatc tagggtccag tcatatccta ggtatcatca tttatccaag tacttggagg   4497
aatacaagta tatataaata cagtcattga gaataagtcg atttgaggca tacaagagta   4557
gtttcttaca cagtttaaca cggcctgatt caagactctg ataggattca aacagatacc   4617
ggttaaccat gactaccaaa actgatcatc tgagtcgatt gatagaggtg tgactagtcc   4677
ttagcacttt ttctcattcc tctttttatt cagcattgct gttacctatt tcaggtttat   4737
aagacctctt tcagcagatc acatcagaag ccaggaaatg catagctagg agatgtcaaa   4797
agcccatatg aggagtggac caagcagcag tggcggtttc tcctcgcatc tttttttttt   4857
taagctttaa cttagcaggg gcatggactt tatagcactt tttcaacttt ttgctttgct   4917
ttggataaga aatccttacc tttaaaaaaa gcttctagtc tccataaccc ccaaagtact   4977
gcttatttgt ttgaagaatc cagccatcgt agtgctttag tcactatcgt aaacattcat   5037
gatagggcaa ggattttaaa acaggattct tgcttctgta gtcatcaagg tgaacagaag   5097
catcctacac aaccactaag ggctctatgt ttgtgtcatg cctcttcaaa caccaaggag   5157
ttgaacatgc ttccagtgat ttgtctccgt aatgccttct tcctttatt ggcctttctt    5217
tctttctgta ccttcaagtt cttgattttt aaaattccaa ctctagagaa aaccaatata   5277
tggtggtgct gggctttgaa gatagcatat cagacgcctt ggttctgttt gtacacttag   5337
ccttacattt caggaggagg cttttcatta ggggcttaag ctagctccctt tggcttttaa  5397
aaaaaatttt ttttcaaatt tcttcattac ctaagggagc ctgcatctaa atttctcaac   5457
```

```
tagttcagcc tagctgaatt ttctagtgtg taatacactt tgcttccttc ttattggtga   5517
aaaccagggg gatgagtggc ttccatggag agatttcctg atttctcagg gaggaaaaaa   5577
gtgatgacat ttaccactac ttttatgttt ttccccttttt tccaaattga taaggatttc   5637
tggttcctag tgatccggga ttgggcaaca gtgcagaact gccagtcatg ccgtaggccg   5697
tgaagaaaga atgtgagtaa ctgttgtttt gcaaggatttt gtagggttat ggcagttgt    5757 tgtttgaagc attgctatga cctaattccc aaggtatctt tcctctcttg gtgttctagg   5817
taagccaatg agctttaatc tctacttgct ataaccgtgt gcttagaaaa agaggtgaga   5877
gtagtggttt tccttcaaac tgtccacatt catgaagatt atgaattgtt aggacagcca   5937
gggcaagata gaccctgtct ctacaaaaat ttttttctaa attaaccggg catggtggtg   5997
cctgcctgta gtcccacctg tgtgggagaa tcacttgagc ctgggaggtc aaggctgcag   6057
tgagccatga ttgcacccct gcactccagc ctgggtgaca gagtgagacc ctggctcaat   6117 aagagggga aaaaaaattg ttaggagctg ggtgcggatg cagcctgcaa tcccagctac    6177
ttgagaggct gaggccggag gattgcttaa acccaagaat ttgagcgtag cctgggcaac   6237
acagcaagac cccatctaag aaaaaaatgt ttttaaatc agcttagccc aaaggggttg   6297
tgaatgggga ggtataaaaa gcaaagatta tttttggct actaagccaa gaacttacag    6357 ggatttttt tttcagtccc agaacctaca gatacctgc tacttgcttc acgtggatgc     6417
tcagtgccca gcagccatct taatacatta aaccagttta aaaaatacct tccatgtgga   6477
gaaaaacatg tcttttttctc gcctcaactt tatcccacatg aaatgtgtgc ccatggctgg   6537
gcgcagtggc tcacctgtaa tcccaacact ttgggaggct gaagcaggca gattgcttga   6597
ggccaggagt tcgagaacag tctggccaac atggcgaaac ctcatctcta ctaaaattac    6657
aaaaattagc cgggcatggt ggcacatgcc tgtaatccca gctacgtcag gaggctgagg   6717
cacaggaatt gcttgaaccc aagaggcaga ggatgcaatg agccaagatc acaccactgc   6777
actccagcct tggcgacaga gggagactct gtctcaaaaa aaaaaaaaaa aggtgtgccc   6837
aggcccctag ccattgccat gtgcccagcc agagagccaa attagagggc tggcttccct   6897
atcacacaga ataaatgcta gtgctagcca atgatcccttt tgcttttaat gtatagaaaa   6957
tactgttgtt ccttttgtca tttccagtga catctgtttt ctaagcagct cttttctagg    7017
gaggaaacca aaggggctag gttaagaccc taatagaaat gttttttcta atctctggtg   7077
agtctggaag tgtcacattc acagtccacc cttgggagtg gcttggtgga gctgggaca    7137 aggtttttgtt tactacatag tgcacatgat aaatggcctt aaactgtgat tctttctggt   7197
aggataagtt ataataaact gaccctaaag aatgcaaaaa aaaaaaaaaa aaa          7250
```

<210> SEQ ID NO 7
<211> LENGTH: 562
<212> TYPE: PRT
<213> ORGANISM: Homo sapiens

<400> SEQUENCE: 7

```
Met Arg Pro Glu Pro Gly Gly Cys Cys Cys Arg Arg Thr Val Arg Ala
1               5                   10                  15

Asn Gly Cys Val Ala Asn Gly Glu Val Arg Asn Gly Tyr Val Arg Ser
            20                  25                  30

Ser Ala Ala Ala Ala Ala Ala Ala Ala Gly Gln Ile His His Val
        35                  40                  45

Thr Gln Asn Gly Gly Leu Tyr Lys Arg Pro Phe Asn Glu Ala Phe Glu
    50                  55                  60
```

-continued

Glu Thr Pro Met Leu Val Ala Val Leu Thr Tyr Val Gly Tyr Gly Val
65                  70                  75                  80

Leu Thr Leu Phe Gly Tyr Leu Arg Asp Phe Leu Arg Tyr Trp Arg Ile
                85                  90                  95

Glu Lys Cys His His Ala Thr Glu Arg Glu Gln Lys Asp Phe Val
            100                 105                 110

Ser Leu Tyr Gln Asp Phe Glu Asn Phe Tyr Thr Arg Asn Leu Tyr Met
            115                 120                 125

Arg Ile Arg Asp Asn Trp Asn Arg Pro Ile Cys Ser Val Pro Gly Ala
        130                 135                 140

Arg Val Asp Ile Met Glu Arg Gln Ser His Asp Tyr Asn Trp Ser Phe
145                 150                 155                 160

Lys Tyr Thr Gly Asn Ile Ile Lys Gly Val Ile Asn Met Gly Ser Tyr
                165                 170                 175

Asn Tyr Leu Gly Phe Ala Arg Asn Thr Gly Ser Cys Gln Glu Ala Ala
            180                 185                 190

Ala Lys Val Leu Glu Glu Tyr Gly Ala Gly Val Cys Ser Thr Arg Gln
        195                 200                 205

Glu Ile Gly Asn Leu Asp Lys His Glu Glu Leu Glu Leu Val Ala
210                 215                 220

Arg Phe Leu Gly Val Glu Ala Ala Met Ala Tyr Gly Met Gly Phe Ala
225                 230                 235                 240

Thr Asn Ser Met Asn Ile Pro Ala Leu Val Gly Lys Gly Cys Leu Ile
                245                 250                 255

Leu Ser Asp Glu Leu Asn His Ala Ser Leu Val Leu Gly Ala Arg Leu
            260                 265                 270

Ser Gly Ala Thr Ile Arg Ile Phe Lys His Asn Asn Met Gln Ser Leu
        275                 280                 285

Glu Lys Leu Leu Lys Asp Ala Ile Val Tyr Gly Gln Pro Arg Thr Arg
290                 295                 300

Arg Pro Trp Lys Lys Ile Leu Ile Leu Val Glu Gly Ile Tyr Ser Met
305                 310                 315                 320

Glu Gly Ser Ile Val Arg Leu Pro Glu Val Ile Ala Leu Lys Lys Lys
                325                 330                 335

Tyr Lys Ala Tyr Leu Tyr Leu Asp Glu Ala His Ser Ile Gly Ala Leu
            340                 345                 350

Gly Pro Thr Gly Arg Gly Val Val Glu Tyr Phe Gly Leu Asp Pro Glu
        355                 360                 365

Asp Val Asp Val Met Met Gly Thr Phe Thr Lys Ser Phe Gly Ala Ser
370                 375                 380

Gly Gly Tyr Ile Gly Gly Lys Lys Glu Leu Ile Asp Tyr Leu Arg Thr
385                 390                 395                 400

His Ser His Ser Ala Val Tyr Ala Thr Ser Leu Ser Pro Pro Val Val
                405                 410                 415

Glu Gln Ile Ile Thr Ser Met Lys Cys Ile Met Gly Gln Asp Gly Thr
            420                 425                 430

Ser Leu Gly Lys Glu Cys Val Gln Gln Leu Ala Glu Asn Thr Arg Tyr
        435                 440                 445

Phe Arg Arg Arg Leu Lys Glu Met Gly Phe Ile Ile Tyr Gly Asn Glu
        450                 455                 460

Asp Ser Pro Val Val Pro Leu Met Leu Tyr Met Pro Ala Lys Ile Gly
465                 470                 475                 480

Ala Phe Gly Arg Glu Met Leu Lys Arg Asn Ile Gly Val Val Val Val

```
                         485                 490                 495
Gly Phe Pro Ala Thr Pro Ile Ile Glu Ser Arg Ala Arg Phe Cys Leu
            500                 505                 510

Ser Ala Ala His Thr Lys Glu Ile Leu Asp Thr Ala Leu Lys Glu Ile
            515                 520                 525

Asp Glu Val Gly Asp Leu Leu Gln Leu Lys Tyr Ser Arg His Arg Leu
            530                 535                 540

Val Pro Leu Leu Asp Arg Pro Phe Asp Glu Thr Thr Tyr Glu Glu Thr
545                 550                 555                 560

Glu Asp

<210> SEQ ID NO 8
<211> LENGTH: 1967
<212> TYPE: DNA
<213> ORGANISM: Homo sapiens
<220> FEATURE:
<221> NAME/KEY: CDS
<222> LOCATION: (338)..(1579)

<400> SEQUENCE: 8
aaatgcaaaa cagtggctgt tgcaggtgat ggaactgtac tggaacaatg ggagaagctg     60
gtagcttata ggaagccaag atgaccagaa tgttttaaa taatccaagg aagaatcctg    120
ctcaaaaatg aggtgaatta atacttgggc gctcaggaac cctggacagc tacatgaggt    180
gtttaaaaac tgccctgacc atcttgccaa acaagtctct gctcatgagg ccccacagga    240
tgaacgagcc gaggcaggac agtgtcctgc cctgtcggaa cagtgactgc tgacctgcca    300
agagagagct ggggactgcc tgctgtctgc cagtaca atg aag gaa gtg gtt tat     355
                                          Met Lys Glu Val Val Tyr
                                            1               5 tgg tca ccc aag aag gtg gca gac tgg ctg ctg gag aat gct atg cca     403
Trp Ser Pro Lys Lys Val Ala Asp Trp Leu Leu Glu Asn Ala Met Pro
            10                  15                  20 gaa tac tgt gag cct ctg gag cat ttc aca ggc cag gac ttg atc aac     451
Glu Tyr Cys Glu Pro Leu Glu His Phe Thr Gly Gln Asp Leu Ile Asn
        25                  30                  35 cta acc caa gag gat ttc aaa aaa ccc ccc ttg tgc cga gtc tcc tct     499
Leu Thr Gln Glu Asp Phe Lys Lys Pro Pro Leu Cys Arg Val Ser Ser
    40                  45                  50 gac aat ggg cag cgg ctc ctg gac atg ata gaa acc ctg aaa atg gag     547
Asp Asn Gly Gln Arg Leu Leu Asp Met Ile Glu Thr Leu Lys Met Glu
55                  60                  65                  70 cac cat ttg gaa gca cac aag aac ggc cat gcc aat ggg cac ctc aac     595
His His Leu Glu Ala His Lys Asn Gly His Ala Asn Gly His Leu Asn
                75                  80                  85 att ggc gta gac atc ccc acc ccc gac ggc agc ttc agc atc aag att     643
Ile Gly Val Asp Ile Pro Thr Pro Asp Gly Ser Phe Ser Ile Lys Ile
            90                  95                 100 aaa ccc aac ggg atg cca aat ggg tat agg aaa gag atg ata aag atc     691
Lys Pro Asn Gly Met Pro Asn Gly Tyr Arg Lys Glu Met Ile Lys Ile
        105                 110                 115 ccc atg cca gaa ctg gag cgc tct cag tac ccc atg gag tgg ggc aag     739
Pro Met Pro Glu Leu Glu Arg Ser Gln Tyr Pro Met Glu Trp Gly Lys
    120                 125                 130 act ttt ctg gcc ttt ctt tat gca ctt tcc tgt ttc gtt ctc acc aca     787
Thr Phe Leu Ala Phe Leu Tyr Ala Leu Ser Cys Phe Val Leu Thr Thr
135                 140                 145                 150 gtg atg atc tcg gtc gtc cac gaa cga gta cct cct aag gag gtg cag     835
Val Met Ile Ser Val Val His Glu Arg Val Pro Pro Lys Glu Val Gln
                155                 160                 165
```

```
cct cca cta ccg gac aca ttt ttt gac cat ttt aac cgg gtg cag tgg      883
Pro Pro Leu Pro Asp Thr Phe Phe Asp His Phe Asn Arg Val Gln Trp
            170                 175                 180 gcc ttt tct att tgt gaa att aat ggc atg atc ctt gta gga ctc tgg      931
Ala Phe Ser Ile Cys Glu Ile Asn Gly Met Ile Leu Val Gly Leu Trp
            185                 190                 195 tta att cag tgg ctg ctc tta aaa tac aag tct att att agc aga aga      979
Leu Ile Gln Trp Leu Leu Leu Lys Tyr Lys Ser Ile Ile Ser Arg Arg
    200                 205                 210 ttt ttc tgc ata gtt ggc acg ctg tac ctg tat cgg tgt att aca atg     1027
Phe Phe Cys Ile Val Gly Thr Leu Tyr Leu Tyr Arg Cys Ile Thr Met
215                 220                 225                 230 tat gta act aca ctc cca gta cct ggt atg cat ttc aac tgt tct ccg     1075
Tyr Val Thr Thr Leu Pro Val Pro Gly Met His Phe Asn Cys Ser Pro
                235                 240                 245 aag ctt ttc gga gac tgg gaa gcc caa ctg cga aga ata atg aag ctc     1123
Lys Leu Phe Gly Asp Trp Glu Ala Gln Leu Arg Arg Ile Met Lys Leu
            250                 255                 260 att gct gga ggt ggc ttg tct atc act ggc tct cac aac atg tgt ggg     1171
Ile Ala Gly Gly Gly Leu Ser Ile Thr Gly Ser His Asn Met Cys Gly
            265                 270                 275 gac tat ctg tac agc ggc cac acg gtc atg cta aca ctt acc tac tta     1219
Asp Tyr Leu Tyr Ser Gly His Thr Val Met Leu Thr Leu Thr Tyr Leu
        280                 285                 290 ttt atc aaa gag tat tcc cct cgg cga ctc tgg tgg tat cac tgg att     1267
Phe Ile Lys Glu Tyr Ser Pro Arg Arg Leu Trp Trp Tyr His Trp Ile
295                 300                 305                 310 tgc tgg ctt ctc agc gta gtt gga atc ttc tgt att ctc tta gcg cat     1315
Cys Trp Leu Leu Ser Val Val Gly Ile Phe Cys Ile Leu Leu Ala His
                315                 320                 325 gac cac tac act gtg gac gtg gtg gtg gca tat tac atc acc acg aga     1363
Asp His Tyr Thr Val Asp Val Val Val Ala Tyr Tyr Ile Thr Thr Arg
            330                 335                 340 ctc ttc tgg tgg tat cac act atg gcc aat cag caa gtg cta aag gaa     1411
Leu Phe Trp Trp Tyr His Thr Met Ala Asn Gln Gln Val Leu Lys Glu
            345                 350                 355 gct tcc cag atg aac ctc ctg gcc agg gtg tgg tgg tac agg cca ttt     1459
Ala Ser Gln Met Asn Leu Leu Ala Arg Val Trp Trp Tyr Arg Pro Phe
        360                 365                 370 cag tac ttt gaa aag aat gtc caa gga att gta cct cga tct tac cat     1507
Gln Tyr Phe Glu Lys Asn Val Gln Gly Ile Val Pro Arg Ser Tyr His
375                 380                 385                 390 tgg cct ttc ccc tgg cca gta gtc cac ctc agt agg caa gtt aaa tac     1555
Trp Pro Phe Pro Trp Pro Val Val His Leu Ser Arg Gln Val Lys Tyr
                395                 400                 405 agc cgg ctg gtg aat gac aca taa cagctgtaca aagtggggaa aagacaaatt    1609
Ser Arg Leu Val Asn Asp Thr
            410 gtccgaagtg ctaagaactc catgagagaa gatgccataa aataaacacc tccctaatcc   1669 tattatcttt caatggttac cttgacttaa cctattgagt tacctggtca gcactgtgat   1729 ctttttttct ctccaaagga cctgcgttgg acaacaataa agaaaaattt aacctatcat   1789 gcactgtaca catttcctgt tcataagttt gggatttaca taacccgcaa ccaccatgtt   1849 cctttgtata tgatgcagca gcataaatgt aagcttttat atcataagtt ctggtctttc   1909 cagtcacatc tggaaataaa gcgtactatt ttcttgggaa aaaaaaaaaa aaaaaaa      1967

<210> SEQ ID NO 9
<211> LENGTH: 413
```

<212> TYPE: PRT
<213> ORGANISM: Homo sapiens

<400> SEQUENCE: 9

```
Met Lys Glu Val Val Tyr Trp Ser Pro Lys Lys Val Ala Asp Trp Leu
1               5                   10                  15

Leu Glu Asn Ala Met Pro Glu Tyr Cys Glu Pro Leu Glu His Phe Thr
                20                  25                  30

Gly Gln Asp Leu Ile Asn Leu Thr Gln Glu Asp Phe Lys Lys Pro Pro
            35                  40                  45

Leu Cys Arg Val Ser Ser Asp Asn Gly Gln Arg Leu Leu Asp Met Ile
        50                  55                  60

Glu Thr Leu Lys Met Glu His His Leu Glu Ala His Lys Asn Gly His
65                  70                  75                  80

Ala Asn Gly His Leu Asn Ile Gly Val Asp Ile Pro Thr Pro Asp Gly
                85                  90                  95

Ser Phe Ser Ile Lys Ile Lys Pro Asn Gly Met Pro Asn Gly Tyr Arg
            100                 105                 110

Lys Glu Met Ile Lys Ile Pro Met Pro Glu Leu Glu Arg Ser Gln Tyr
        115                 120                 125

Pro Met Glu Trp Gly Lys Thr Phe Leu Ala Phe Leu Tyr Ala Leu Ser
130                 135                 140

Cys Phe Val Leu Thr Thr Val Met Ile Ser Val Val His Glu Arg Val
145                 150                 155                 160

Pro Pro Lys Glu Val Gln Pro Pro Leu Pro Asp Thr Phe Phe Asp His
                165                 170                 175

Phe Asn Arg Val Gln Trp Ala Phe Ser Ile Cys Glu Ile Asn Gly Met
            180                 185                 190

Ile Leu Val Gly Leu Trp Leu Ile Gln Trp Leu Leu Leu Lys Tyr Lys
        195                 200                 205

Ser Ile Ile Ser Arg Arg Phe Phe Cys Ile Val Gly Thr Leu Tyr Leu
        210                 215                 220

Tyr Arg Cys Ile Thr Met Tyr Val Thr Thr Leu Pro Val Pro Gly Met
225                 230                 235                 240

His Phe Asn Cys Ser Pro Lys Leu Phe Gly Asp Trp Glu Ala Gln Leu
                245                 250                 255

Arg Arg Ile Met Lys Leu Ile Ala Gly Gly Leu Ser Ile Thr Gly
            260                 265                 270

Ser His Asn Met Cys Gly Asp Tyr Leu Tyr Ser Gly His Thr Val Met
        275                 280                 285

Leu Thr Leu Thr Tyr Leu Phe Ile Lys Glu Tyr Ser Pro Arg Arg Leu
        290                 295                 300

Trp Trp Tyr His Trp Ile Cys Trp Leu Leu Ser Val Val Gly Ile Phe
305                 310                 315                 320

Cys Ile Leu Leu Ala His Asp His Tyr Thr Val Asp Val Val Val Ala
                325                 330                 335

Tyr Tyr Ile Thr Thr Arg Leu Phe Trp Trp Tyr His Thr Met Ala Asn
            340                 345                 350

Gln Gln Val Leu Lys Glu Ala Ser Gln Met Asn Leu Leu Ala Arg Val
        355                 360                 365

Trp Trp Tyr Arg Pro Phe Gln Tyr Phe Glu Lys Asn Val Gln Gly Ile
        370                 375                 380

Val Pro Arg Ser Tyr His Trp Pro Phe Pro Trp Pro Val His Leu
385                 390                 395                 400
```

-continued

```
Ser Arg Gln Val Lys Tyr Ser Arg Leu Val Asn Asp Thr
                405                 410

<210> SEQ ID NO 10
<211> LENGTH: 34
<212> TYPE: PRT
<213> ORGANISM: Homo sapiens

<400> SEQUENCE: 10

Glu Asn Asp Ile Arg Val Glu Glu Ser Ile Tyr Gln Cys Cys Asp Leu
1               5                   10                  15

Ala Pro Glu Ala Arg Gln Ala Ile Lys Ser Leu Thr Glu Arg Leu Tyr
                20                  25                  30

Ile Gly

<210> SEQ ID NO 11
<211> LENGTH: 34
<212> TYPE: PRT
<213> ORGANISM: Homo sapiens

<400> SEQUENCE: 11

Cys Thr Arg Pro Asn Asn Asn Thr Arg Lys Ser Ile His Ile Gly Pro
1               5                   10                  15

Gly Arg Ala Phe Tyr Thr Thr Gly Glu Ile Ile Gly Asp Ile Arg Gln
                20                  25                  30

Ala His
```

PHARMACEUTICAL AGENTS FOR TREATING HCV INFECTIONS

CROSS-REFERENCE TO RELATED APPLICATIONS

This application is the National Stage of International Application No. PCT/JP2005/014767, filed on Aug. 11, 2005, which claims the benefit of Japanese Patent Application Serial No. 2004-234900, filed on Aug. 11, 2004.

TECHNICAL FIELD

The present invention relates to pharmaceutical agents for treating or preventing HCV infections, which comprise compounds that block a process of sphingomyelin biosynthesis as active ingredients. The present invention also relates to methods of screening for pharmaceutical agents for treating or preventing HCV infections, and kits for use in such methods.

BACKGROUND ART

The number of HCV-infected people in the world is estimated to be one to two hundred million, with two million or more estimated to be infected in Japan. Approximately 50% of these patients undergo a transition to chronic hepatitis; thirty or more years after infection, approximately 20% of these will develop hepatic cirrhosis and liver cancer. Approximately 90% of liver cancers are said to be caused by hepatitis C. In Japan, 20,000 or more patients die every year due to liver cancers associated with HCV infection.

HCV was discovered in 1989 as a major causative virus of post-transfusion non-A and non-B hepatitis. HCV is an enveloped RNA virus whose genome consists of a single-stranded (+) RNA, and is classified into the genus *Hepacivirus* of the family Flaviviridae.

HCV evades the host immune mechanism for an as yet unknown reason. Therefore, even when adults with a mature immune mechanism are infected, persistent infections are established in many cases, and this develops into chronic hepatitis, liver cirrhosis, and liver cancer. Even when the cancers are removed by surgery, many patients are known to have recurring liver cancer due to the inflammation continuously induced in non-cancerous parts.

The establishment of effective therapeutic methods for hepatitis C is therefore desired. In addition to response therapies that suppress inflammation using anti-inflammatory agents, the development of pharmaceutical agents that reduce or eradicate HCV in the liver, which is the affected area, is particularly strongly desired.

Currently, interferon treatment is known to be the only effective therapeutic method for eliminating HCV. However, interferons are effective for approximately one third of all patients. The effectiveness of interferons against HCV genotype 1b is particularly low. There is therefore a strong desire to develop anti-HCV agents that may be used instead of, or together with, interferons.

In recent years, Ribavirin (1-β-D ribofuranosyl-1H-1,2,4-triazole-3-carboxamide) has been commercially available as a therapeutic agent for hepatitis C for combined use with interferons; however, its efficacy ratio is still low and additional novel therapeutic agents for hepatitis C are desired. Attempts have also been made to eliminate the virus by strengthening patient immune systems using interferon agonists, interleukin-12 agonists, and such, but effective pharmaceutical agents have not yet been found.

Since cloning the HCV gene, molecular biological analyses of the mechanism and function of the viral gene, the function of each of the viral proteins, and such has progressed rapidly; however, the mechanisms of replication, persistent infection, pathogenicity, and such of the virus in host cells have not been sufficiently clarified, and experimental HCV infection systems using reliable cultured cells have not been constructed. Therefore, evaluation of anti-HCV agents has conventionally required alternative viral assay methods that use other related viruses.

In recent years, however, it has become possible to observe HCV replication in vitro using non-structural regions of HCV, and replicon assay methods have enabled easy evaluation of anti-HCV agents (Non-Patent Document 1). The mechanism of HCV RNA replication in this system is considered identical to the replication of a full length HCV RNA genome that has infected liver cells. This system can therefore be a cell-based assay system useful for identifying compounds that inhibit HCV replication.

Prior art references relating to the present invention of this application are shown below.

[Patent Document 1] International Publication WO98/56755 pamphlet
[Patent Document 2] Japanese Patent Application No. 2003-34056
[Patent Document 3] Japanese Patent Application No. 2003-272420
[Non-Patent Document 1] V. Lohmann et al., Science (1999) 285:110-113.

DISCLOSURE OF THE INVENTION

Problems to Be Solved by the Invention

The present inventors discovered that a series of compounds derived from microorganisms such as the genus *Aureobasidium* and disclosed in International Publication WO98/56755 (Patent Document 1) have strong inhibitory activity against HCV replication in the above replicon assay methods (Patent Document 2). The present inventors also discovered that these compounds have slight in vitro cytotoxicity and are very useful as preventive or therapeutic agents for HCV infection, and they further developed methods for synthesizing these compounds and their derivatives (Patent Document 3). These inhibitors are highly likely to become therapeutic agents for HCV infections. However, since the kinds of abnormalities induced by HCV in a living body and the types of in vivo reactions inhibited by this series of compounds have not yet been elucidated, there have been concerns about the behavior of these compounds when used as pharmaceutical agents. Furthermore, regarding the use of these compounds as pharmaceuticals, there has been a demand for elucidation of in vivo cascades in which these compounds are involved to induce inhibitory activity against HCV replication.

The present invention was achieved in view of the above circumstances. An objective of the present invention is to elucidate in vivo cascades in which the series of compounds derived from microorganisms such as the genus *Aureobasidium* and derivatives thereof are involved to induce inhibitory activity against HCV replication. Another objective is to identify the cascades inhibited by these compounds, and thus to provide pharmaceutical agents for treating or preventing HCV infection, where these agents comprise as active ingredients compounds that block these cascades. A further objective is to elucidate the mechanisms of HCV infection and of the activity of inhibiting HCV replication, and to thus provide methods of screening for pharmaceutical agents for treating or preventing HCV infections, and kits for use in such screening methods.

Means to Solve the Problems

To solve the above-mentioned problems, the present inventors first performed HCV replicon assays on the compound below, represented by formula (II), which is a compound derived from microorganisms such as the genus *Aureobasidium*, and on myriocin, which has partial structural similarity to this compound.

Formula (II):

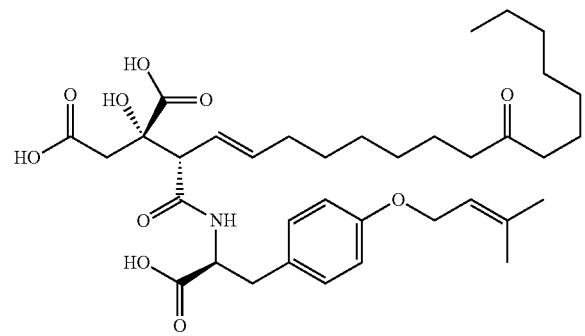

Myriocin is a compound that specifically inhibits serine palmitoyltransferase (SPT), which produces 3-ketodihydrosphingosine by condensing serine and palmitoyl CoA in the early stages of sphingolipid biosynthesis (FIG. 1) (Zwerink, M. M., Edison, A., M., Wells, G. B., Pinto, W., Lester, R. L., J. Biol. Chem., 267, 25032-25038 (1992)). Myriocin has the activity of stopping the entire sphingolipid biosynthesis.

Between 1 pM and 100 µM of the compound represented by formula (II) or myriocin was added to Huh-3-1 replicon cells, these were cultured, total RNA was extracted, and then Northern blot analysis was performed using a neomycin-resistance gene as a probe. Results showed that at concentrations of 1 to 10 nM, myriocin and the compound represented by formula (II) had the effect of decreasing replicon RNA by 50% (FIGS. 2 and 3). Further, between 1 pM and 100 µM of myriocin or the compound represented by formula (II) was added to Huh-3-1 replicon cells, which were then cultured, and after proteins were collected, Western blot analysis was performed using an anti-NS3 rabbit antibody derived from an HCV protein. Results showed that at concentrations of 1 to 10 nM, myriocin and the compound represented by formula (II) had the effect of decreasing HCV protein expression by 50% (FIGS. 4 and 5).

Next, inhibitory activity against the HCV replicon was measured for fumonisin B1, which specifically inhibits dihydrosphingosine-N-acyltransferase that produces dihydroceramide from dihydrosphingosine midway through the process of sphingolipid biosynthesis. Between 1.37 µM and 1000 µM of fumonisin B1 was added to Huh-3-1 replicon cells, which were then cultured before luminescence was measured. Results showed that at concentrations of 10 to 1000 µM, fumonisin B1 had the activity of inhibiting the HCV replicon (FIG. 6).

The above results suggested that myriocin, a compound that specifically inhibits serine palmitoyltransferase (SPT), and fumonisin B1, which specifically inhibits dihydrosphingosine-N-acyltransferase, have inhibitory activity against HCV replication, and that sphingolipid synthesis is involved in HCV infection. Accordingly, to confirm whether inhibition of serine palmitoyltransferase, which catalyzes one of the processes in sphingolipid biosynthesis, is directly involved with inhibition of HCV replicon activity, the present inventors performed serine palmitoyltransferase knockdown experiments using siRNAs. First, two kinds of specific siRNAs (si246 and si633) were synthesized to target LCB1, a subunit of the serine palmitoyltransferase heterodimer. When Western blot analysis was used to measure inhibition of LCB1 expression by the siRNAs, both kinds of siRNAs demonstrated inhibition of expression as compared to a control siRNA, and si246 showed particularly strong inhibition of expression (FIG. 7).

Further, LCB1 was knocked down using the siRNAs, and the activity of inhibiting the HCV replicon was measured. Specifically, the influence of conditions of reduced LCB1 expression on cytotoxicity and HCV replicon activity in Huh-3-1 cells were measured. As a result, HCV replicon activity in si246-treated and si633-treated cells with suppressed LCB1 expression was significantly inhibited as compared to control siRNA-treated cells, and a particularly strong inhibitory effect was observed with si246, which strongly suppressed LCB1 expression (FIG. 8). In addition, when the effect of siRNA treatment on cytotoxicity was examined under the same conditions, almost no effect was observed. These results revealed that sphingolipid biosynthesis is involved in HCV infections, suggesting that HCV infection can be treated or prevented by inhibiting the activity of enzymes present in this biosynthetic process.

Next, HCV replicon cells were treated with 100 nM of the compound represented by formula (II) for 96 hours. Confirmation of inhibition of HCV-NS3 protein expression showed that the addition of the compound represented by formula (II) had led to the disappearance of the HCV-NS3 protein around the nucleus (FIG. 10). Further, when HCV replicon cells were treated with 100 nM of the compound represented by formula (II) for 48 hours and 96 hours, and the expression of HCV non-structural proteins, NS3, NS5A, and NS5B, was checked by Western blot analysis, the expression of all proteins was found to have decreased (FIG. 11). These results showed that the compound represented by formula (II) have the effect of suppressing the expression of non-structural proteins, NS3, NS5A, and NS5B, which are involved in the viral replication of HCV.

Next, a human recombinant SPT (a heterodimer of LCB1 and LCB2) protein was prepared, and when the activity of the compound represented by formula (II) in inhibiting SPT was measured, this compound represented by formula (II) was found to have the activity of inhibiting SPT with an IC50 of approximately 10 nM (FIG. 12).

HCV replicon cells were then treated with the compound represented by formula (II) for 48 hours, and labeling with [14C]serine showed that the compound represented by formula (II) inhibits the intracellular de novo synthesis of ceramide and sphingomyelin in a concentration-dependent manner (FIG. 13). When cell-permeable ceramide (C2-ceramide) and the compound represented by formula (II) were added simultaneously to HCV replicon cells and then cultured, inhibition of HCV replication by the compound represented by formula (II) was suppressed in a manner dependent on C2-ceramide concentration (FIG. 14).

Next, HCV replicon cells were treated with known SPT inhibitor myriocin, ceramide synthesis inhibitor fumonisin B1, and ceramide trafficking inhibitor HPA-12, and when the replicon activity and viable cell count were measured, each of these compounds was found to suppress HCV replication at a non-cytotoxic concentration (FIG. 15).

1 mM of the compound represented by formula (II) was then added to HCV replicon cells, and confirmation of raft protein expression showed that the compound represented by formula (II) reduced NS5B protein expression in the solubilizer-resistant fraction (FIG. 16). However, the effects of the compound represented by formula (II) on NS5A and the host's raft-associated protein caveolin-2 could not be confirmed. Further, when 1 mM of the compound represented by formula (II) was added to HCV replicon cells, and raft proteins (solubilizer-resistant) and non-raft proteins were separated by sucrose density gradient fractionation method, NS5B showed significant dissociation from the raft (FIG. 17).

Specifically, the present inventors succeeded in developing pharmaceutical agents for treating or preventing HCV infections, which comprise compounds that block the process of sphingomyelin biosynthesis as active ingredients, and thus accomplished the present invention.

So far, studies to elucidate the mechanism and function of the HCV gene have been conducted, and development of therapeutic agents for HCV that target non-structural HCV proteins has progressed; however, since the non-structural proteins themselves may be modified during replication, development of effective therapeutic agents has been difficult. The present invention found that sphingomyelin biosynthesis is involved in HCV replication, and elucidated the mechanism of viral replication in host cells. The findings of the present invention greatly contribute to the development of anti-HCV agents which have the sphingomyelin biosynthetic system as a novel host target. Since the cascades targeted have so far been unclear, the side effects of conventional anti-HCV agents have been of some concern; however, the pharmaceutical agents of the present invention have a more specific target, which is the sphingomyelin biosynthetic system, and this may allow simple elimination of side effects, regulation of the effects of the pharmaceutical agents, and such. Further, the anti-HCV agents of the present invention may show broad anti-HCV effects, regardless of the HCV subtype and variety of protein modifications.

More specifically, the present invention provides the following [1] to [23]:

[1] a pharmaceutical agent for treating or preventing an HCV infection, which comprises as an active ingredient a compound that blocks a process of sphingomyelin biosynthesis;

[2] the pharmaceutical agent of [1], wherein the process is sphingomyelin biosynthesis from palmitoyl CoA;

[3] the pharmaceutical agent of [2], which comprises (a) or (b) as an active ingredient:

(a) a compound that inhibits an enzyme activity of serine palmitoyltransferase (SPT), which is involved in 3-ketodihydrosphingosine biosynthesis from palmitoyl CoA, or (b) a compound that suppresses expression of serine palmitoyltransferase (SPT);

[4] the pharmaceutical agent of [3], wherein the compound that inhibits the enzyme activity of serine palmitoyltransferase is sphingofungin, myriocin, or a compound represented by formula (I) or a derivative thereof:

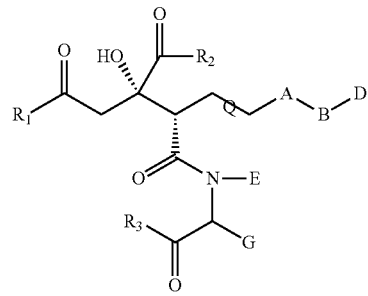

wherein
A represents —$(CH_2)_n$—,
wherein n is an integer from 0 to 10;
B represents —$CH_2$—, —$(C=O)$—, —$CH(OH)$—, —$CH(NH_2)$—, or —$C(=NOR)$—,
wherein R represents a hydrogen atom, or a straight-chain or branched-chain alkyl group of one to eight carbon atoms, which can be substituted or unsubstituted with an amino group that may be optionally mono- or di-substituted with a straight-chain or branched-chain alkyl group of one to four carbon atoms;
D represents —$(CH_2)_m$—R',
wherein m is an integer from 0 to 10; and
R' represents a hydrogen atom; a straight-chain or branched-chain alkyl group; straight-chain or branched-chain alkynyl group; straight-chain or branched-chain alkenyl group; cycloalkyl group; substituted or unsubstituted heterocyclic group; substituted or unsubstituted aryl group; substituted or unsubstituted heteroaryl group; —OX group, wherein X denotes a hydrogen atom, or a straight-chain or branched-chain alkyl group, straight-chain or branched-chain alkynyl group, straight-chain or branched-chain alkenyl group, cycloalkyl group, or substituted or unsubstituted aryl group; or a halogen atom;
E represents a hydrogen atom or a straight-chain or branched-chain alkyl group;
G represents —$(CH_2)_p$-J,
wherein p is an integer of 0 to 4; and
J represents a hydrogen atom, OH group, SH group, methylthio group, carboxyl group, carbamoyl group, amino group, guanidino group, straight-chain or branched-chain alkyl group, cycloalkyl group, straight-chain or branched-chain alkynyl group, straight-chain or branched-chain alkenyl group, substituted or unsubstituted aryl group, substituted or unsubstituted heterocyclic group, or substituted or unsubstituted heteroaryl group;
bond Q represents a single bond or a double bond; and
$R^1$, $R^2$, and $R^3$ are the same or different and represent a hydroxyl group, amino group that may be optionally mono- or di-substituted with a straight-chain or branched-chain alkyl group of one to four carbon atoms, —OL, straight-chain or branched-chain alkyl group, straight-chain or branched-chain alkenyl group, or straight-chain or branched-chain alkynyl group,
wherein L represents a straight-chain or branched-chain alkyl group, straight-chain or branched-chain alkenyl group, or straight-chain or branched-chain alkynyl group;

[5] the pharmaceutical agent of [3], wherein the compound that inhibits the enzyme activity of serine palmitoyltransferase is a compound represented by formula (II) or a derivative thereof:

[6] the pharmaceutical agent of [3], wherein the compound that suppresses expression of serine palmitoyltransferase is (a) or (b):

(a) an RNA complementary to a transcript of a DNA encoding serine palmitoyltransferase, or (b) an RNA with ribozyme activity that specifically cleaves a transcript of a DNA encoding serine palmitoyltransferase;

[7] the pharmaceutical agent of [2], which comprises (a) or (b) as an active ingredient:

(a) a compound that inhibits an activity of dihydrosphingosine-N-acyltransferase, which is involved in dihydroceramide biosynthesis from sphinganine (dihydrosphingosine), or (b) a compound that suppresses expression of dihydrosphingosine-N-acyltransferase of (a);

[8] the pharmaceutical agent of [7], wherein the compound that inhibits the activity of dihydrosphingosine-N-acyltransferase, which is involved in dihydroceramide biosynthesis from sphinganine (dihydrosphingosine), is fumonisin B1 or a derivative thereof;

[9] the pharmaceutical agent of [7], wherein the compound that suppresses expression of dihydrosphingosine-N-acyltransferase is (a) or (b):

(a) an RNA complementary to a transcript of a DNA encoding dihydrosphingosine-N-acyltransferase, or (b) an RNA with ribozyme activity that specifically cleaves a transcript of a DNA encoding dihydrosphingosine-N-acyltransferase;

[10] the pharmaceutical agent of [2], which comprises (a) or (b) as an active ingredient:

(a) a compound that inhibits an enzyme activity of sphingomyelin synthase, which is involved in sphingomyelin biosynthesis from ceramide, or (b) a compound that suppresses expression of the sphingomyelin synthase of (a);

[11] the pharmaceutical agent of [10], wherein the compound that suppresses expression of sphingomyelin synthase is (a) or (b):

(a) an RNA complementary to a transcript of a DNA encoding sphingomyelin synthase, or (b) an RNA with ribozyme activity that specifically cleaves a transcript of a DNA encoding sphingomyelin synthase;

[12] the pharmaceutical agent of any one of [1] to [11], wherein the HCV infection is hepatitis C, liver cirrhosis, liver fibrosis, or liver cancer;

[13] a serine palmitoyltransferase inhibitor which comprises a compound represented by formula (I) or a derivative thereof:

wherein

A represents —(CH$_2$)$_n$—,
wherein n is an integer from 0 to 10;

B represents —CH$_2$—, —(C=O)—, —CH(OH)—, —CH(NH$_2$)—, or —C(=NOR)—,
wherein R represents a hydrogen atom, or a straight-chain or branched-chain alkyl group of one to eight carbon atoms, which can be substituted or unsubstituted with an amino group that may be optionally mono- or di-substituted with a straight-chain or branched-chain alkyl group of one to four carbon atoms;

D represents —(CH$_2$)$_m$—R',
wherein m is an integer from 0 to 10; and

R' represents a hydrogen atom; a straight-chain or branched-chain alkyl group; straight-chain or branched-chain alkynyl group; straight-chain or branched-chain alkenyl group; cycloalkyl group; cycloalkenyl group; substituted or unsubstituted heterocyclic group; substituted or unsubstituted aryl group; substituted or unsubstituted heteroaryl group; —OX group, wherein X denotes a hydrogen atom, or straight-chain or branched-chain alkyl group, straight-chain or branched-chain alkynyl group, straight-chain or branched-chain alkenyl group, cycloalkyl group, or substituted or unsubstituted aryl group; or halogen atom;

E represents a hydrogen atom or a straight-chain or branched-chain alkyl group;

G represents —(CH$_2$)$_p$-J,
wherein p is an integer of 0 to 4; and

J represents a hydrogen atom, OH group, SH group, methylthio group, carboxyl group, carbamoyl group, amino group, guanidino group, straight-chain or branched-chain alkyl group, cycloalkyl group, straight-chain or branched-chain alkynyl group, straight-chain or branched-chain alkenyl group, substituted or unsubstituted aryl group, substituted or unsubstituted heterocyclic group, or substituted or unsubstituted heteroaryl group;

bond Q represents a single bond or a double bond; and

R$^1$, R$^2$, and R$^3$ are the same or different and represent a hydroxyl group, amino group that may be optionally mono- or di-substituted with a straight-chain or branched-chain alkyl group of one to four carbon atoms, —OL, straight-chain or branched-chain alkyl group, straight-chain or branched-chain alkenyl group, or straight-chain or branched-chain alkynyl group, wherein L represents a straight-chain or branched-chain alkyl group, straight-chain or branched-chain alkenyl group, or straight-chain or branched-chain alkynyl group;

[14] a serine palmitoyltransferase inhibitor which comprises a compound represented by formula (II) or a derivative thereof:

(II)

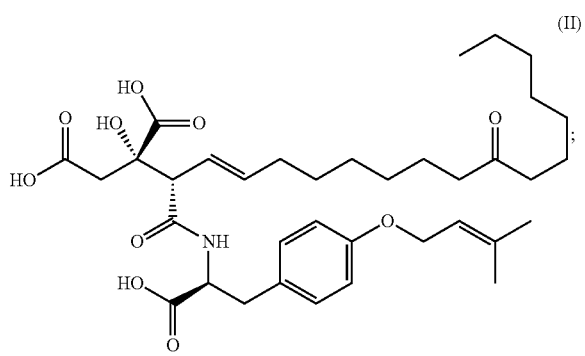

[15] the inhibitor of [13] or [14], which inhibits human-derived serine palmitoyltransferase;

[16] a method of screening for a pharmaceutical agent for treating or preventing an HCV infection, wherein the method comprises the steps of:
(a) contacting an enzyme involved in a process of sphingomyelin biosynthesis with a test compound,
(b) detecting binding between the test compound and the enzyme of (a), and
(c) selecting a test compound that binds to the enzyme of (a);

[17] a method of screening for a pharmaceutical agent for treating or preventing an HCV infection, wherein the method comprises the steps of:
(a) contacting a cell with a test compound,
(b) measuring the amount of a compound synthesized in the process of sphingomyelin biosynthesis, and
(c) selecting as a pharmaceutical agent for treating or preventing an HCV infection, a test compound that reduces the amount of the synthesized compound as compared to that in the absence of contact with the test compound;

[18] a method of screening for a pharmaceutical agent for treating or preventing an HCV infection, wherein the method comprises the steps of:
(a) contacting a cell with a test compound,
(b) measuring the expression level of an enzyme involved in the process of sphingomyelin biosynthesis, and
(c) selecting as a pharmaceutical agent for treating or preventing an HCV infection, a test compound that reduces the expression level of the enzyme as compared to that in the absence of contact with the test compound;

[19] a method of screening for a pharmaceutical agent for treating or preventing an HCV infection, wherein the method comprises the steps of:
(a) providing a cell that comprises a DNA in which a reporter gene is operably linked downstream of a promoter region of a DNA that encodes an enzyme involved in the process of sphingomyelin biosynthesis, or a cell extract thereof,
(b) contacting the cell or cell extract with a test compound,
(c) measuring the expression level of the reporter gene in the cell or cell extract, and
(d) selecting as a pharmaceutical agent for treating or preventing an HCV infection a test compound that reduces expression level of the reporter gene as compared to that in the absence of contact with the test compound;

[20] a method of screening for a pharmaceutical agent for treating or preventing an HCV infection, wherein the method comprises the steps of:
(a) contacting an enzyme involved in the process of sphingomyelin biosynthesis with a test compound,
(b) measuring the activity of the enzyme involved in the process of sphingomyelin biosynthesis, and
(c) selecting as a pharmaceutical agent for treating or preventing an HCV infection, a test compound that reduces the activity of the enzyme as compared to that in the absence of contact with the test compound;

[21] the screening method of any one of [16] to [20], wherein the process of sphingomyelin biosynthesis is the process of sphingomyelin biosynthesis from palmitoyl CoA;

[22] the screening method of [21], wherein the process of sphingomyelin biosynthesis from palmitoyl CoA involves the enzymes serine palmitoyltransferase, N-acyltransferase, and sphingomyelin synthase;

[23] the screening method of any one of [16] to [22], wherein the HCV infection is hepatitis C, liver cirrhosis, liver fibrosis, or liver cancer; and

[24] a kit for use in the screening method of any one of [16] to [23].

BRIEF DESCRIPTION OF THE DRAWINGS

FIG. 7 shows the inhibition of serine palmitoyltransferase (LCB1) protein expression by siRNAs.

DETAILED DESCRIPTION

The present invention relates to pharmaceutical agents for treating or preventing HCV infections that comprise as active ingredients compounds that block a process of sphingomyelin biosynthesis.

Figure 1:
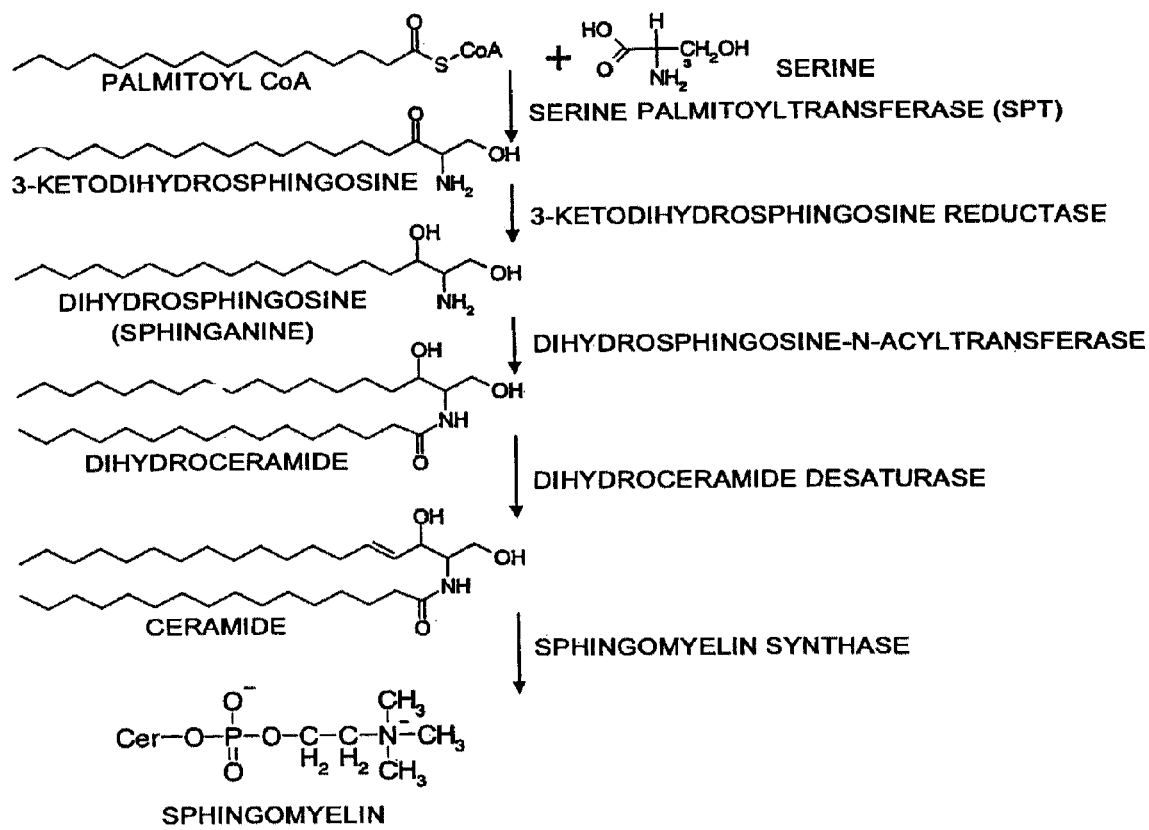
FIG. 1 shows the sphingolipid biosynthesis pathway (the synthetic pathway from palmitoyl CoA to sphingomyelin).

Examples of a process of sphingomyelin biosynthesis in the present invention include the process of sphingomyelin biosynthesis from palmitoyl CoA (FIG. 1).

In the present invention, the compounds that block a process of sphingomyelin biosynthesis may be any compounds, so long as they directly or indirectly inhibit an in vivo reaction involved in the process of sphingomyelin biosynthesis from palmitoyl CoA. Such compounds may be compounds that inhibit the activity of an enzyme involved in the process of sphingomyelin biosynthesis, compounds that inhibit the expression of an enzyme involved in the biosynthesis, or compounds that indirectly inhibit an enzyme involved in the biosynthesis, which are compounds that produce or increase the amount of such inhibitors.

In the present invention, examples of enzymes involved in the process of sphingomyelin biosynthesis include serine palmitoyltransferase, 3-ketodihydrosphingosine reductase, dihydrosphingosine-N-acyltransferase, dihydroceramide desaturase, and sphingomyelin synthase (FIG. 1), and can preferably include serine palmitoyltransferase, dihydrosphingosine-N-acyltransferase, and sphingomyelin synthase.

Examples of the compounds of the present invention include compounds that block the process of 3-ketodihydrosphingosine biosynthesis from palmitoyl CoA, which is an early step in the process of sphingolipid biosynthesis. Examples of such compounds that block this biosynthetic process are compounds that inhibit the enzyme activity of serine palmitoyltransferase, which is involved in the biosynthesis, or compounds that suppress the expression of serine palmitoyltransferase.

Compounds of the present invention that inhibit the enzyme activity of serine palmitoyltransferase may be any compounds so long as they inhibit the enzyme activity, but preferable examples include sphingofungin, myriocin, compounds represented by formula (I), or derivatives thereof:

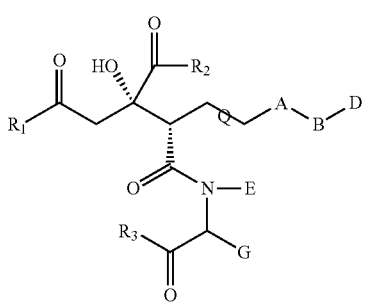

Formula (I)

wherein
A represents —(CH$_2$)$_n$—,
wherein n is an integer from 0 to 10;
B represents —CH$_2$—, —(C═O)—, —CH(OH)—, —CH(NH$_2$)—, or —C(═NOR)—,
wherein R represents a hydrogen atom, or a straight-chain or branched-chain alkyl group of one to eight carbon atoms, which can be substituted or unsubstituted with an amino group that may be optionally mono- or di-substituted with a straight-chain or branched-chain alkyl group of one to four carbon atoms;
D represents —(CH$_2$)$_m$—R',
wherein m is an integer from 0 to 10, and
R' represents a hydrogen atom, straight-chain or branched-chain alkyl group, straight-chain or branched-chain alkynyl group, straight-chain or branched-chain alkenyl group, cycloalkyl group, substituted or unsubstituted heterocyclic group, substituted or unsubstituted aryl group, substituted or unsubstituted heteroaryl group, —OX group (wherein X denotes a hydrogen atom, or straight-chain or branched-chain alkyl group, straight-chain or branched-chain alkynyl group, straight-chain or branched-chain alkenyl group, cycloalkyl group, or substituted or unsubstituted aryl group), or halogen atom;
E represents a hydrogen atom or a straight-chain or branched-chain alkyl group;
G represents —(CH$_2$)$_p$-J,
wherein p is an integer of 0 to 4, and
J represents a hydrogen atom, OH group, SH group, methylthio group, carboxyl group, carbamoyl group, amino group, guanidino group, straight-chain or branched-chain alkyl group, cycloalkyl group, straight-chain or branched-chain alkynyl group, straight-chain or branched-chain alkenyl group, substituted or unsubstituted aryl group, substituted or unsubstituted heterocyclic group, or substituted or unsubstituted heteroaryl group;
bond Q represents a single bond or a double bond; and
R$^1$, R$^2$, and R$^3$ are the same or different groups and represent a hydroxyl group, amino group that may be optionally mono- or di-substituted with a straight-chain or branched-chain alkyl group of one to four carbon atoms, —OL, straight-chain or branched-chain alkyl group, straight-chain or branched-chain alkenyl group, or straight-chain or branched-chain alkynyl group,
wherein L represents a straight-chain or branched-chain alkyl group, straight-chain or branched-chain alkenyl group, or straight-chain or branched-chain alkynyl group.

In the present invention, unless specifically defined herein, "straight-chain or branched-chain alkyl group" means a straight-chain or branched-chain hydrocarbon group of one to twelve carbons, and preferably means a straight-chain or branched-chain hydrocarbon group of one to seven carbons. Examples include a methyl group, ethyl group, propyl group, isopropyl group, n-butyl group, isobutyl group, t-butyl group, pentyl group, and heptyl group. "Cycloalkyl group" means a cyclic hydrocarbon group of three to eight carbons. Examples include a cyclopentyl group, cyclohexyl group, cycloheptyl group, and cyclohexenyl group. "Straight-chain or branched-chain alkenyl group" means a straight-chain or branched-chain hydrocarbon group of two to eight carbons, which comprises at least one double bond. Examples include a vinyl group, 1-propenyl group, allyl group, 2-butenyl group, and 2-ethenyl-2-butenyl group. "Straight-chain or branched-chain alkynyl group" means a straight-chain or branched-chain hydrocarbon group of two to eight carbons, which comprises at least one triple bond. Examples include an ethynyl group, 1-propynyl group, 2-propynyl group, 1-butynyl group, 3-butynyl group, 2-pentynyl group, 3-pentynyl group, 4-pentynyl group, 2-hexynyl group, 4-hexynyl group, 2-decynyl group, and 6,6-dimethyl-hepta-2,4-diyn-1-yl group.

The "heterocyclic group" described herein means a four to sixmembered monocyclic or seven to tenmembered bicyclic group (preferably a monocyclic group), which comprises one to four (preferably one or two) heteroatoms that are individually selected from among nitrogen, sulfur, and oxygen atoms as members of the ring, and may comprise at least one double bond. Specific examples are groups derived from pyran, morpholine, tetrahydrofuran, dihydrofuran, tetrahydropyran, dihydropyran, 1,3-dioxane, piperazine, piperidine, thiomorpholine, and such.

The "aryl group" described herein means a monocyclic or polycyclic hydrocarbon group that has aromaticity. Specific examples include groups derived from benzene, naphthalene, anthracene, and fluorene.

The "heteroaryl group" described herein means a four to six-membered monocyclic or seven to tenmembered bicyclic group (preferably a monocyclic group) which has aromaticity, and comprises one to four (preferably one or two) heteroatoms that are individually selected from among nitrogen, sulfur, and oxygen atoms as members of the ring. Specific examples include groups derived from furan, thiophene, pyrrole, diazole, pyridine, thiazole, imidazole, pyrimidine, indole, quinoline, oxazole, isoxazole, pyrazine, triazole, thiadiazole, tetrazole, and pyrazole.

The "aralkyl group" described herein means the above-mentioned straight-chain or branched-chain alkyl group substituted with the above-mentioned aryl group, and specific examples include a benzyl group and a phenethyl group.

The "heteroarylalkyl group" described herein means the above-mentioned straight-chain or branched-chain alkyl group substituted with the above-mentioned heteroaryl group.

The "acyl group" described herein means the above-mentioned straight-chain or branched-chain alkyl group, aryl group, heteroaryl group, or heterocyclic group that is bonded via a carbonyl group.

The phrase "substituted or unsubstituted" described herein, unless particularly defined herein, means that a group may be optionally substituted with a group such as a straight-chain or branched-chain alkyl group, straight-chain or branched-chain alkoxy group, straight-chain or branched-chain alkenyl group, straight-chain or branched-chain alkenyloxy group, straight-chain or branched-chain alkynyl group, straight-chain or branched-chain alkynyloxy group, cycloalkyl group, cycloalkyloxy group, cyano group, nitro group, trifluoromethyl group, trifluoromethoxy group, halogen atom, aryl group, aryloxy group, heteroaryl group, heteroaryloxy group, aralkyl group, aralkyloxy group, amino group (which may be optionally mono- or di-substituted with a straight-chain or branched-chain alkyl group), acyl group, straight-chain or branched-chain alkylsulfonyl group, carbamoyl group, straight-chain or branched-chain alkylthio group, carboxyl group, straight-chain or branched-chain alkylcarbonyl group, formyl group, and aminosulfonyl group. The aryl and heteroaryl moieties included in these substituent groups may be further optionally mono-, di-, or tri-substituted with a halogen atom, straight-chain or branched-chain alkyl group, straight-chain or branched-chain alkoxy group, straight-chain or branched-chain alkenyl group, straight-chain or branched-chain alkenyloxy group, straight-chain or branched-chain alkynyl group, straight-chain or branched-chain alkynyloxy group, cycloalkyl group, cycloalkyloxy group, cyano group, nitro group, trifluoromethyl group, trifluoromethoxy group, halogen atom, aryl group, aryloxy group, heteroaryl group, aralkyl group, aralkyloxy group, amino group that may be optionally mono- or di-substituted with a straight-chain or branched-chain alkyl group, acyl group, straight-chain or branched-chain alkylsulfonyl group, straight-chain or branched-chain alkoxy group, carbamoyl group, straight-chain or branched-chain alkylthio group, carboxyl group, straight-chain or branched-chain alkylcarbonyl group, formyl group, aminosulfonyl group, and such.

Preferred examples of the compounds of formula (I) of the present invention are the following:

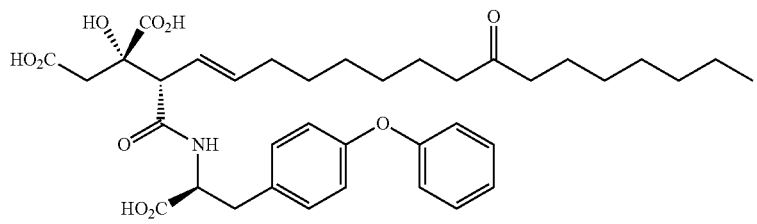

(1)

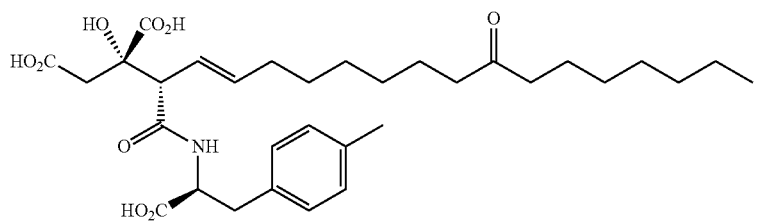

(2)

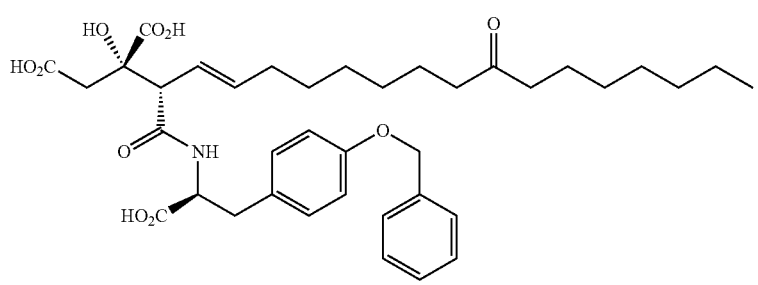

(3)

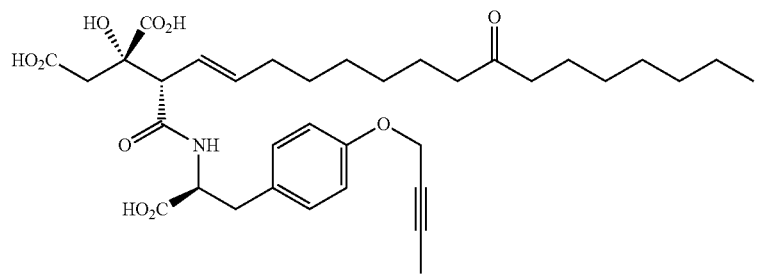
(4)
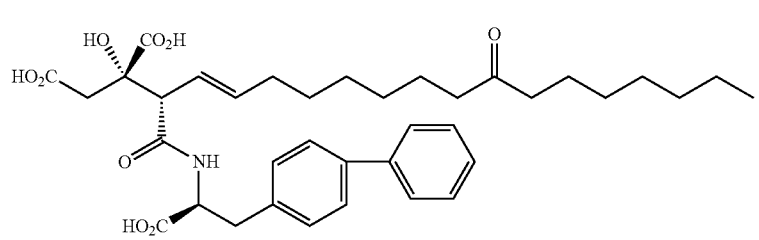
(5)
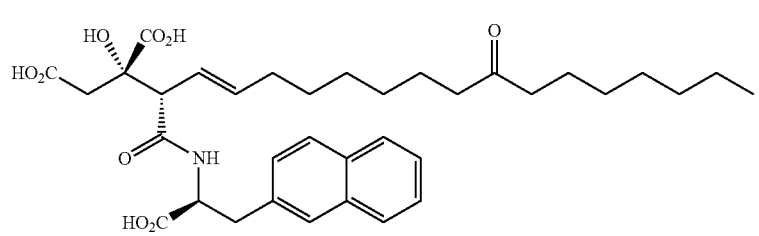
(6)
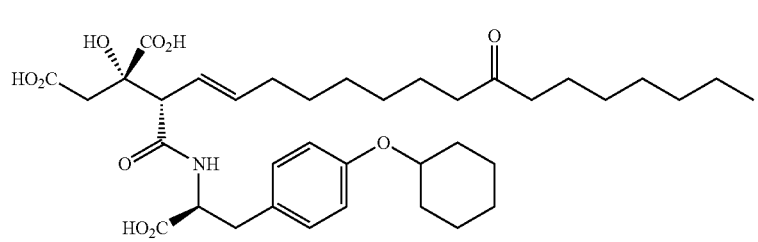
(7)
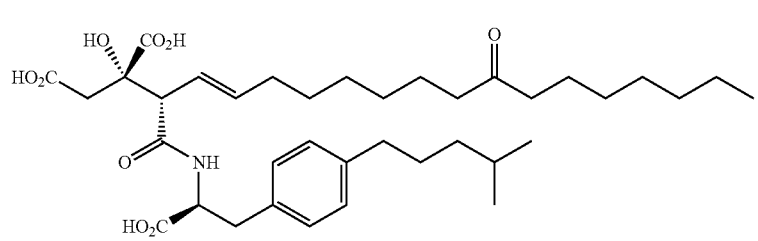
(8)
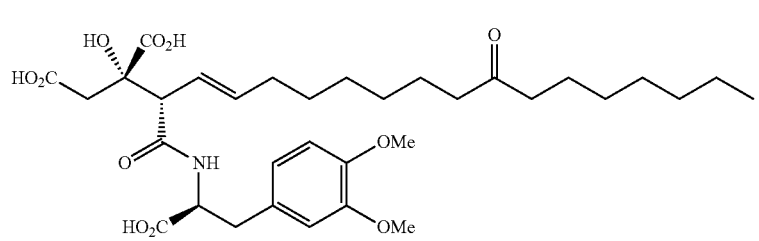
(9)

-continued
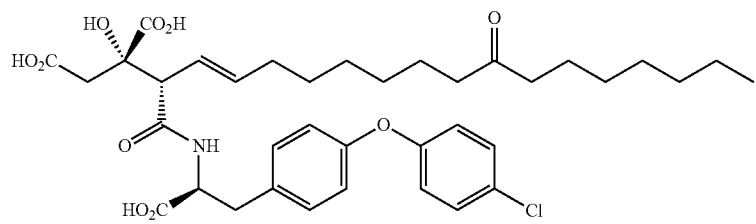
(10)
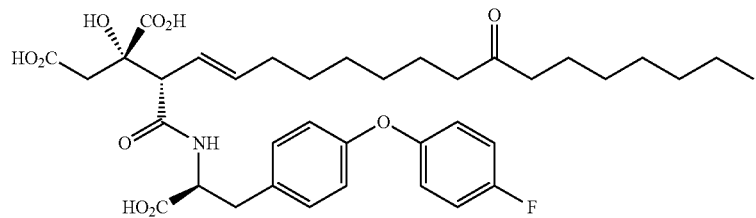
(11)
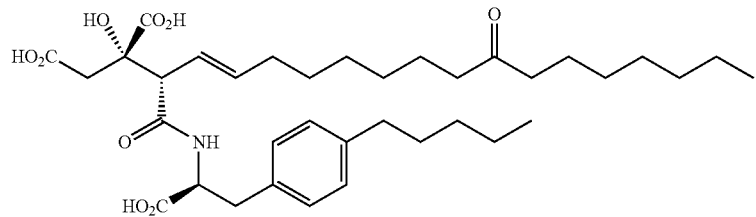
(12)
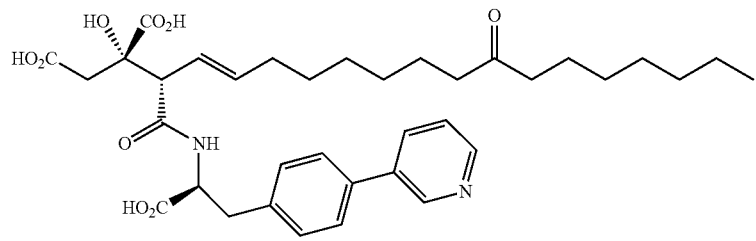
(13)
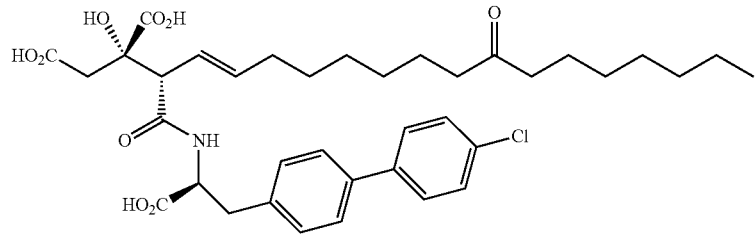
(14)
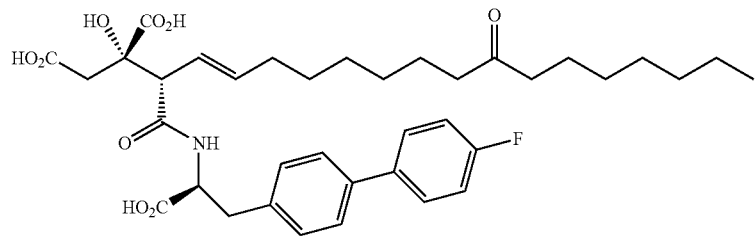
(15)

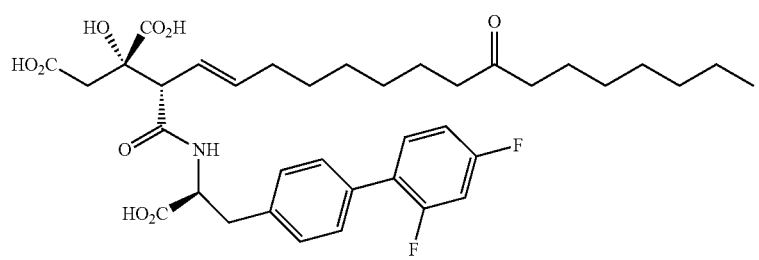
(16)
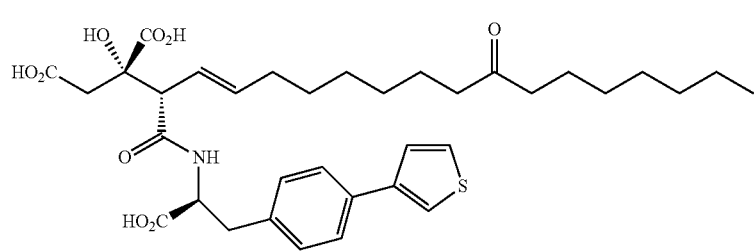
(17)
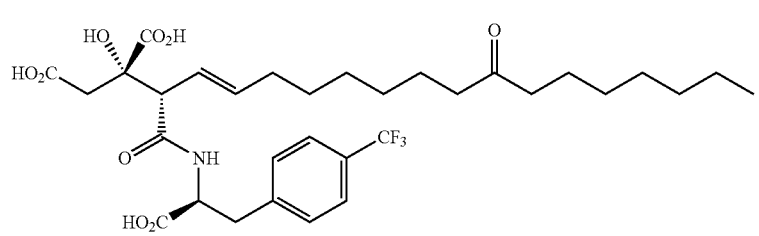
(18)
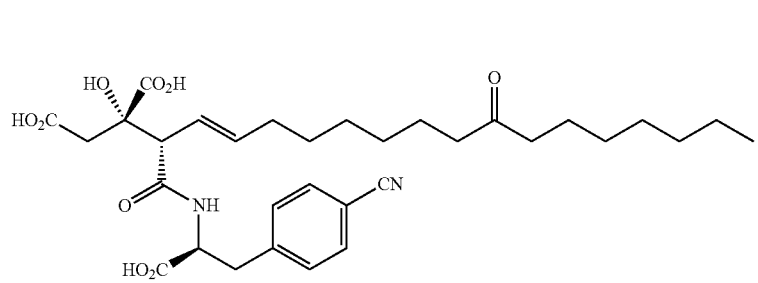
(19)
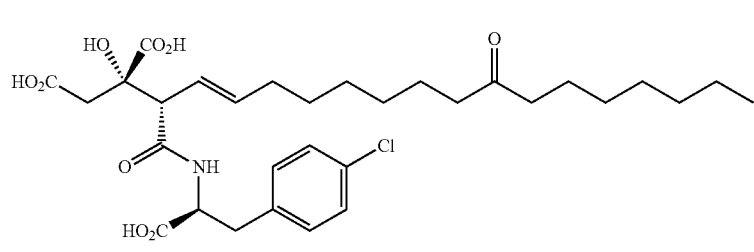
(20)
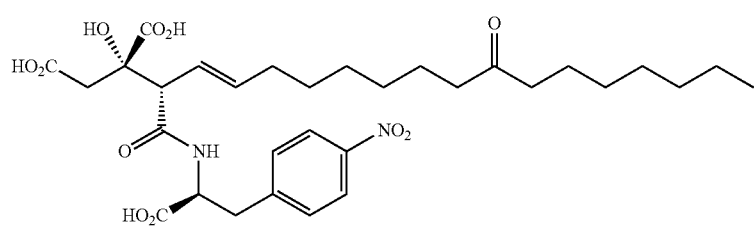
(21)

-continued
(22)
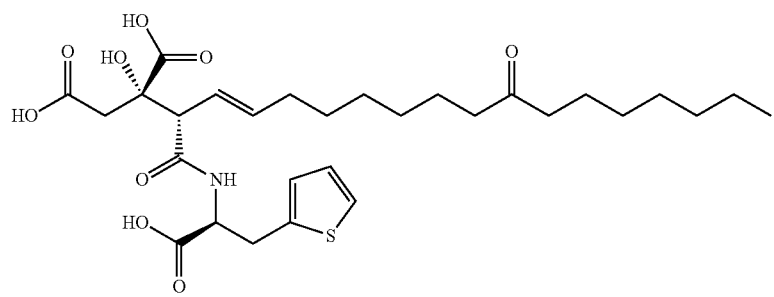
(23)
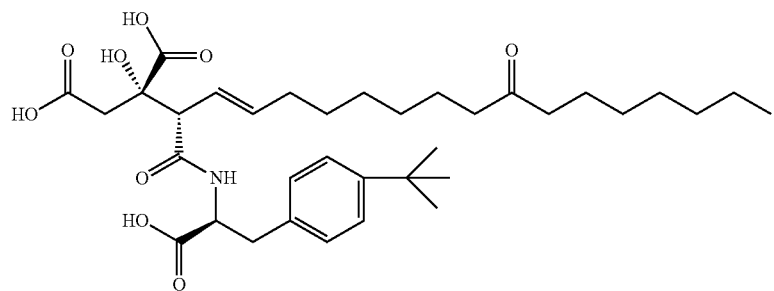
(24)
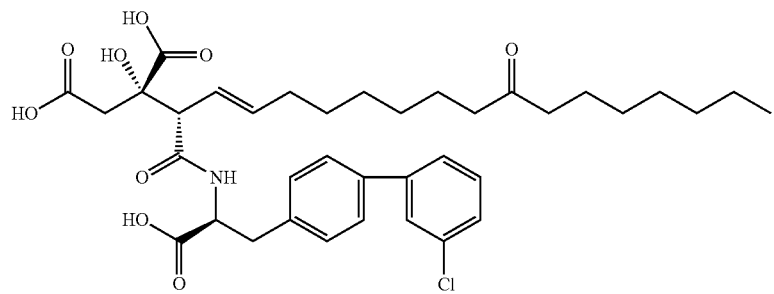
(25)
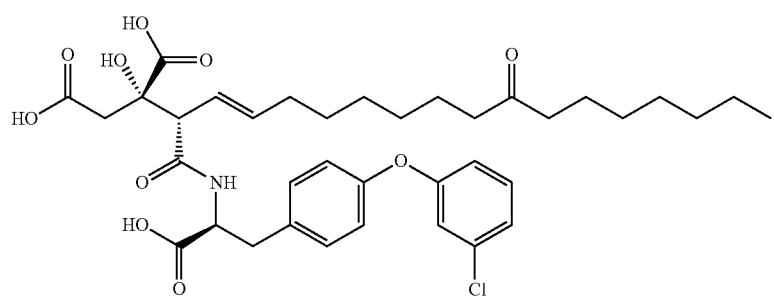
(26)
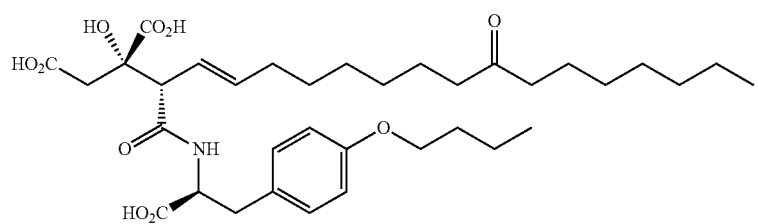
(27)
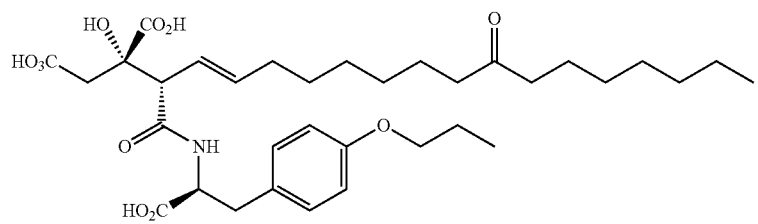

-continued
(28)
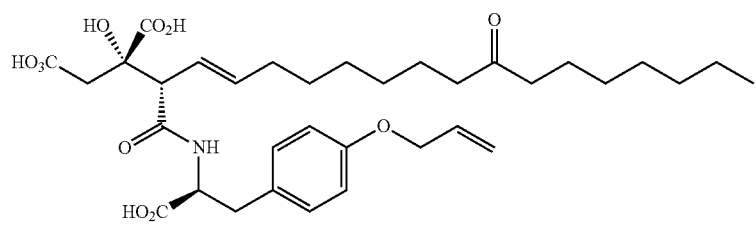
(29)
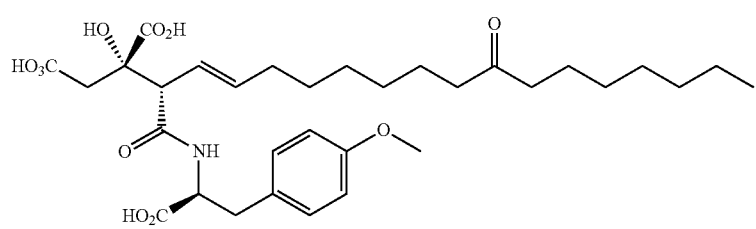
(30)
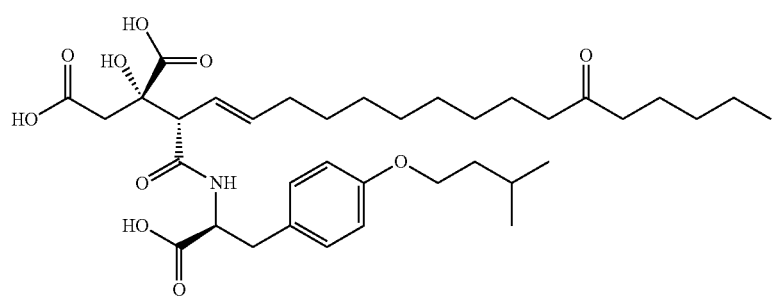
(31)
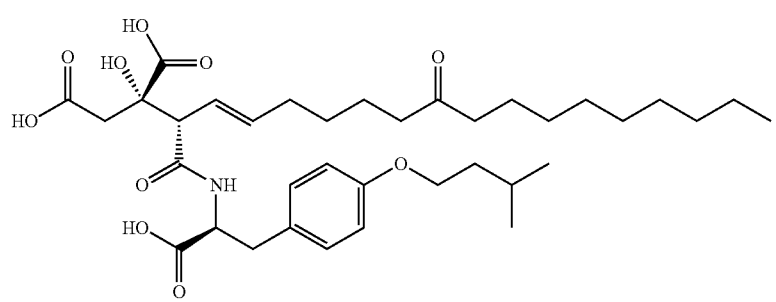
(32)
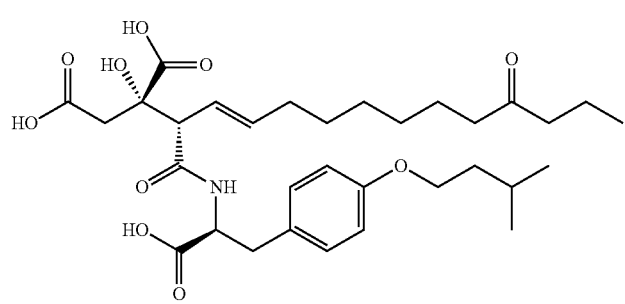
(33)
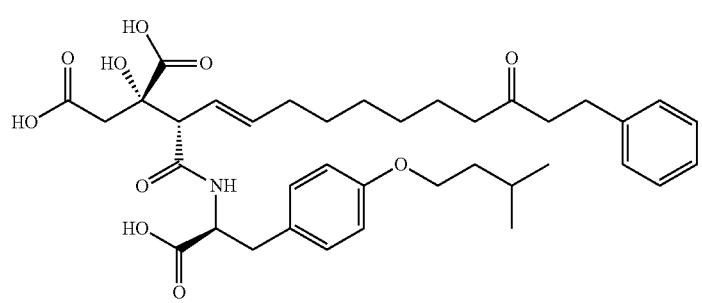

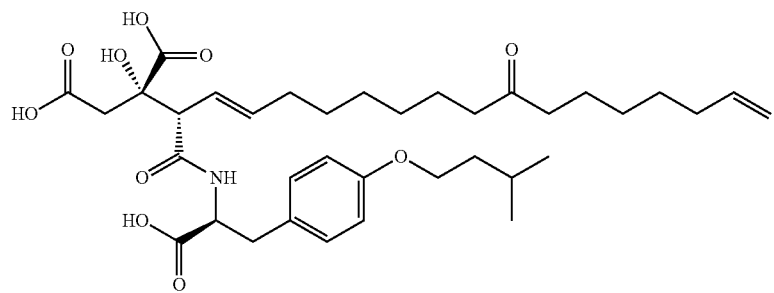
(34)
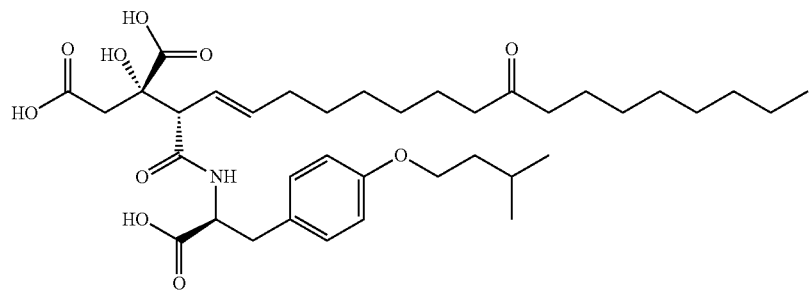
(35)
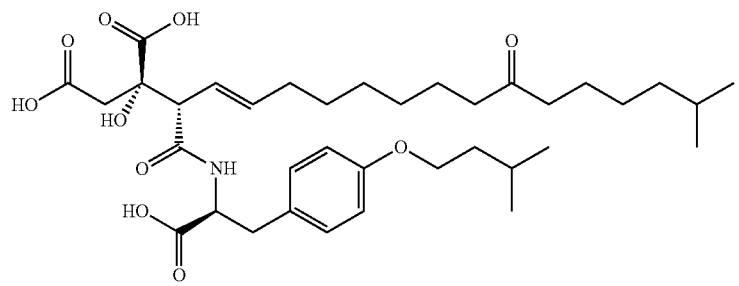
(36)
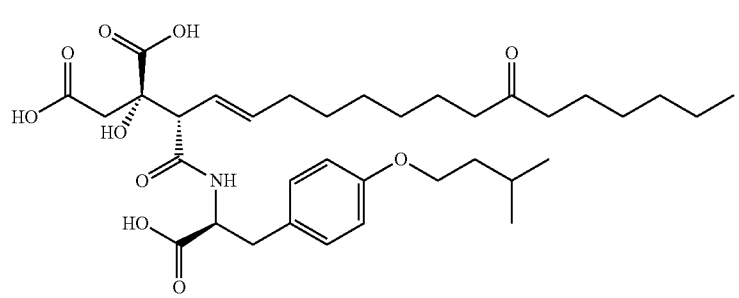
(37)
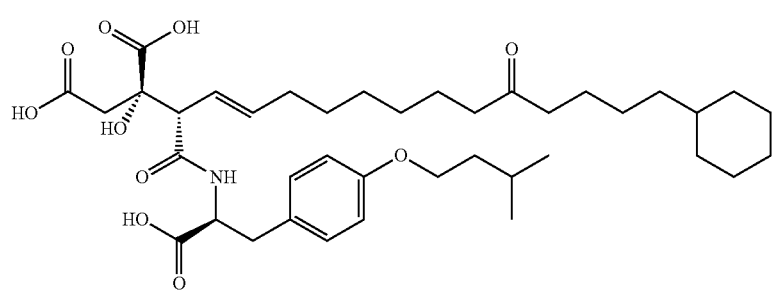
(38)

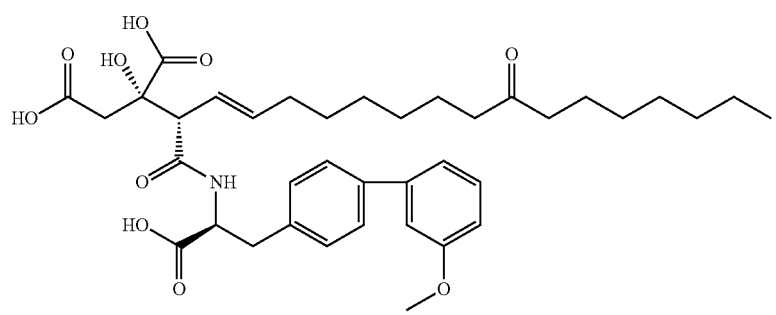
(39)
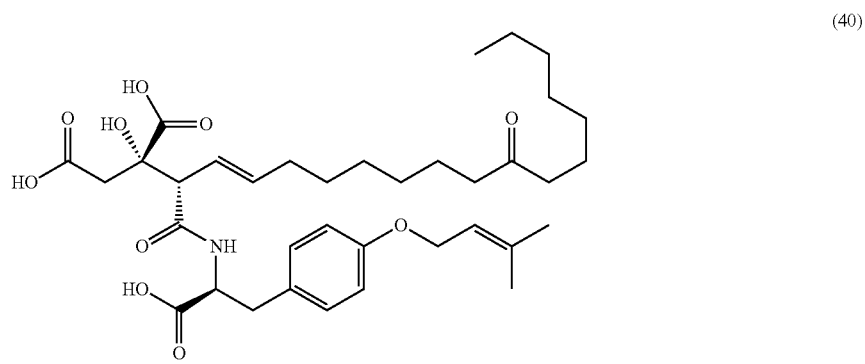
(40)
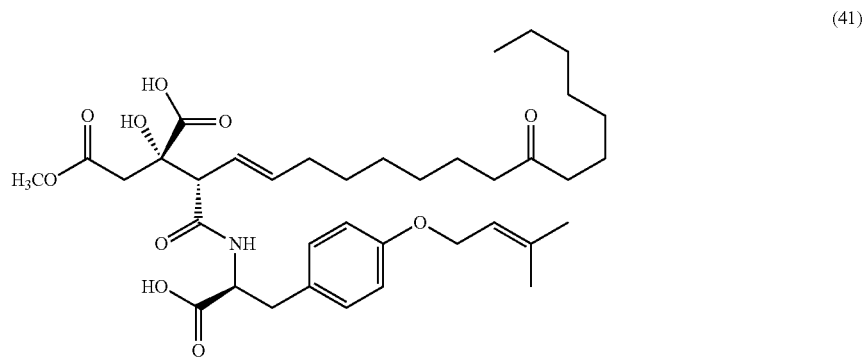
(41)
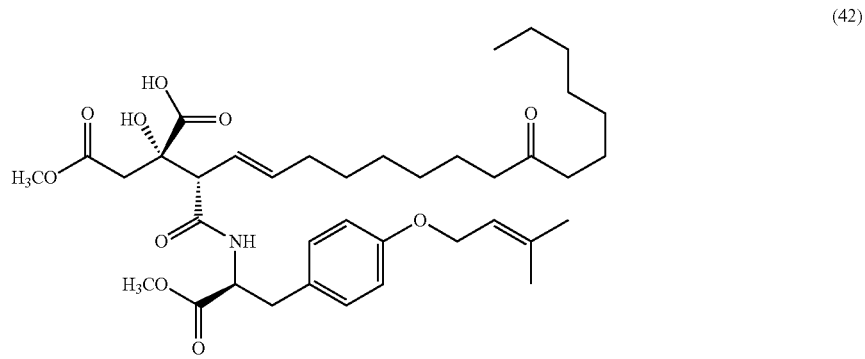
(42)

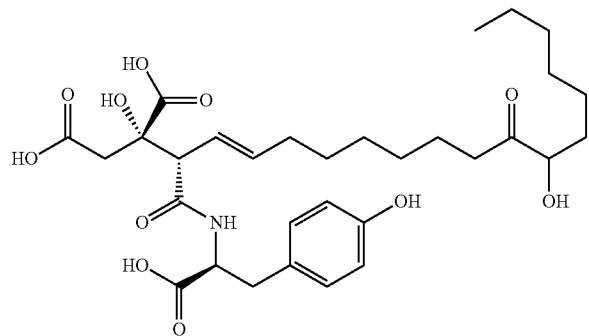
(43)
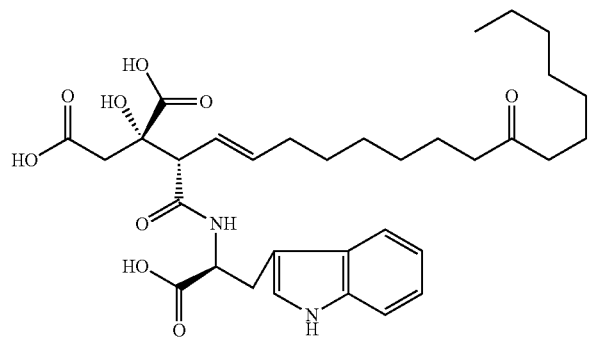
(44)
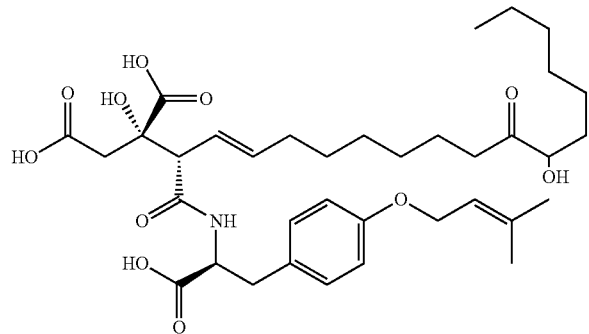
(45)
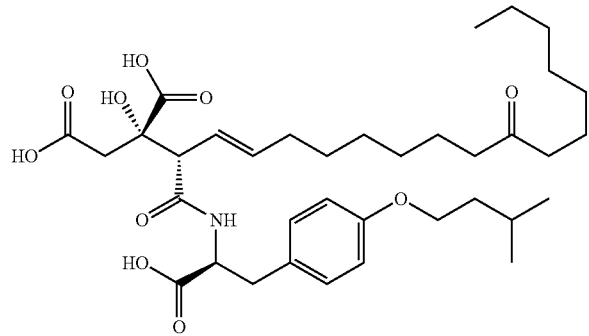
(46)

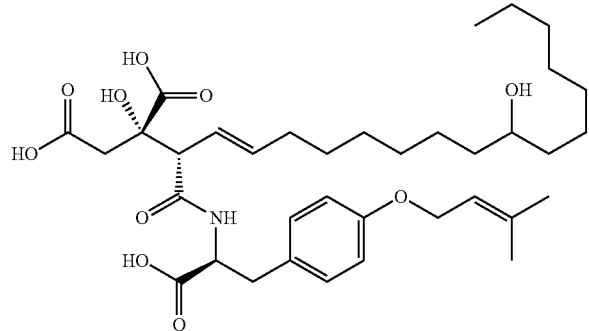
(47)
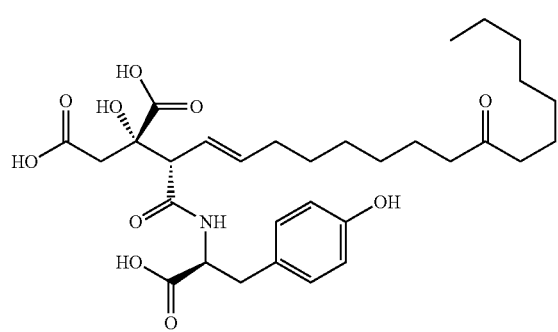
(48)
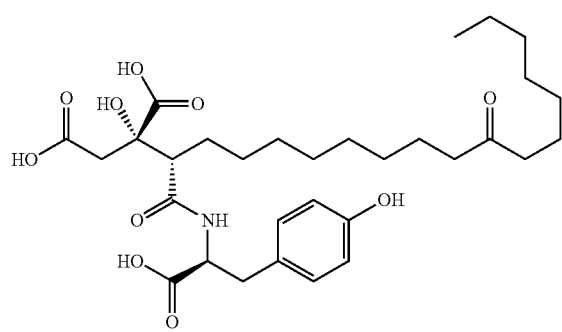
(49)
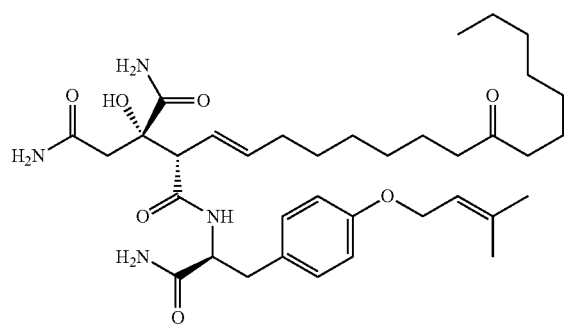
(50)
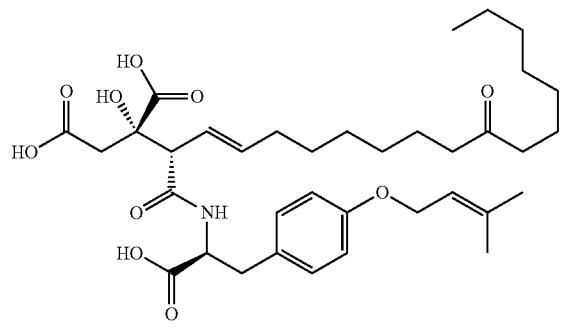
(51)

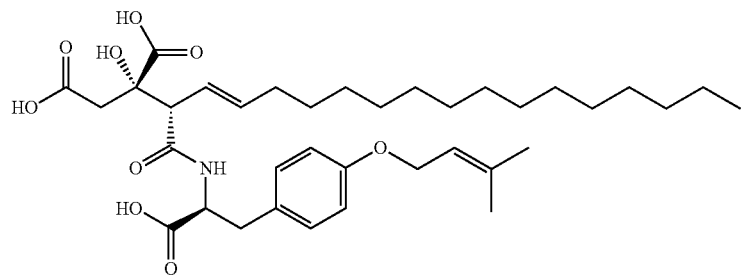
(52)
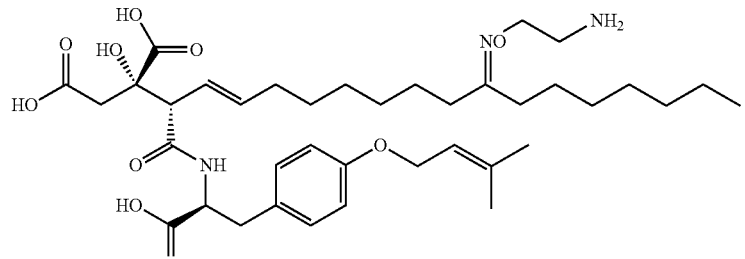
(53)
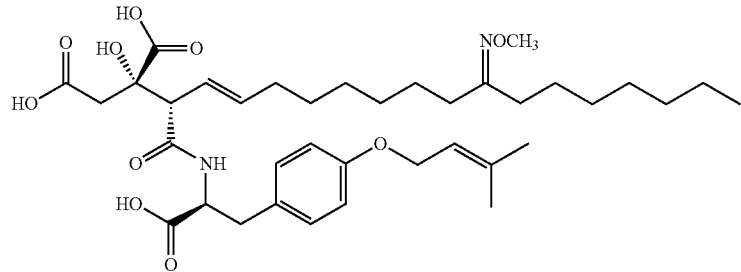
(54)
An example of the methods of the present invention for synthesizing the compounds of formula (I) is described by the following reaction scheme:
Procedure 1
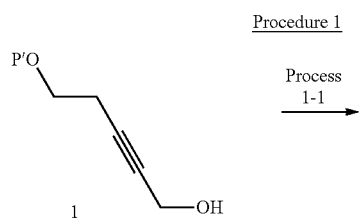
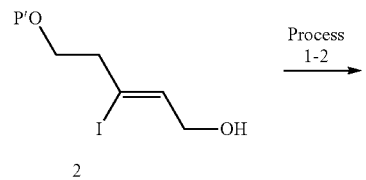
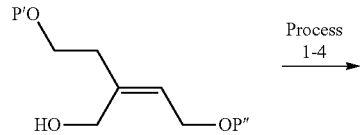
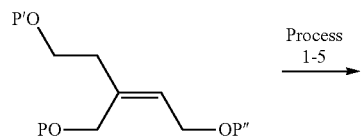

-continued

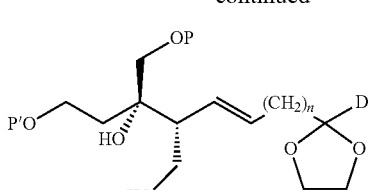

8

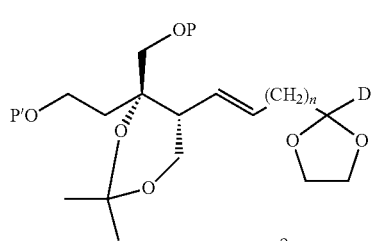

9

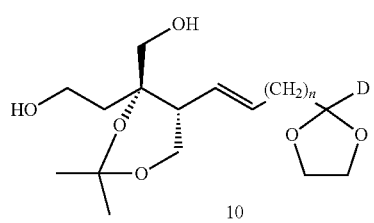

10

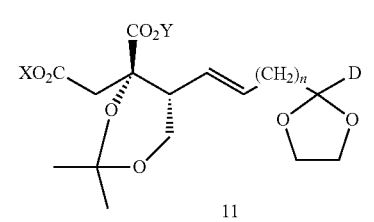

11

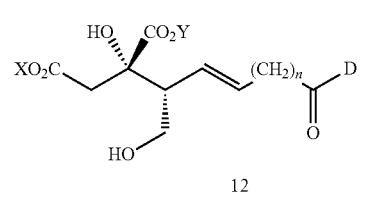

12

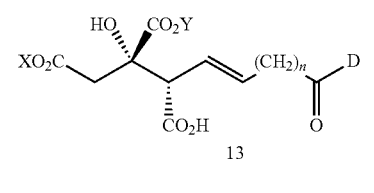

13

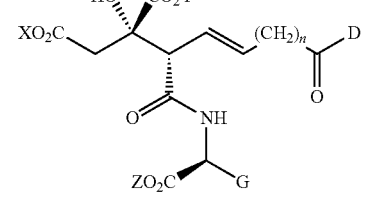

14-A

Process 1-8 →

Process 1-9 →

Process 1-10 →

Process 1-11 →

Process 1-12 →

Process 1-13 →

Process 1-14 →

-continued

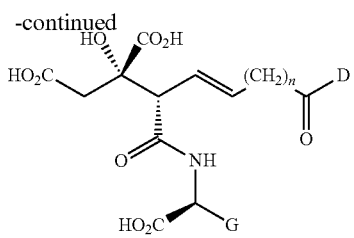

14-B

In the formulas shown above, each of the symbols has the same meaning as indicated in formula (I) described above, and P, P', and P'" indicate hydroxy protecting groups. Compound 1, which is the starting compound, can be synthesized according to a method described in the literature (B. E. Marron, et al., J. Org. Chem. 1989, 45, 5522).

Process 1-1

Compound 2 can be obtained by reacting compound 1 with a reducing agent such as sodium bis(2-methoxyethoxy) aluminum hydride or lithium aluminum hydride, in a solvent such as various types of ethers including diethylether, tetrahydrofuran, and dioxane, benzene, toluene, or cyclohexane, or in a mixed solvent thereof, at room temperature or while cooling, preferably on ice, and then subsequently treating with iodine while cooling, preferably at −78° C.

Process 1-2

Compound 3 can be obtained by reacting compound 2 with dihydropyran in a solvent such as diethylether, toluene, cyclohexane, methylene chloride, chloroform, 1,2-dichloroethane, ethylacetate, or in a mixed solvent thereof in the presence of a catalytic amount of an acid such as pyridinium p-toluenesulfonate, toluenesulfonic acid, methanesulfonic acid, acetic acid, trifluoroacetic acid, or dilute hydrochloric acid, at room temperature or while cooling, preferably on ice.

Process 1-3

Compound 4 can be obtained by reacting compound 3 with a strong base such as tert-butyl lithium, n-butyl lithium, or sec-butyl lithium, in a solvent such as various types of ethers including diethylether, tetrahydrofuran, and dioxane, benzene, toluene, or cyclohexane, or in a mixed solvent thereof, at room temperature or while cooling, preferably at −78° C., and then further adding formaldehyde and reacting the mixture while cooling, preferably on ice.

Process 1-4

Compound 5 can be obtained by reacting compound 4 with tert-butyldiphenylchlorosilane in a solvent such as N,N-dimethylformamide, tetrahydrofuran, methylene chloride, or chloroform, or in a mixed solvent thereof, in the presence of a base such as imidazole, trimethylamine, or pyridine at room temperature or while cooling, preferably on ice.

Process 1-5

Compound 6 can be obtained by reacting compound 5 in various alcoholic solvents such as ethanol, methanol, and propanol, in the presence of a catalytic amount of an acid such as pyridinium p-toluenesulfonate, toluenesulfonic acid, methanesulfonic acid, acetic acid, trifluoroacetic acid, or dilute hydrochloric acid, at room temperature or while heating, and preferably heating under reflux.

Process 1-6

Compound 7 can be obtained by reacting compound 6 with a peroxide such as tert-butylhydroperoxide or cumene hydroperoxide in a solvent such as methylene chloride or chloroform, or in a mixed solvent thereof, in the presence of a Lewis acid such as titanium tetraisopropoxide or titanium tetrabutyloxide, and in the presence of L-(+)-diethyl tartrate or L-(+)-dipropyl tartrate, or D-(−)-diethyl tartrate or D-(−)-dipropyl tartrate, at room temperature or while cooling, but preferably while cooling.

Process 1-7

Compound 8 can be obtained by reacting compound 7 with a vinyl metal derivative that can be obtained by performing hydrometallation (for example, hydrozirconation or hydroboration) on the triple bond of a compound represented by the formula

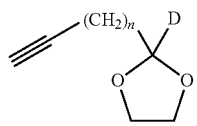

that is synthesized according to the following Procedure 2, and comprises a desired chain A (—$(CH_2)_n$—) and group D, and then performing a transmetallation (for example by using a Grignard reagent, dialkyl zinc, or such), in a solvent such as various kinds of ethers including diethylether, tetrahydrofuran, and dioxane, benzene, toluene, or cyclohexane, or in a mixed solvent thereof, at room temperature or while cooling, but preferably at −78° C.

Process 1-8

Compound 9 can be obtained by reacting compound 8 with 2,2-dimethoxypropane or acetone in a solvent such as diethyl ether, toluene, hexane, methylene chloride, chloroform, or 1,2-dichloroethane, or in a mixed solvent thereof, in the presence of a catalytic amount of an acid such as pyridinium p-toluenesulfonate, toluenesulfonic acid, methanesulfonic acid, acetic acid, trifluoroacetic acid, hydrochloric acid, or sulfuric acid at room temperature or while cooling, but preferably at room temperature.

Process 1-9

Compound 10 can be obtained by reacting compound 9 in a solvent such as diethyl ether, tetrahydrofuran, hexane, methylene chloride, or chloroform, or in a mixed solvent thereof, in the presence of tetrabutylammonium fluoride, hydrogen fluoride, acetic acid, or dilute hydrochloric acid, at room temperature or while cooling.

Process 1-10

A corresponding dicarboxylic acid can be obtained by oxidizing compound 10 using manganese peroxide, nitric acid, Jones reagent, or such. Alternatively, the corresponding dialdehyde can be obtained by oxidating compound 10 using potassium permanganate, Swern oxidation, Collins oxidation, TEMPO oxidation, or such. Preferably, a dialdehyde can be obtained by reacting compound 10 in a solvent such as methylene chloride or chloroform, in the presence of oxalyl chloride and dimethylsulfoxide, while cooling preferably at −78° C., followed by treatment with a base such as triethylamine. The obtained product can be subsequently treated with an oxidizing agent such as potassium permanganate, sodium chlorite, or chromic acid, to produce a dicarboxylic acid. Preferably, a dicarboxylic acid can be obtained by reaction with an aqueous solution of sodium chlorite and sodium dihydrogen phosphate in 2-methyl-2-propanol and 2-methyl-2-butene, at room temperature or while cooling, but preferably while cooling. The obtained product can be subsequently reacted in N,N-dimethylformamide di-tert-butyl acetal or with 2,2,2-trichloroacetoimidate tert-butyl at room temperature or while heating in a solvent such as N,N-dimethylformamide, diethyl ether, tetrahydrofuran, hexane, methylene chloride, or chloroform, or in a mixed solvent thereof, or without solvent to obtain compound 11.

Process 1-11

Compound 12 can be obtained by reacting compound 11 in a solvent such as tetrahydrofuran or dioxane, or in a mixed solvent thereof, in the presence of water, and in the presence of an acid such as pyridinium-p-toluenesulfonate, methane sulfonic acid, or acetic acid, at room temperature or while cooling, but preferably at room temperature.

Process 1-12

Compound 12 can be converted to a corresponding dicarboxylic acid by an oxidation reaction using manganese peroxide, nitric acid, Jones reagent, or such. Preferably, compound 13 can be obtained by reacting compound 12 with Jones reagent in acetone at room temperature or while cooling, but preferably while cooling.

Process 1-13

Compound 14-A, which is an embodiment of compounds of formula (I), can be obtained by reacting compound 13 with an α-amino acid tert-butyl ester hydrochloride in a solvent such as N,N-dimethylformamide, tetrahydrofuran, diethyl ether, methylene chloride, or chloroform, or in a mixed solvent thereof, in the presence of a base such as N,N-diisopropylethylamine, triethylamine, pyridine, or 4-N,N-dimethylaminopyridine, using a coupling reagent such as O-(7-azabenzotriazol-1-yl)-N,N,N',N'-tetramethyluroniumhexafluorophosphate, water soluble carbodiimide hydrochloride (WSC.HCl), or 1-hydroxybenzotriazole (HOBt), at room temperature or while cooling, but preferably at room temperature.

Process 1-14

Compound 14-B, which is an embodiment of the compounds of formula (I), can be obtained by reacting compound 14-A in a solvent such as ethyl ether, tetrahydrofuran, dioxane, hexane, methylene chloride, chloroform, ethyl acetate, or water, or in a mixed solvent thereof, in the presence or absence of anisole, and in the presence of an acid such as methanesulfonic acid, acetic acid, trifluoroacetic acid, or dilute hydrochloric acid, at room temperature or while cooling, but preferably at room temperature.

Among the compounds of formula (I) of the present invention, compounds other than compounds 14-A and 14-B described above can be obtained by starting from compound 14-A or 14-B and subjecting it to hydrolysis, reduction, amination or amidation, hydroxyimination, and/or esterification as necessary, depending on the desired compound of formula (I). Compounds of formula (I) in which bond Q is a single bond can also be obtained by hydrogenating compound 14-A or 14-B in a solvent such as methanol, ethanol, ethyl acetate, or tetrahydrofuran in the presence of a catalyst such as palladium-carbon, palladium hydroxide, Raney nickel, or platinum oxide, at room temperature or while heating.

A compound represented by the formula:

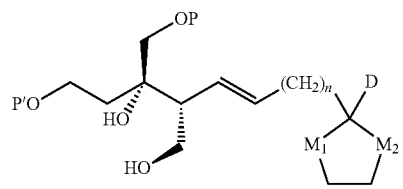

wherein, D and n have the same meaning as described above, $M_1$ and $M_2$ are the same or different and represent an oxygen atom or a sulfur atom, and P and P' are the same or different and represent hydroxyl protecting groups;
which is a useful intermediate compound for synthesizing the compounds of formula (I), can be synthesized by reacting a compound represented by the formula:

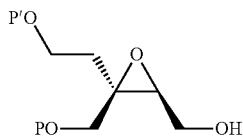

wherein, P and P' have the same meaning as described above;
with the compound represented by the formula:

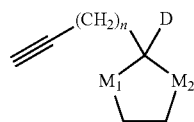

wherein, D, n, $M_1$, and $M_2$ have the same meaning as described above. This method corresponds to the aforementioned method of Process 1-7 in Procedure 1.

The compound of formula:

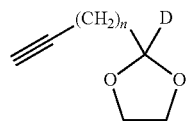

which is one of the intermediate compounds for synthesizing the above-mentioned compounds of formula (I), can be synthesized according to the following reaction scheme.

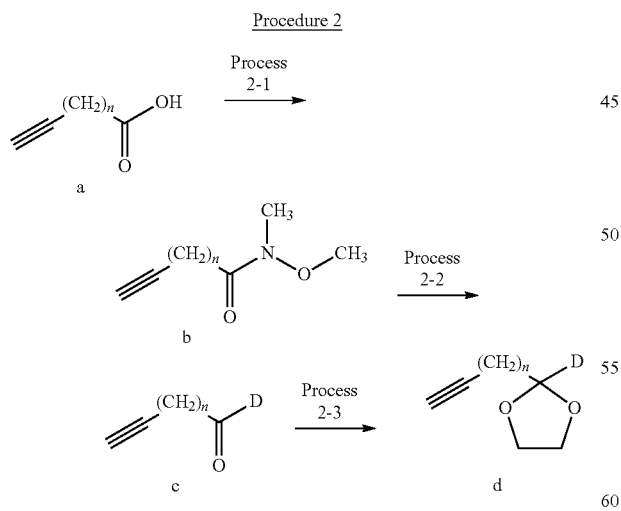

Process 2-1
Compound b can be obtained by reacting compound a, which comprises a terminal triple bond and a desired chain A (—$(CH_2)_n$—), with N,O-dimethylhydroxylamine hydrochloride in a solvent such as diethyl ether, tetrahydrofuran, dioxane, hexane, methylene chloride, chloroform, or ethyl acetate, or in a mixed solvent thereof, in the presence of a base such as N,N-diisopropylethylamine, triethylamine, pyridine, or 4-N,N-dimethylaminopyridine, using a coupling reagent such as O-(7-azabenzotriazol-1-yl)-N,N,N',N'-tetramethyluroniumhexafluorophosphate, water soluble carbodiimide hydrochloride (WSC.HCl), or 1-hydroxybenzotriazole (HOBt), at room temperature.

Process 2-2
Compound c that has been introduced with group D can be obtained by reacting compound b obtained in the above-mentioned process, with a Grignard reagent or alkyl lithium reagent carrying the desired group D in a solvent such as diethyl ether, tetrahydrofuran, dioxane, or hexane, or in a mixed solvent thereof, at room temperature or while cooling, but preferably while cooling.

Process 2-3
Compound d can be obtained by reacting compound c obtained in the above-mentioned process, with ethylene glycol in a solvent such as benzene, toluene, or 1,2-dichloroethane, in the presence of an acid such as pyridinium-p-toluenesulfonate, p-toluenesulfonic acid, methanesulfonic acid, or acetic acid, with azeotropic removal of water produced while heating.

Compound d thus obtained can be used in the above-described Process 1-7 of Procedure 1, which describes the process for producing compound (I). Compounds corresponding to compound d, in which $M_1$ and/or $M_2$ are sulfur atoms, can also be obtained by methods known to those skilled in the art.

The compound of formula:

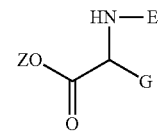

which is a raw material compound for synthesizing the compounds of formula (I), can be produced according to the reaction schemes of the following Procedures 3 to 5, which are methods known to those skilled in the art.

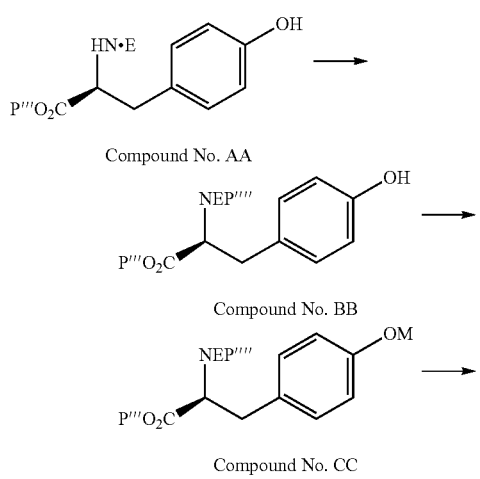

-continued

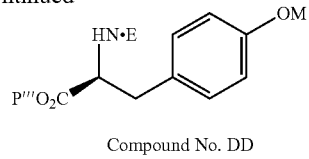

Compound No. DD

In the formulas shown above, P''' represents a carboxyl protecting group, P'''' represents an amino protecting group, and M represents a straight-chain or branched-chain alkyl group, straight-chain or branched-chain allynyl group, straight-chain or branched-chain alkenyl group, or cycloalkyl group.

Process 3-1

Compound BB can be obtained by protecting compound AA with an amino protecting group such as an acetyl, trifluoroacetyl, t-butoxycarbonyl, benzyloxycarbonyl, or 9-fluorenylmethylcarbonyl group. The conditions for this reaction are selected appropriately according to the type of protecting group P''''.

Process 3-2

Compound CC can be obtained by reacting compound BB with M substituted with a leaving group such as a halogen atom, or a methanesulfonic acid ester or toluenesulfonic acid ester, in a solvent such as diethyl ether, toluene, cyclohexane, acetone, dimethylformamide, dioxane, ethyl acetate, or dimethylsulfoxide, or in a mixed solvent thereof, in the presence of a base such as potassium carbonate, sodium hydroxide, or sodium hydride, at room temperature or while heating, but preferably at room temperature. Alternatively, compound CC can be obtained by reacting compound BB with M substituted with a hydroxyl group under Mitsunobu reaction conditions.

Process 3-3

Compound DD can be obtained by deprotecting the amino protecting group P'''' of compound CC. The conditions for this reaction are selected appropriately according to the type of protecting group P''''.

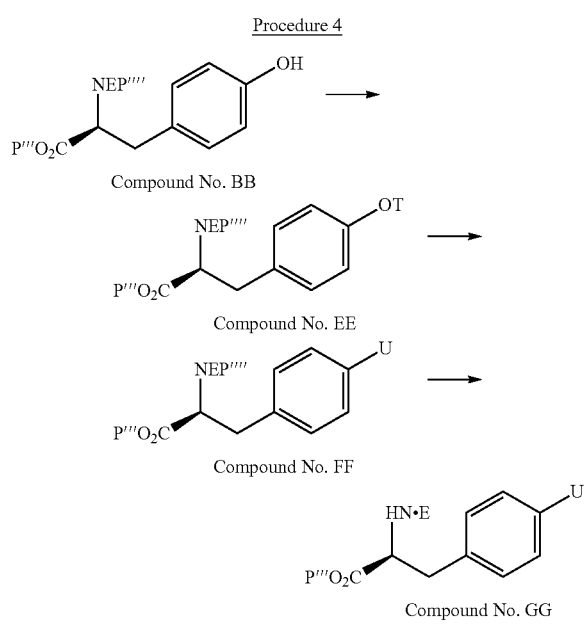

In the formulas shown above, P''' represents a carboxyl protecting group, P'''' represents an amino protecting group, T represents a leaving group such as a sulfonic acid ester, and U represents a substituted or unsubstituted aryl or a substituted or unsubstituted heteroaryl group.

Process 4-1

Compound EE can be obtained by reacting compound BB with methanesulfonic acid chloride, toluenesulfonic acid chloride, trifluorosulfonic acid anhydride, or such in a variety of solvents such as diethyl ether, toluene, cyclohexane, acetone, dimethylformamide, dioxane, ethyl acetate, and dimethylsulfoxide, or in a mixed solvent thereof, in the presence of a base such as N,N-diisopropylethylamine, triethylamine, pyridine, or 4-N,N-dimethylaminopyridine at room temperature or while cooling, but preferably while cooling.

Process 4-2

Compound FF can be obtained by reacting compound EE with an aryl- or heteroaryl boric acid derivative, aryl- or heteroaryl boric acid ester derivative, or such, in various solvents such as diethyl ether, toluene, benzene, dimethylformamide, dioxane, ethyl acetate, acetonitrile, and water, or in a mixed solvent thereof, in the presence of a palladium catalyst such as palladium diacetate, or tetrakis(triphenylphosphine)palladium, at room temperature or while heating, but preferably while heating.

Process 4-3

Compound GG can be obtained by deprotecting the amino protecting group P'''' of compound FF. The conditions for this reaction are selected appropriately according to the type of protecting group P''''.

Procedure 5

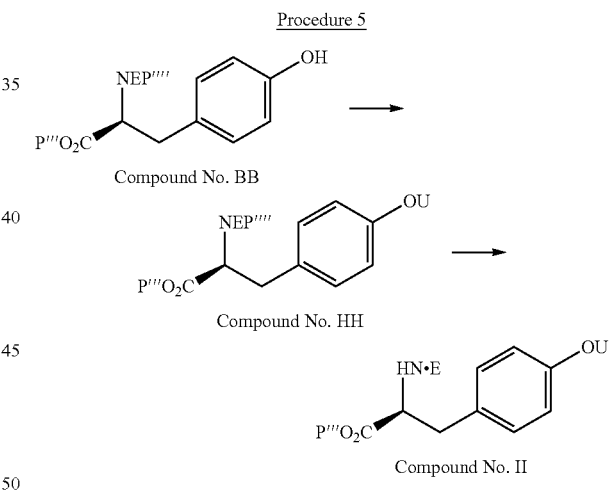

In the formulas shown above, P''' represents a carboxyl protecting group, P'''' represents an amino protecting group, and U represents a substituted or unsubstituted aryl or a substituted or unsubstituted heteroaryl group.

Process 5-1

Compound HH can be obtained by reacting compound BB with an aryl- or heteroaryl boric acid derivative, aryl- or heteroaryl boric acid ester derivative, halogenated aryl or halogenated heteroaryl derivative, or such in various solvents such as diethyl ether, toluene, cyclohexane, acetone, dimethylformamide, dioxane, methylene chloride, chloroform, and dimethylsulfoxide, or in a mixed solvent thereof, in the presence of a base such as sodium hydride or potassium carbonate, or in the presence of a base such as N,N-diisopropylethylamine, triethylamine, pyridine, or 4-N,N-dimethylaminopyridine and a catalyst such as copper (II)

diacetate, or copper (I) iodide, at room temperature or while heating, but preferably while heating.

Process 5-2

Compound II can be obtained by deprotecting the amino protecting group P'''' of compound HH. The conditions for this reaction are selected appropriately according to the type of protecting group P''''.

The above-mentioned compound (40), shown in the list of derivatives of formula (I), (and the same as the compound represented by formula (II)) has been disclosed in International Publication WO98/56755, and is known to be derived from microorganisms belonging to the genus *Aureobasidium*, and to have the effect of inhibiting immune response and antibacterial activity against pathogenic fungi such as *Candida albicans* and *Cryptococcus neoformans*. Compound (48), mentioned above, has been disclosed in International Publication WO94/18157 and is known to be useful as a squalene synthesis inhibitor and an antifungal agent.

Compound (40) can be produced by culturing a bacterial strain which produces the above-mentioned compound, where the bacteria is a filamentous bacteria belonging to the genus *Fusarium*, the genus *Aureobasidium*, or such, and then isolating the compound from the bacterial culture.

Bacterial strains that may be used for the production of compound (40) are not particularly limited, so long as they can produce the above-mentioned compound and belong to filamentous bacteria such as the genus *Fusarium*, the genus *Aureobasidium*, or such, and examples include *Fusarium* sp. F1476 strain (hereinafter referred to as "F1476 strain"), and *Aureobasidium* sp. TKR2449 strain (International Publication WO98/56755).

The F1476 strain has the property of advantageously producing compound (40), mentioned above. The physiological characteristics of the above F1476 strain are as follows: the viable temperature range is 10° C. to 30° C., or preferably 20° C. to 30° C.; and the viable pH range is 3 to 11, and preferably 5 to 7.

On Feb. 4, 2003, the F1476 strain denoted by *Fusarium* sp. F1476 was deposited under accession number FERM BP-8290 in the International Patent Organism Depositary at the National Institute of Advanced Industrial Science and Technology.

In the present invention, in addition to the above-mentioned F1476 strain, it is also possible to use natural or artificial mutants of the F1476 strain, or other filamentous bacterial species such as those of the genus *Fusarium*, the genus *Aureobasidium*, or such, which are microorganisms with the productivity of the F1476 strain.

In the present invention, the above-mentioned compound (40) can be obtained from a culture produced by inoculating the above F1476 strain into a nutrient-containing medium and culturing it. The above nutrients include carbon sources such as, for example, glucose, fructose, sucrose, starch, dextrin, glycerol, molasses, starch syrup, oils and fats, and organic acids.

The above nutrients include nitrogen sources such as, for example, soybean meal, cottonseed meal, corn steep liquor, casein, peptone, yeast extract, meat extract, germ, urea, amino acids, organic nitrogen compounds including ammonium salts, and inorganic nitrogen compounds.

The above nutrients include salts such as, for example, inorganic salts such as sodium salts, potassium salts, calcium salts, magnesium salts, and phosphate salts. These salts may be used individually or in appropriate combinations.

The above nutrients may be used individually or in appropriate combinations.

Heavy metal salts such as iron salts, copper salts, zinc salts, and cobalt salts; vitamins such as biotin and vitamin B1; and other organic and inorganic substances that accelerate the growth of bacteria and promote the production of the above compound (40) can be appropriately added to the above nutrient-containing medium as necessary.

In addition to the nutrients mentioned above, antifoaming agents such as silicone oil and polyalkyleneglycol ether, surfactants, and the like may be further added as necessary to the nutrient-containing medium.

When bacterial strains that produce the above-mentioned compound (40) are cultured in the above nutrient-containing medium, culture methods such as solid or liquid culture methods generally used for producing biologically active substances by culturing microorganisms can be used.

The above compound (40) is accumulated into the culture using the culture methods described above. In the present invention, compound (40) which has accumulated in the culture can be separated from the culture and then further purified as necessary according to known methods.

The above-mentioned separation can be performed by extracting the whole culture using non-hydrophilic organic solvents such as ethyl acetate, butyl acetate, chloroform, butanol, and methyl isobutyl ketone. Alternatively, after using filtration or centrifugation to separate the culture into culture solution and bacterial cells, compound (40) can also be separated from each of the culture solution and the bacterial cells.

To separate the above-mentioned compound (40) from the separated culture solution, an extraction method using the above non-hydrophilic organic solvent can be used; alternatively, a method of contacting the culture solution with an adsorptive carrier, adsorbing compound (40) in the culture solution to the carrier, and then eluting the compound with a solvent can be adopted.

Examples of the above carrier can include activated charcoal, powdered cellulose, and adsorptive resins. The above solvent can be one or a combination of two or more solvents, as appropriate, depending on the type, properties, and such of the carrier, and examples include appropriate combinations of hydrous solutions of water-soluble organic solvents and the like, including hydrous acetone and hydrous alcohol.

An extraction method using a hydrophilic organic solvent such as acetone can be employed to separate the above compound (40) from the separated bacterial cells.

In the present invention, a crude extract of compound (40), separated from the culture as described, can be further purified as necessary.

The above-mentioned purification can be performed by methods ordinarily used to separate and purify lipid soluble biologically active substances, and examples of such methods can include column chromatography methods and high-performance liquid chromatography methods that use carriers such as silica gel, activated alumina, activated charcoal, or adsorptive resins. When column chromatography methods using silica gel as the carrier are employed, examples of the elution solvent may include chloroform, ethyl acetate, methanol, acetone, and water, and two or more of these solvents may be used in combination.

When an above-mentioned high-performance liquid chromatography method is employed, the carrier can be, for example, a chemically-bonded silica gel to which an octadecyl group, octyl group, phenyl group, or such has been bonded; or a polystyrene-type porous polymer gel or such. As the mobile phase, for example, a hydrous solution of a water-soluble organic solvent such as hydrous methanol or hydrous acetonitrile may be used.

Derivatives represented by compounds (41) to (54) can be obtained using any one of Methods 1 to 11 described below, using the above-mentioned compound (40) as the starting material.

Method 1: Compound (46), which is a dihydro compound, can be obtained by hydrogenating the above-mentioned compound (40) in a solvent such as methanol, ethanol, ethyl acetate, or tetrahydrofuran, in the presence of a catalyst such as palladium carbon, palladium hydroxide, or Raney nickel, at room temperature or while heating.

Method 2: Compound (47) and the like, which are alcohols, can be obtained by reducing the above-mentioned compound (40) in a solvent such as methanol, ethanol, propanol, or tetrahydrofuran, in the presence of a reducing agent such as sodium borohydride, sodium trimethoxyborohydride, sodium cyanoborohydride, lithium borohydride, sodium diethylaluminum hydride, or lithium aluminum hydride, at room temperature or while cooling.

Method 3: Compound (48) and the like, which are dealkylated compounds, can be obtained by treating the above-mentioned compound (40) in a solvent such as methanol, dioxane, tetrahydrofuran, or water, in the presence of hydrochloric acid, sulfuric acid, methanesulfonic acid, trifluoroacetic acid or the like, at room temperature or while cooling. Compound (49) and the like, which are dihydro compounds, can be obtained by hydrogenating the above-mentioned compound (48) in a solvent such as methanol, ethanol, ethyl acetate, or tetrahydrofuran, in the presence of a catalyst such as palladium carbon, palladium hydroxide, Raney nickel, or platinum oxide, at room temperature or while heating.

Method 4: Tetraalkylated, tetraalkynylated, and tetraalkenylated compounds can be synthesized by treating compound (48) or the like with an alkylating agent such as alkyl halide, allyl halide, or alkynyl halide, in the presence of a base such as sodium hydroxide, potassium hydroxide, calcium carbonate, or potassium carbonate, in a solvent such as dimethyl formamide (DMF) or tetrahydrofuran, at room temperature or while heating. Alkylated, alkynylated, and alkenylated compounds can be synthesized by treating these compounds in the presence of a base such as sodium hydroxide, potassium hydroxide, calcium carbonate, or potassium carbonate, in a solvent such as methanol, dioxane, tetrahydrofuran, or water, at room temperature or while heating.

Method 5: Compound (50) and the like, which are the corresponding triamide compounds, can be obtained by treating the above-mentioned compound (40) and various amines with a condensing agent such as dicyclohexylcarbodiimide (DCC), water soluble carbodiimide hydrochloride salt (WSC.HCl), or 1-hydroxybenzotriazole (HOBt), in the presence of a base such as diisopropylethylamine or triethylamine, in a solvent such as dimethylformamide (DMF) or tetrahydrofuran at room temperature or while heating.

Method 6: Compound (51) and the like, which are tetrahydro compounds, can be obtained by hydrogenating the above-mentioned compound (40) in a solvent such as methanol, ethanol, ethyl acetate, or tetrahydrofuran, in the presence of a catalyst such as palladium carbon, palladium hydroxide, Raney nickel, or platinum oxide, at room temperature or while heating.

Method 7: Corresponding triesters ($R^1=R^2=R^3=R$) can be obtained by reacting the above-mentioned compound (40) with various alcohols (R—OH) using a condensing reagent such as dicyclohexylcarbodiimide (DCC) in solvents such as tetrahydrofuran, DMF, and dichloromethane at room temperature or while heating. Alternatively, a trimethylester compound ($R^1=R^2=R^3=CH_3$) can be obtained by treating the above-mentioned compound (40) with an amide dihydro compound, trimethylsilyldiazomethane ($TMSCHN_2$) or such, in a mixed solvent of methanol, dichloromethane, and such.

Method 8: Compound (52) and the like, which are deketonized compounds, can be obtained by treating a trimethyl ester obtained in Method 7 with a hydrazine derivative such as 4-toluenesulfonylhydrazide, in a solvent such as methanol, ethanol, and butanol at room temperature or while heating, to obtain the corresponding hydrazide, then treating this hydrazide with a reducing agent such as catecholborane, and then placing it in a solvent such as ethanol, methanol, and water, in the presence of a base such as lithium hydroxide, sodium hydroxide, or potassium hydroxide, at room temperature or while heating.

Method 9: Compounds (53), (54), and such, which are the corresponding oxime ethers and oximes, can be obtained by treating the above-mentioned compound (40) with hydroxyl amines or various O-substituted hydroxylamines in the presence of pyridine, triethylamine, diisopropylethylamine, or such, at room temperature or while heating.

Method 10: Halogenated compounds can be obtained by treating the above-mentioned compound (40) with diethylaminosulfur trifluoride (DAST) or such in a solvent such as tetrahydrofuran, dichloromethane, or chloroform.

Method 11: Corresponding amines ($B=-N(R^4)(R^5)$) can be obtained by performing reductive amination by treating the above-mentioned compound (40) and various amines with a reducing agent such as sodium cyanoborohydride or sodium triacetoxyborohydride, in solvents such as ethanol, methanol, and tetrahydrofuran, under neutral or weakly acidic conditions, at room temperature or while heating.

Compounds of the present invention that suppress the expression of serine palmitoyltransferase may be, for example, RNAs complementary to the transcripts of DNAs encoding serine palmitoyltransferase, or ribozymes that specifically cleave these transcripts. In the present invention, the origin of the serine palmitoyltransferase whose expression is to be suppressed is not particularly limited, but it is preferably derived from mammals, and is more preferably derived from humans. DNAs encoding serine palmitoyltransferase include DNAs comprising the nucleotide sequence of SEQ ID NO: 4 or 6 (LCB1 or LCB2), DNAs encoding proteins comprising the amino acid sequence of SEQ ID NO: 5 or 7, and naturally occurring DNAs encoding proteins comprising an amino acid sequence with a substitution, deletion, addition, and/or insertion of one or more amino acids in the amino acid sequence of SEQ ID NO: 5 or 7. "Proteins comprising an amino acid sequence with a substitution, deletion, addition, and/or insertion of one or more amino acids" are functionally equivalent to and also have high homology with a naturally occurring protein. "High homology" refers to sequence identity of at least 50% or more, more preferably 70% or more, and much more preferably 90% or more (e.g. 95%, 96%, 97%, 98%, 99% or more) throughout the entire amino acid sequence.

Naturally occurring DNAs are DNAs that hybridize to DNAs comprising the nucleotide sequence of SEQ ID NO: 4 or 6. Those skilled in the art can appropriately select conditions for hybridization, but examples of conditions for post-hybridization washing include 5×SSC and 0.1% SDS at 42° C., and preferably in 5×SSC and 0.1% SDS at 50° C. More preferable hybridization conditions include, for example, 0.1×SSC and 0.1% SDS at 65° C.

Examples of the RNAs complementary to the transcripts of DNAs encoding serine palmitoyltransferase can be more preferably siRNAs represented by SEQ ID NOs: 1 and 2.

Examples of the compounds of the present invention include compounds that block the process of dihydroceramide biosynthesis from sphinganine (dihydrosphingosine), which is a step midway through the process of sphingolipid biosynthesis. Examples of compounds that block this biosynthetic process can be compounds that inhibit the enzyme activity of dihydrosphingosine-N-acyltransferase, which is involved in the biosynthesis, or compounds that suppress the expression of dihydrosphingosine-N-acyltransferase.

Compounds of the present invention that inhibit the enzyme activity of dihydrosphingosine-N-acyltransferase may be any compound, so long as they inhibit the enzyme activity, but preferable examples include fumonisin B1 or derivatives thereof.

Examples of the compounds of the present invention that suppress expression of dihydrosphingosine-N-acyltransferase can include RNAs complementary to the transcripts of DNAs encoding dihydrosphingosine-N-acyltransferase, or ribozymes that specifically cleave these transcripts.

Examples of the compounds of the present invention include compounds that block the process of sphingomyelin biosynthesis from ceramide, which is a step midway through the process of sphingolipid biosynthesis. Examples of compounds that block this biosynthetic process include compounds that inhibit the enzyme activity of sphingomyelin synthase, which is involved in the biosynthesis, or compounds that suppress the expression of sphingomyelin synthase.

Compounds of the present invention that inhibit the enzyme activity of sphingomyelin synthase may be any compounds, so long as they inhibit the enzyme activity.

Examples of the compounds of the present invention that suppress the expression of sphingomyelin synthase include RNAs complementary to the transcripts of DNAs encoding sphingomyelin synthase, or ribozymes that specifically cleave these transcripts. DNAs encoding sphingomyelin synthase include DNAs comprising the nucleotide sequence of SEQ ID NO: 8, DNAs encoding proteins comprising the amino acid sequence of SEQ ID NO: 9, and naturally occurring DNAs encoding proteins comprising an amino acid sequence with a substitution, deletion, addition, and/or insertion of one or more amino acids in the amino acid sequence of SEQ ID NO: 9.

In the present invention, the phrase "suppress expression of an enzyme" comprises suppressing gene transcription as well as suppressing translation to a protein. The phrase comprises not only complete arrest of DNA expression, but also reduced DNA expression.

One embodiment of "an RNA complementary to the transcript of a DNA encoding an enzyme" of the present invention is an antisense RNA complementary to the transcript of the DNA encoding the enzyme.

Antisense nucleic acids have multiple activities such as the following, which contribute to suppression of target gene expression. Specifically, these activities include: inhibition of transcription initiation by triple strand formation; suppression of transcription by hybridization with the site where an RNA polymerase has formed a local open loop structure; suppression of transcription by hybridization with the RNA being synthesized; suppression of splicing by hybridization with the junction between an intron and an exon; suppression of splicing by hybridization with the site of spliceosome formation; suppression of mRNA translocation from the nucleus to the cytoplasm by hybridization with mRNA; suppression of splicing by hybridization with the capping site or with the poly A addition site; suppression of translation initiation by hybridization with the binding site for the translation initiation factors; suppression of translation by hybridization with the site for ribosome binding near the initiation codon; inhibition of peptide chain elongation by hybridization with the coding region or with the polysome binding sites of mRNA; and suppression of gene expression by hybridization with the site of interaction between nucleic acids and proteins. These activities suppress target gene expression by inhibiting the process of transcription, splicing, or translation.

Antisense sequences used in the present invention can suppress target gene expression by any of the above activities. In one embodiment, if an antisense sequence is designed to be complementary to a noncoding region near the 5' end of the gene's mRNA, it will effectively inhibit translation of that gene. Sequences complementary to a coding region or to a noncoding region on the 3' side can also be used. Thus, the antisense DNAs used in the present invention also include DNAs comprising antisense sequences against the sequences of both the noncoding and the coding regions of the gene. The antisense DNAs to be used are linked downstream of an appropriate promoter, and preferably, a sequence comprising the transcription termination signal is linked on the 3' side. DNAs thus prepared can be transformed into a desired plant by known methods. The sequence of an antisense DNA is preferably a sequence complementary to an endogenous gene of the plant to be transformed or a part thereof; however, it need not be perfectly complementary, so long as it can effectively inhibit gene expression. The transcribed RNAs are preferably 90% or more, and most preferably 95% or more complementary to transcripts of the target gene. In order to effectively inhibit target gene expression using an antisense sequence, an antisense DNA should be at least 15 nucleotides or more, more preferably at least 100 nucleotides or more, and still more preferably at least 500 nucleotides or more. The antisense DNAs to be used are generally shorter than 5 kb, and preferably shorter than 2.5 kb.

One embodiment of "an RNA complementary to the transcript of a DNA encoding an enzyme" is a dsRNA complementary to the transcript of the DNA encoding the enzyme. RNAi is a phenomenon where introduction into cells of a double-stranded RNA (hereinafter, dsRNA) comprising a sequence identical or similar to a target gene sequence suppresses the expression of both the introduced foreign gene and the endogenous target gene. When approximately 40 to several hundred base pairs of dsRNA are introduced into cells, an RNaseIII-like nuclease called Dicer, which has a helicase domain, excises the dsRNA in the presence of ATP from the 3' end, approximately 21 to 23 base pairs at a time, and produces short interference RNAs (siRNAs). Binding of a specific protein to these siRNAs forms nuclease complexes (RNA-induced silencing complex: RISC). These complexes recognize and bind to sequences the same as those of the siRNAs, and cleave the mRNAs of the target gene in the middle of the siRNAs using RNaseIII-like enzyme activity. In addition to this pathway, the antisense siRNA strands bind to mRNAs and act as primers for RNA-dependent RNA polymerase (RsRP) to synthesize dsRNAs. Pathways in which these dsRNAs again become Dicer substrates and produce new siRNAs to amplify their action can also be considered.

The RNAs of the present invention can be expressed from antisense coding DNAs that encode antisense RNAs for any region of a target gene mRNA, and from sense coding DNAs that encode sense RNAs for any region of a target gene mRNA. dsRNAs can be produced from such antisense and sense RNAs.

When a dsRNA expression system of the present invention is incorporated into a vector or the like, the antisense and sense RNAs may be expressed from the same vector, or they may be expressed from different vectors. For example, to express an antisense RNA and a sense RNA from the same vector, an antisense RNA expression cassette and a sense RNA expression cassette in which a promoter that may initiate expression of a short RNA, such as the polIII system, is linked upstream of each of the antisense-encoding DNA and sense-encoding DNA, can be individually constructed; and then these cassettes can be inserted into a vector in the same or opposite direction. Furthermore, an expression system that has the antisense-encoding DNA and sense-encoding DNA positioned in opposite directions so that they face each other on different strands can be composed. In this system, a single double-stranded DNA (siRNA-encoding DNA) in which the antisense RNA-encoding strand and sense RNA-encoding strand are paired is provided, and promoters can be placed on both sides in opposite directions so that the antisense RNA and the sense RNA can be expressed from each of the strands. In this case, to avoid addition of an unnecessary sequence downstream of the sense RNA or antisense RNA, a terminator is preferably placed at the 3' end of each of the strands (the antisense RNA-encoding strand and the sense RNA-encoding strand). A sequence of four or more continuous adenine (A) nucleotides can be used as this terminator. Furthermore, in this palindromic expression system, the two promoters are preferably different types.

To express antisense and sense RNAs from different vectors, for example, an antisense RNA expression cassette and a sense RNA expression cassette in which a promoter that may initiate expression of a short RNA, such as the polIII system, is linked upstream of each of the antisense-encoding DNA and the sense-encoding DNA, can be individually constructed; and then these cassettes can be incorporated into different vectors.

In RNAi of the present invention, siRNAs may be used as the dsRNAs. The term "siRNA" refers to a double-stranded RNA comprising short chains in a range that does not show toxicity within cells, for example, 15 to 49 base pairs long, preferably 15 to 35 base pairs long, and more preferably 21 to 30 base pairs long. Alternatively, the siRNAs to be expressed may be transcribed such that the final length of the double-stranded RNA portion may be, for example, 15 to 49 base pairs, preferably 15 to 35 base pairs, and more preferably 21 to 30 base pairs.

The DNAs used for RNAi need not be completely identical to the target gene, but should have sequence identity of at least 70% or more, preferably 80% or more, more preferably 90% or more, and most preferably 95% or more.

In dsRNAs, the double-stranded portion in which the RNAs are paired is not limited to portions that are completely paired, and may comprise unpaired portions caused by mismatches (in which the corresponding nucleotides are not complementary), bulges (in which one of the strands lacks corresponding nucleotides), and such. In the present invention, the double-stranded RNA regions, in which the RNAs of dsRNAs are paired, may comprise both bulges and mismatches.

DNAs that encode ribozymes can also be used to "suppress expression of an enzyme" in the present invention. A ribozyme is an RNA molecule with catalytic activity. Some ribozymes have various activities, and among them, research on ribozymes that work as RNA-cleaving enzymes has enabled the design of ribozymes aimed at site-specific cleavage of RNAs. Some ribozymes such as those of group I intron type or the M1RNA contained in RNaseP consist of 400 nucleotides or more, while others belonging to the hammerhead type or the hairpin type have an active domain of about 40 nucleotides.

For example, the self-cleavage domain of a hammerhead type ribozyme cleaves at the 3' side of C15 of the sequence G13U14C15, but formation of a base pair between U14 and A at the ninth position is considered important for the ribozyme activity, and it has been shown that the cleavage also occurs when the nucleotide at the 15th position is A or U instead of C. If the substrate binding site of the ribozyme is designed to be complementary to an RNA sequence adjacent to the target site, a restriction-enzyme-like RNA cleaving ribozyme which recognizes the sequence UC, UU, or UA within the target RNA can be created. For example, multiple sites that can be used as the ribozyme target are present in the coding region of an enzyme of the present invention that will be the target of inhibition.

A hairpin type ribozyme is also useful for an objective of the present invention. Hairpin type ribozymes can be found, for example, in the minus strand of the satellite RNAs of Tobacco ringspot virus (J. M. Buzayan, Nature 323: 349 (1986)). It has been shown that this ribozyme can also be designed to target-specifically cleave RNA.

The ribozyme designed to cleave the target is linked to a promoter such as Cauliflower mosaic virus 35S promoter, and to a transcription termination sequence, so that it will be transcribed in plant cells. However, if extra sequences have been added to the 5' end or 3' end of the transcribed RNA, the ribozyme activity can be lost. In this case, one can place an additional trimming ribozyme, which functions in cis to perform the trimming on the 5' or the 3' side of the ribozyme portion, in order to precisely cut the ribozyme portion alone from the transcribed RNA containing the ribozyme (K. Taira et al. (1990) Protein Eng. 3: 733; A. M. Dzaianott and J. J. Bujarski (1989) Proc. Natl. Acad. Sci. USA 86: 4823; C. A. Grosshands and R. T. Cech (1991) Nucleic Acids Res. 19: 3875; K. Taira et al. (1991) Nucleic Acid Res. 19: 5125). Multiple sites within the target gene can be cleaved by arranging these structural units in tandem to achieve greater effects (N. Yuyama et al., Biochem. Biophys. Res. Commun. 186: 1271 (1992)). By using such ribozymes, it is possible to specifically cleave the transcripts of the target gene of the present invention to suppress its gene expression.

The term "treatment" in the present description means administering the pharmaceuticals of the present invention to subjects to eliminate HCV or reduce HCV, to suppress further spread of HCV, and to alleviate the symptoms caused by HCV infection. Examples of symptoms caused by HCV infection are preferably hepatitis C, liver cirrhosis, liver fibrosis, liver cancer and such.

The compounds of the present invention can be used as pharmaceutical agents directly or in the form of pharmaceutically acceptable salts. The above-mentioned salts are not particularly limited, so long as they are pharmaceutically acceptable, and examples include salts formed with mineral acids such as hydrochloric acid, sulfuric acid, nitric acid, phosphoric acid, and hydrobromic acid; salts formed with organic acids such as acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, and camphorsulfonic acid; and salts formed with alkali metals or alkaline earth metals such as sodium, potassium, and calcium.

The amount of an active ingredient compound comprised in the above-mentioned pharmaceutical preparation is not particularly limited and can be appropriately selected in a wide range; however, examples are 0.1% to 99.5% by weight, or preferably 0.5% to 90% by weight.

A compound of the present invention can be formulated as the base according to conventional methods using known adjuvants that may be used ordinarily in the art of pharmaceutical preparation, such as excipients, binders, disintegrators, lubricants, flavoring agents, solubilizing adjuvants, suspending agents, and coating agents. When shaping into the form of tablets, a wide variety of substances conventionally known as carriers in the art can be used, and examples include excipients such as lactose, sucrose, sodium chloride, glucose, urea, starch, calcium carbonate, kaolin, crystalline cellulose, and silicic acid; binders such as water, ethanol, propanol, simple syrup, glucose solution, starch solution, gelatin solution, carboxymethylcellulose, shellac, methylcellulose, potassium phosphate, and polyvinylpyrrolidone; disintegrators such as dried starch, sodium alginate, agar powder, laminaran powder, sodium bicarbonate, calcium carbonate, polyoxyethylene sorbitan fatty acid esters, sodium lauryl sulfate, stearic acid monoglyceride, starch, and lactose; disintegration inhibitors such as sucrose, stearic acid, cacao butter, and hydrogenated oil; absorbefacients such as quaternary ammonium salts and sodium lauryl sulfate; moisturizers such as glycerin and starch; adsorbents such as starch, lactose, kaolin, bentonite, and colloidal silicic acid; and lubricants such as purified talc, stearate, boric acid powder, and polyethylene glycol.

Tablets can be prepared, as necessary, as ordinary coated tablets, such as sugar-coated tablets, gelatin-coated tablets, enteric-coated tablets, and film-coated tablets, or as double layered tablets or multilayered tablets. When shaping into the form of pills, a wide variety of substances conventionally known as carriers in the art can be used, and examples include excipients such as glucose, lactose, cacao butter, starch, hardened vegetable oil, kaolin, and talc; binders such as gum arabic powder, tragacanth powder, gelatin, and ethanol; and disintegrators such as laminaran agar. When shaping into the form of suppositories, a wide variety of substances conventionally known as carriers in this field can be used, and examples include polyethylene glycol, cacao butter, higher alcohols, esters of higher alcohols, gelatin, and semi-synthetic glycerides. When preparing injections, solutions and suspensions are sterilized and are preferably isotonic with blood, and when making these solution, emulsion, and suspension forms, any substances commonly used as diluents in the field can be used, such as water, ethanol, propylene glycol, ethoxylated isostearyl alcohol, polyoxylated isostearyl alcohol, and polyoxyethylene sorbitan fatty acid esters. In these instances, adequate amounts of sodium chloride, glucose, or glycerin can be comprised in the pharmaceutical preparations to prepare isotonic solutions, and ordinary solubilizing adjuvants, buffers, analgesic agents, and such may also be added. The pharmaceutical preparations may further comprise, as necessary, coloring agents, preservatives, flavors, flavoring agents, and sweeteners, as well as other pharmaceutical agents.

The above-mentioned pharmaceutical compositions are preferably administered in unit dosage forms, and can be administered orally, interstitially (subcutaneously, intramuscularly, intravenously, and such), locally (percutaneously), or transrectally. The pharmaceutical compositions are obviously administered in dosage forms suited to these administration methods.

When administering the compounds of the present invention or pharmaceutically acceptable salts thereof as pharmaceutical agents, the doses of the antiviral agents are preferably adjusted after considering the patient's condition such as age and weight, the administration route, and the property and degree of the disease; however, for humans, the daily dose of the active ingredient of the present invention for adults is ordinarily within the range of 0.1 mg to 2000 mg. While doses lower than the above-mentioned range may be sufficient in some cases, doses higher than this range may be required in other cases. When a high dose is used, the daily dosage is preferably administered in several divided doses.

The above-mentioned oral administration can be carried out using solid, powdered, or liquid dosage units, such as powders, powdered drugs, tablets, sugar-coated agents, capsules, drops, sublingual tablets, and other dosage forms.

The above-mentioned interstitial administration can be carried out, for example, using liquid unit dosage forms for subcutaneous, intramuscular, or intravenous injections, such as solutions and suspensions. These are produced by suspending or dissolving a certain amount of a compound of the present invention or a pharmaceutically acceptable salt thereof, in a non-toxic liquid carrier suitable for purposes of injection, such as an aqueous or oily medium, and then sterilizing this suspension or solution.

The above-mentioned local administration (percutaneous administration and such) can be carried out using external preparation forms such as solutions, creams, powders, pastes, gels, and ointments. These are produced by combining a certain amount of a compound of the present invention or a pharmaceutically acceptable salt thereof, with one or more of a flavor, coloring agent, filler, surfactant, moisturizer, emollient, gelling agent, carrier, preservative, and stabilizer suited to the aim of the external preparation.

The above-mentioned transrectal administration can be carried out using suppositories and the like, prepared by mixing a certain amount of a compound of the present invention or a pharmaceutically acceptable salt thereof into a low-melting solid comprising, for example, higher esters such as myristyl palmitate ester, polyethylene glycol, cacao butter, or a mixture thereof.

The above-mentioned administrations can be carried out using liquid unit dosage forms for subcutaneous, intramuscular, or intravenous injections, such as solutions or suspensions. They are produced by suspending or dissolving a certain amount of a compound of the present invention or a pharmaceutically acceptable salt thereof, in a non-toxic liquid carrier appropriate to the purpose of the injection, such as an aqueous or oily medium, and then sterilizing this suspension or solution.

The present invention relates to serine palmitoyltransferase inhibitors comprising compounds represented by formula (I) or derivatives thereof. It also relates to serine palmitoyltransferase inhibitors comprising the compound represented by formula (II), or to derivatives thereof.

Such inhibitors can be used not only as pharmaceutical agents for preventing or treating HCV infections, but also as useful pharmaceutical agents for preventing or treating diseases induced by abnormalities in sphingolipid synthesis: for example, sphingolipidosis, which is a disease that shows abnormal accumulation of lipids (sphingomyelin); Alzheimer's disease, which involves β-amyloid proteins with a sphingolipid binding motif; amyotrophic lateral sclerosis, which causes nerve cell death upon an increase of ceramide in the spinal motor neurons (Cutler, R. G., et al., Ann. Neurol., 52, 448-457, 2002); HIV infection, which involves gp120 proteins; prion diseases, which involves PrP proteins; and infection by viruses that infect host cells by binding to rafts (for example influenza virus and HIV).

The present invention relates to methods of screening for pharmaceutical agents for treating or preventing HCV infections.

In a first embodiment of the screening methods of the present invention, test compounds are first contacted with enzymes involved in the biosynthesis of sphingomyelin from palmitoyl CoA.

Examples of "enzymes involved in the biosynthesis of sphingomyelin from palmitoyl CoA" (hereinafter the abbreviated form "biosynthetic enzymes" may also be used) in the screening methods of the present invention include serine palmitoyltransferase, 3-ketodihydrosphingosine reductase, dihydrosphingosine-N-acyltransferase, dihydroceramide desaturase, and sphingomyelin synthase. The origin of these enzymes is not particularly limited, and these enzymes may be derived from, for example, yeast, mammals including humans, or the like.

The state of the biosynthetic enzymes used in the first embodiment is not particularly limited, and they may be in a purified state, expressed in cells, or expressed in cell extracts, for example. Examples of cells in which these biosynthetic enzymes are expressed are cells expressing endogenous biosynthetic enzymes, or cells expressing foreign biosynthetic enzymes. Examples of the cells expressing endogenous biosynthetic enzymes include cultured cells, but are not limited thereto. The cultured cells are not particularly limited, and commercially available cells may be used, for example. The cells expressing foreign biosynthetic enzymes can be produced, for example, by introducing a vector carrying a DNA encoding a biosynthetic enzyme into cells. Vectors can be introduced into cells using conventional methods such as calcium phosphate precipitation, electroporation methods, lipofectamine methods, and microinjection methods. Animal species from which these cells to be introduced with a foreign biosynthetic enzyme are derived are not limited to mammals, and they may be any animal species so long as techniques for expressing foreign proteins in their cells have been established.

Cell extracts in which a biosynthetic enzyme is expressed can include, for example, cell extracts included in in vitro transcription-translation systems, to which a vector carrying a DNA encoding a biosynthetic enzyme has been added. The in vitro transcription-translation systems are not particularly limited, and commercially available in vitro transcription-translation kits and such may be used.

The "test compounds" in the methods of the present invention are not particularly limited, and examples include single compounds such as natural compounds, organic compounds, inorganic compounds, proteins, and peptides, as well as compound libraries, expression products of gene libraries, cell extracts, cell culture supernatants, fermentation products, marine organism extracts, plant extracts, prokaryotic cell extracts, eukaryotic single cells, or animal cell extracts. The test compounds can be suitably labeled as necessary, and then used. Examples of the labels include radiolabels and fluorescence labels. "A number of test compounds" is not particularly limited, and in addition to the above-mentioned test compounds, includes, for example, mixtures produced by mixing multiple types of these test compounds.

In the present invention, the "contact" is carried out according to the condition of the biosynthetic enzyme. For example, if the biosynthetic enzyme is in a purified condition, the contact can be made by adding the test compounds to the purified sample. If the biosynthetic enzyme is in a form expressed in cells or in a cell extract, the contact can be made by adding the test compounds to the cell culture solution or the cell extract, respectively. Cells of the present invention are not particularly limited, but preferable cells are derived from yeasts or mammals including humans. When the test compound is a protein, the contact can be carried out, for example, by introducing a vector carrying a DNA encoding the protein into cells expressing a biosynthetic enzyme, or by adding this vector to a cell extract in which the biosynthetic enzyme is expressed. A two-hybrid method that uses yeast or animal cells can also be used.

In the first embodiment, the binding between the biosynthetic enzyme and a test compound is then detected. The means for detecting or measuring the binding between proteins can use labels attached to proteins, for example. Examples of the types of labels include fluorescence labels and radiolabels. Measurements can be made using known methods such as the yeast two hybrid method, or measurement methods that use BIACORE. In the present methods, test compounds that bind to the biosynthetic enzyme are then selected. The selected test compounds include pharmaceutical agents for treating or preventing HCV infections. The selected test compounds may also be used as test compounds for the screening below.

In a second embodiment of the screening methods of the present invention, a test compound is first contacted with cells containing enzymes involved in the biosynthesis of sphingomyelin from palmitoyl CoA. These biosynthetic enzymes and the terms "test compound" and "contact" have the same meaning as described above.

In the second embodiment, the amount of compounds synthesized in the process of sphingomyelin biosynthesis from palmitoyl CoA is measured. Examples of the synthesized compounds include intermediate products such as 3-ketodihydrosphingosine, dihydrosphingosine, dihydroceramide, and ceramide, but sphingomyelin, the final product, is more preferred. The synthesized compounds can be quantified by measuring using known methods such as the GC-MS method, MS-MS method, and LC-MS method. Further, when the synthesized compound is a phospholipid such as sphingomyelin, quantification can also be carried out by quantifying the phosphates in the phospholipid. In the present methods, test compounds that reduce the amount of synthesized compounds as compared to that in the absence of test compound contact are then selected as pharmaceutical agents for treating or preventing HCV infections.

In a third embodiment of the screening methods of the present invention, a test compound is first contacted with cells containing enzymes involved in the biosynthesis of sphingomyelin from palmitoyl CoA. These biosynthetic enzymes and the terms "test compound" and "contact" have the same meaning as described above.

In the third embodiment, the expression level of the enzymes involved in the process of sphingomyelin biosynthesis from palmitoyl CoA is then measured. The expression level of these biosynthetic enzymes can be measured by methods known to those skilled in the art. For example, the transcription level of a biosynthetic enzyme gene can be measured by extracting its mRNAs according to standard methods, and then performing a Northern hybridization method or RT-PCR method using these mRNAs as templates. Furthermore, DNA array technology can be used to measure the expression level of the biosynthetic enzymes.

The level of gene translation can be measured by using standard methods to collect fractions containing the biosynthetic enzymes, and then detecting the expression of the biosynthetic enzymes using electrophoresis such as SDS-PAGE. The level of gene translation can also be measured by performing a Western blotting method using antibodies against the biosynthetic enzymes to detect the expression of these enzymes.

The antibodies used to detect the biosynthetic enzymes are not particularly limited, so long as they are detectable antibodies, and for example, monoclonal antibodies and polyclonal antibodies may be used. The antibodies can be prepared by methods known to those skilled in the art. Polyclonal antibodies can be obtained, for example, as follows: a biosynthetic enzyme, or a recombinant protein expressed as a GST-fusion protein in a microorganism such as E. coli, or a partial peptide thereof, is used to immunize small animals such as rabbits, and their sera are collected. The antibodies are prepared by purifying these sera using ammonium sulfate precipitation, protein A or protein G column chromatography, DEAE ion exchange chromatography, affinity column chromatography with columns to which a biosynthetic enzyme or synthetic peptide has been coupled, and such. For monoclonal antibodies, for example, a biosynthetic enzyme or a partial peptide thereof is used to immunize small animals such as mice, the spleens are removed from these same mice and homogenized to separate the cells, and the cells are fused with mouse myeloma cells using reagents such as polyethylene glycol. From the resulting fused cells (hybridomas), clones producing an antibody that binds to the biosynthetic enzyme are selected. Next, the obtained hybridomas are transplanted into the abdominal cavities of mice, ascites are collected from these same mice, and the monoclonal antibody can be prepared by purifying the obtained ascites using ammonium sulfate precipitation, protein A or protein G column chromatography, DEAE ion exchange chromatography, chromatography with affinity columns to which the biosynthetic enzyme or synthetic peptide has been coupled, and such.

In the third embodiment, test compounds that reduce the expression level of the biosynthetic enzyme as compared that in the absence of test compound contact are selected as pharmaceutical agents for treating or preventing HCV infections.

In a fourth embodiment of the screening methods of the present invention, a cell comprising a DNA in which a reporter gene is operably linked downstream of a promoter region of a biosynthetic enzyme, or a cell extract thereof, is first provided.

In the fourth embodiment, the phrase "operably linked" means that a promoter region of a biosynthetic enzyme and a reporter gene are linked, so that expression of the reporter gene is induced by the binding of a transcription factor to the promoter region of the biosynthetic enzyme. Therefore, even if the reporter gene is linked to another gene, and a fusion protein is formed with another gene product, as long as the expression of the fusion protein is induced by the binding of the transcription factor to the promoter region of the biosynthetic enzyme, this reporter gene can be considered "operably linked", as described above.

The reporter gene mentioned above is not particularly limited as long as its expression is detectable, and examples of such genes include the CAT gene, lacZ gene, luciferase gene, β-glucuronidase gene (GUS), and GFP gene, which are generally used by those skilled in the art. In the fourth embodiment, a test compound is then contacted with an above-mentioned cell or cell extract. Next, the expression level of the above-mentioned reporter gene in the cell or in the cell extract is measured. The terms "test compound" and "contact" have the same meaning as described above.

The expression level of a reporter gene can be measured by methods known to those skilled in the art, chosen according to the type of reporter gene used. For example, when the reporter gene is the CAT gene, its expression level can be measured by detecting the acetylation of chloramphenicol by the gene product. When the reporter gene is the lacZ gene, its expression level can be measured by detecting the color development of a pigment compound that results from the catalytic action of the gene expression product. When the reporter gene is the luciferase gene, its expression level can be measured by detecting the fluorescence of a fluorescent compound that results from the catalytic action of the gene expression product. When the reporter gene is the β-glucuronidase gene (GUS), its expression level can be measured by detecting the luminescence of Glucuron (ICN) or the color development of 5-bromo-4-chloro-3-indolyl-β-glucuronide (X-Gluc) that results from the catalytic action of the gene expression product. When the reporter gene is the GFP gene, its expression level can be measured by detecting the fluorescence of the GFP protein.

In the fourth embodiment, test compounds that reduce the expression level of the above-mentioned reporter genes as compared to that in the absence of test compound contact are selected as pharmaceutical agents for treating or preventing HCV infections.

In a fifth embodiment of the screening methods of the present invention, enzymes involved in the biosynthesis of sphingomyelin from palmitoyl CoA are first contacted with test compounds. These biosynthetic enzymes and the terms "test compound" and "contact" have the same meaning as described above.

In the fifth embodiment, the activity of the above-mentioned biosynthetic enzymes is then measured. The activity of the biosynthetic enzymes can be determined using methods known for each of the enzymes. Methods generally used are activity measuring methods that use differences in spectroscopic properties between substrates and products, and measure their change with time; however, one may select methods that more directly measure the enzyme reaction using information from informative groups on the enzyme (for example, amino acid residues such as tryptophan or tyrosine, and coenzymes) obtained by stopped-flow methods or by various relaxation methods. Examples of spectroscopic methods used in the activity measuring methods include absorption, fluorescence, CD, NMR, ESR, IR, and Raman spectroscopies. In the fifth embodiment, test compounds that reduce the activity of the biosynthetic enzymes as compared to that in the absence of test compound contact are selected as pharmaceutical agents for treating or preventing HCV infections.

The present invention relates to kits for use in the five screening methods described above. Such kits may comprise materials to be used in the detection step or measurement step of the five screening methods described above. Examples of such materials include probes, primers, antibodies, and stain solutions that are necessary for measuring the expression levels of enzymes involved in the biosynthesis of sphingomyelin from palmitoyl CoA. The kits may also comprise distilled water, salts, buffers, protein stabilizers, and preservatives. All prior art references cited herein are incorporated herein by reference.

EXAMPLES

Herein below, the present invention will be specifically described with reference to Examples, but it is not to be construed as being limited thereto.

Example 1

Measurement by Northern Blot Analysis of the Activity of Myriocin or the Compound Represented by Formula (II), which is Derived from Microorganisms Such as Those of the Genus *Aureobasidium*, in Inhibiting HCV RNA Replication Between 1 pM and 100 µM of myriocin or the compound represented by the following formula (II) was added to Huh-3-1 replicon cells, and the cells were cultured under 5% $CO_2$ at 37° C.

Formula (II):

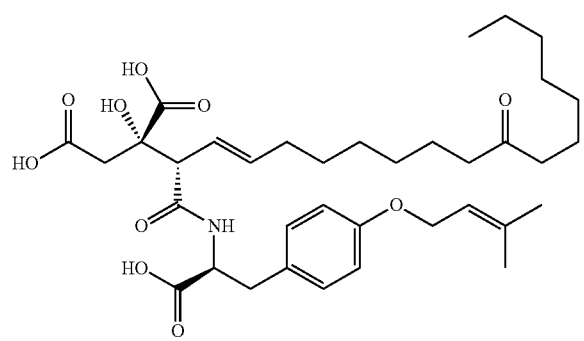

Cells were collected 72 hours later, total RNAs were extracted, and this was subjected to Northern blot analysis using a neomycin resistance gene as a probe according to the NorthernMax Kit method, available from Ambion.

The following were used for the Northern analysis: specifically, NorthernMax Transfer Buffer (Ambion #8672), BrightStar-Plus Transfer Membrane (Ambion #10100), blotting paper (Sigma P-6664), and ULTRAhyb (Ambion #8670). The probes were labeled with biotin using a BrightStar Psoralen-Biotin Kit (Ambion #9860G3). High Stringency Buffer (Amibion #8674); and a BrightStar BioDetect Kit (wash buffer, Ambion #8650G; blocking buffer, Ambion #8651G; streptavidin-alkaline phosphatase, Ambion #2374G; assay buffer, Ambion #8652G; and CDP-Star, Ambion #8653G).

1 μg of the total RNAs were electrophoresed on a 1% agarose gel, and then the RNAs were stained with ethidium bromide. The resulting gel was photographed and decolorized, then NorthernMax transfer buffer was used for two hours to transfer the RNAs to the transfer membrane. While the membrane was still wet, the RNAs were fixed to the transfer membrane using a UV crosslinker. The membrane was pretreated in ULTRAhyb for 30 minutes at 42° C. while being rotated in a Hybridization oven. This pretreatment solution was then discarded, and the membrane was treated by adding the biotinylated neomycin resistance gene and 10 mL of ULTRAhyb solution, and then shaking overnight at 42° C.

Figure 2:
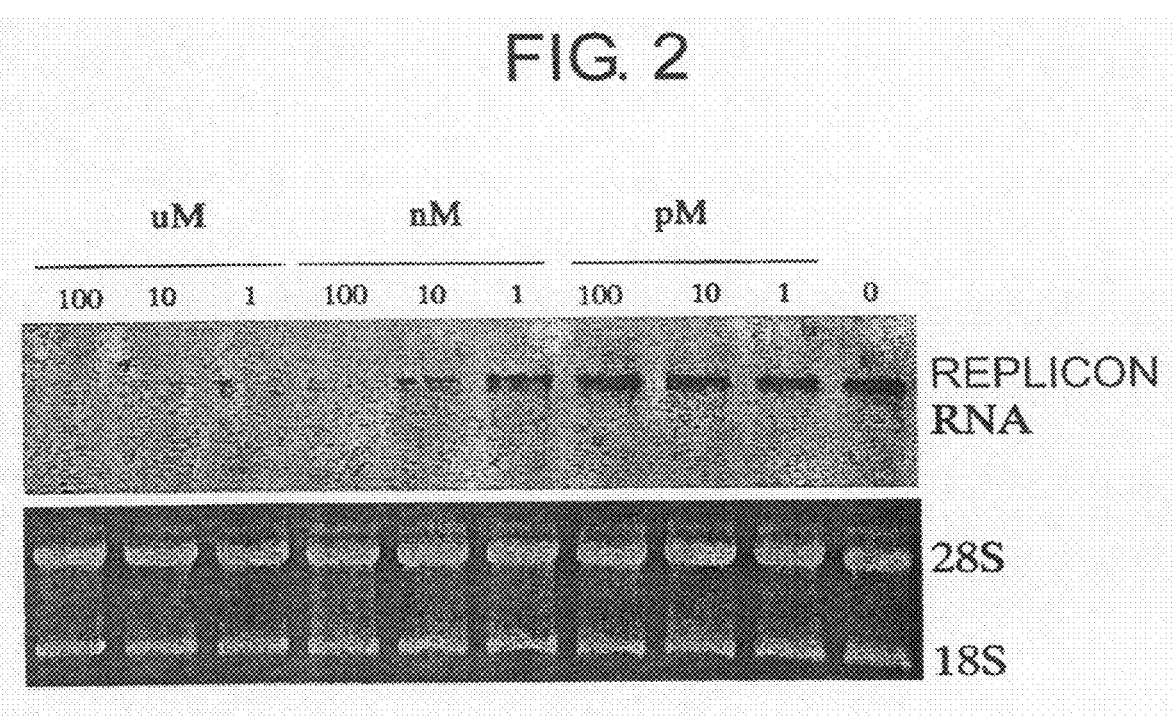
FIG. 2 shows the activity of myriocin in inhibiting HCV RNA replication, as analyzed by Northern blotting. Myriocin concentration is indicated on the horizontal axis.
Figure 3:
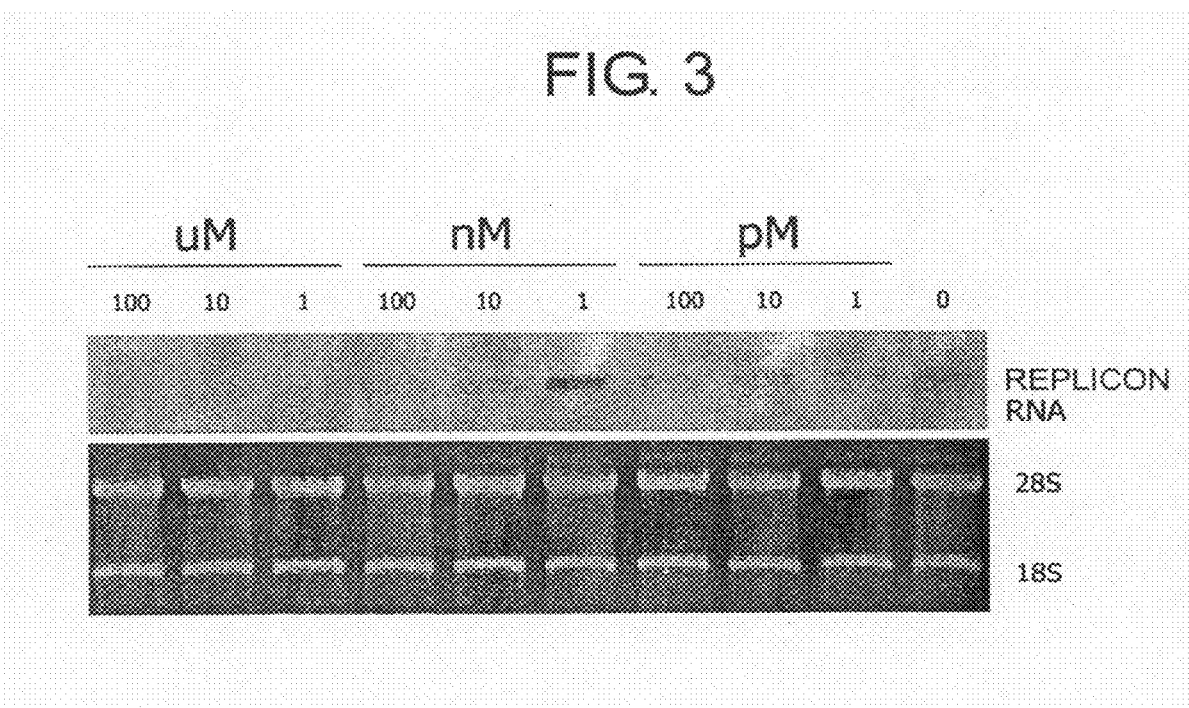
FIG. 3 shows the activity of the compound represented by formula (II) in inhibiting HCV RNA replication, as analyzed by Northern blotting. The concentration of the compound represented by formula (II) is indicated on the horizontal axis.

The ULTRAhyb solution was then discarded, and 15 mL of High Stringency Buffer pre-warmed to 42° C. was added to the membrane, and this was shaken for 30 minutes at 42° C. This same operation was then repeated once. The transfer membrane was washed using enough wash buffer to soak the membrane. The transfer membrane was shaken in a blocking buffer for 30 minutes, then this solution was discarded. 10 mL of blocking buffer supplemented with 2 μL of Streptavidin-Alkaline Phosphatase was then added, and this was shaken for 30 minutes at room temperature. The transfer membrane was shaken for 10 minutes in enough blocking buffer to soak the membrane. After washing in a wash buffer for five minutes, the transfer membrane was covered with CDP-Star, and excess solution was removed five minutes later. One hour later, the membrane was exposed to an X-ray film, and the RNA levels were compared based on the intensity of the resulting bands. As a result, at concentrations of 1 nM to 10 nM, myriocin and the compound represented by formula (II) were found to have the effect of reducing replicon RNA by 50% (FIGS. 2 and 3).

Example 2

Measurement by Western Blot Analysis of the Inhibition of HCV Protein Synthesis by Myriocin or the Compound Represented by Formula (II)

Figure 4:
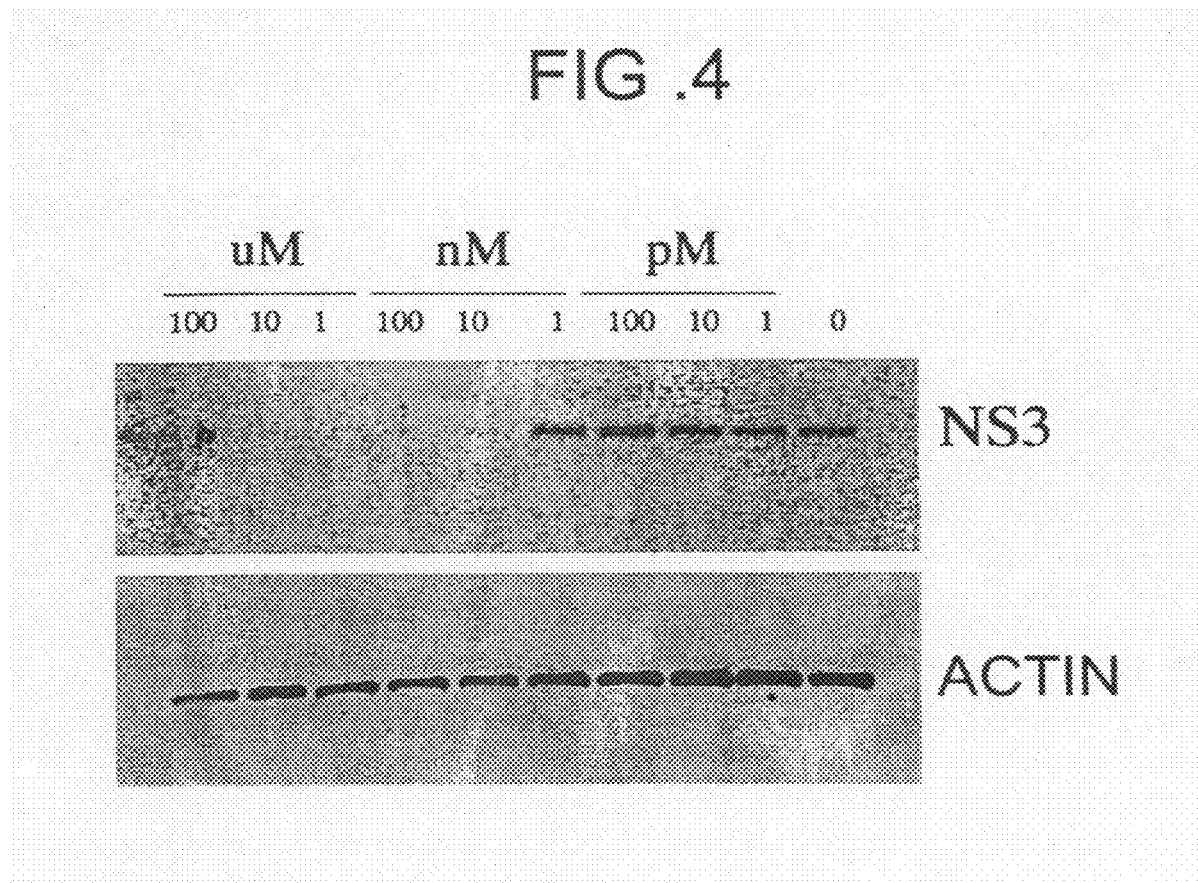
FIG. 4 shows the activity of myriocin in inhibiting HCV protein synthesis, as analyzed by Western blotting. Myriocin concentration is indicated on the horizontal axis.
Figure 5:
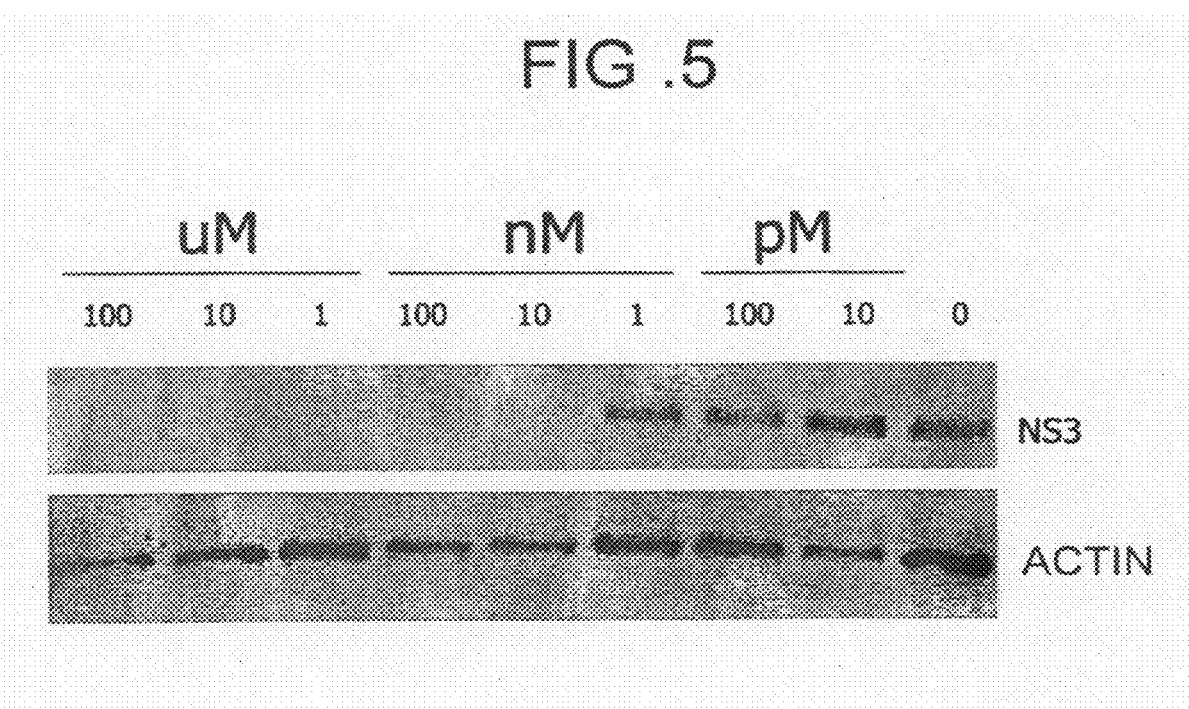
FIG. 5 shows the activity of the compound represented by formula (II) in inhibiting HCV protein synthesis, as analyzed by Western blotting. The concentration of the compound represented by formula (II) is indicated on the horizontal axis.

Western analysis was performed by the following method: Between 1 pM and 100 μM of myriocin or the compound represented by formula (II) was added to Huh-3-1 replicon cells, and the cells were cultured under 5% $CO_2$ at 37° C. After 72 hours, the culture medium was discarded, phosphate buffered saline (PBS) was added, and the cells were dislodged by pipetting and then collected by centrifugation. A lysis solution for phosphate (50 mM Tris-HCl (pH 7.5), 0.5% Triton, 3 mM EDTA, 150 mM NaCl, 12 mM glycerophosphate, 50 mM NaF, 1 mM $Na_3VO_4$, 0.5 mM PMSF, and 0.5 mM aporotinin) was added to the cells, the cells were disrupted by pipetting, and the supernatant was collected by high-speed centrifugation. A protein assay was carried out using Dye Reagent (Nacalai Tesque #074-27) (Bovine Gamma Globulin, Standard solution, BIO-RAD #500-0005). 5 μg of the obtained protein was electrophoresed on a 9-11% gradient gel (Daiichi Pure Chemicals #317552) using Tris-Glycine-SDS buffer (BIO-RAD #161-0772). Rainbow molecular weight markers (Amersham Bioscience #RPN756) were used as molecular weight size markers. The electrophoresed proteins were transferred to a membrane (PROTRAN BA85 nitrocellulose transfer membrane; Shleicher & Schuell #10401196)) using a Mini Trans-Blot Cell (BIO-RAD #170-3930). Western analysis was performed using a rabbit antibody against NS3, derived from an HCV protein. Anti-actin rabbit antibody was used as an internal standard. The results showed that at concentrations of 1 nM to 10 nM, myriocin and the compound represented by formula (II) had the effect of reducing expression of HCV proteins by 50% (FIGS. 4 and 5).

Example 3

Measurement of the Activity of Fumonisin B1 in Inhibiting the HCV Replicon

Fumonisin B1 specifically inhibits dihydrosphingosine-N-acyltransferase, which produces dihydroceramide from dihydrosphingosine midway through the process of sphingolipid biosynthesis. The activity of fumonisin B1 in inhibiting the HCV replicon was measured.

Firefly luciferase HCV replicon cells (Huh-3-1) suspended in Dulbecco's MEM (Gibco Cat. No. 10569) containing 5% fetal bovine serum (Hyclone Cat. No. SH30071.03) were plated onto a 96-well plate at 5000 cells/well, and cultured overnight under 5% $CO_2$ at 37° C. Approximately 20 hours later, fumonisin B1 was added to a final concentration of 1.37 μM to 1000 μM by carrying out a sequential three-fold dilution, and the cells were then cultured for three more days. The assay was carried out by preparing two types of assay plates: one an opaque white plate and the other a transparent plate. After culturing, the white plate was subjected to the Steady-Glo Luciferase Assay System (Promega Cat. No. E2520). More specifically, 100 μL of reagent was added to each well, mixed three to four times using a pipette, and then stood for five minutes before luminescence was measured using 1450 MicroBeta TRILUX (WALLAC). IC50 (50% inhibitory concentration) of a pharmaceutical agent was calculated by subtracting the value obtained without adding the cells as the background value from all of the values, and then defining the level of inhibition without addition of the pharmaceutical agent as 0%. A Cell Counting Kit-8 (DOJINDO Laboratories, Cat. No. 341-07761) was used for the cytotoxicity assays. 10 μL of reagent was added to each well, mixed three to four times using a pipette, and then stood for approximately 30 minutes; measurements were performed when OD450 nm reached approximately 1.0. IC50 (50% inhibitory concentration) of a pharmaceutical agent was calculated by subtracting the value obtained without adding the cells as the background value from all of the values, and then defining the level of inhibition without addition of the pharmaceutical agent as 0%.

Figure 6:
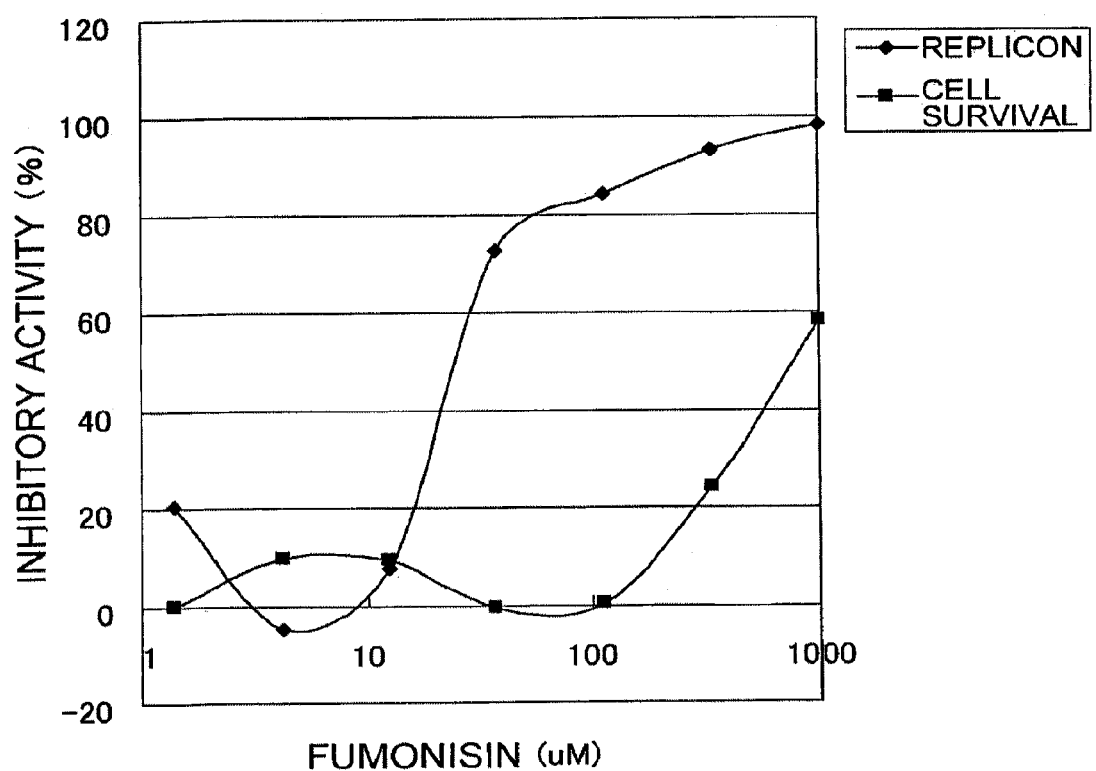
FIG. 6 shows the activity of fumonisin B1 in inhibiting the HCV replicon.

As a result, fumonisin B1 was found to show the inhibitory activity against HCV replicon at concentrations of 10 μM to 1000 μM (FIG. 6).

Example 4

Synthesis of siRNAs Against Serine Palmitoyltransferase

To confirm that inhibition of SPT inhibits HCV replicon activity, siRNAs targeting
LCB1 (a subunit of the SPT heterodimer) were synthesized. Two specific siRNAs (si246 and si633) were designed based on the sequence of LCB1 cDNA (GenBank Accession No. Y08685), and these were synthesized by Qiagen. For the control siRNA (SEQ ID NO: 3), a sequence that did not affect LCB1 expression was used. The synthesized siRNA sequences are shown in SEQ ID NO: 1 (si246) and SEQ ID NO: 2 (si633).

Example 5

Inhibition of LCB1 Protein Expression by siRNAs as Analyzed by Western Blotting $1.2 \times 10^5$ Huh-3-1 cells were plated onto a 6-well plate, and the cells were cultured overnight under 5% at 37° C. 2.3 μL of 20 μM siRNA was added to 100 μL of ECR buffer (a buffer included in the RNAiFect Kit), this was stirred vigorously, and after the addition of 4 μL of RNAiFect transfection reagent (Qiagen Cat. No. 301605) this was stirred gently at room temperature and allowed to stand for ten minutes. siRNA was added to a final concentration of 35 nM, and this was cultured for four days.

The cells were suspended in a cell lysis buffer (50 mM Tris-HCl (pH 7.5), 0.5% Triton, 3 mM EDTA, 150 mM NaCl, 12 mM glycerophosphate, 50 mM NaF, 1 mM $Na_3VO_4$, 0.5 mM PMSF, 0.5 mM aporotinin), and were allowed to stand on ice for ten minutes. This was centrifuged at 15,000×g for ten minutes, and the supernatant was collected. After quantifying the protein, the amount of protein in each sample was adjusted to 10 μg, and this was added to ¼ volume of 5×SDS sample buffer (125 mM Tris-HCl (pH 6.5), 25% Glycerol, 5% SDS, 0.25% BPB, 5% 2-Mercaptoethanol) and treated for five minutes at 98° C. After electrophoresis on polyacrylamide gel PAGmini 9/11 (Daiichi Pure Chemicals, Cat. No. 317552), the gels were blotted to a nitrocellulose membrane PROTRAN BA85 (Schleicher & Schuell Cat. No. 10404496) (70 V, three hours). Blocking of the membranes was performed using a blocking buffer (10% skim milk, 0.1% Tween 20/PBS). 1000-fold diluted anti-LCB1 antibody (Transduction Cat. No. L89820) and 250-fold diluted anti-actin (20-33) antibody (Sigma Cat. No. A5060) were added and reacted for two hours at room temperature. After washing the membranes with 0.1% Tween 20/PBS, 1000-fold diluted anti-mouse IgG-HRP (Cell Signaling Cat. No. A7076) and anti-rabbit IgG-HRP (Cell Signaling Cat. No. A7074) were each added as a secondary antibody, and reacted at room temperature for one hour. The membranes were washed with 0.1% Tween 20/PBS, and then reacted for one minute with ECL, and the resulting signals were detected by autoradiography.

As a result, both si246 and si633 were found to decrease the level of LCB1 protein expression compared with the control siRNA, as shown in FIG. 7. Particularly strong inhibition of expression was observed with si246.

Example 6

Effect of Knocking Down LCB1 on the Activity of Inhibiting the HCV Replicon

Based on the results of Example 5, the following method was used to measure the effect on cytotoxicity and HCV replicon activity under conditions in which Huh-3-1 cells show reduced LCB1 expression. More specifically, cells were plated onto a 96-well plate at 3500 cells per well, and cultured overnight under 5% $CO_2$ at 37° C. 1.75 μL of 2 μM siRNA was added to 23.3 μL of ECR buffer (buffer included in the RNAiFect Kit), this was stirred vigorously, and then 0.31 μL of RNAiFect transfection reagent was added. This was stirred gently at room temperature and then allowed to stand for ten minutes. siRNA was added to a final concentration of 35 nM, and this was cultured for four days. The effect on cytotoxicity was determined by adding 10 μL of Cell Counting Kit-8 (DOJINDO Laboratories Cat. No. 341-07761) to the medium, mixing three to four times using a pipette, and then allowing this to stand for one hour at 37° C. Absorbance was then measured at 450 nm using a microplate reader Emax (Molecular Devices). After incubation, the medium was exchanged for fresh medium, and the plate was subjected to the Steady-Glo Luciferase Assay System (Promega Cat. No. E2520). 100 μL of reagent was added to each well, mixed three to four times using a pipette, and then allowed to stand for five minutes. Luminescence was then measured using 1450 MicroBeta TRILUX (WALLAC) to determine the HCV replicon activity. IC50 (50% inhibitory concentration) of a pharmaceutical agent was calculated by subtracting the value obtained without adding the cells as the background value from all of the values, and then defining the level of inhibition without addition of the pharmaceutical agent as 0%.

Figure 8:
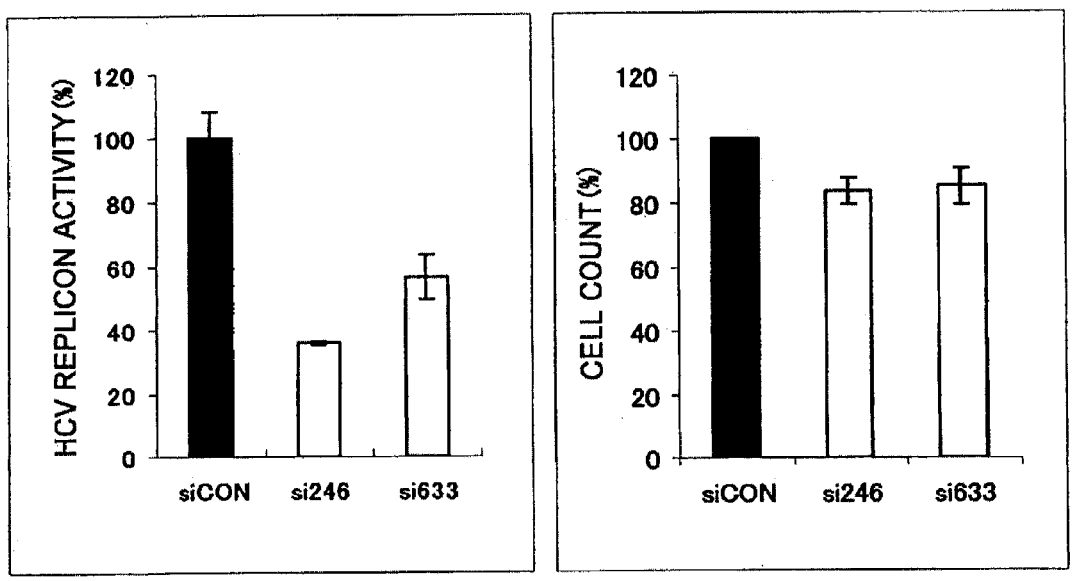
FIG. 8 shows the activity of siRNAs in inhibiting the HCV replicon and the cytotoxic effect of the siRNAs.

As a result, HCV replicon activity was significantly inhibited in si246-treated and si633-treated cells in which LCB1 expression was suppressed, as compared to that in control siRNA-treated cells, as shown in FIG. 8. A strong inhibitory effect was observed with si246, in which LCB1 expression was strongly suppressed. In addition, when the effect of siRNA treatment on cytotoxicity was examined under the same conditions, almost no effect was observed.

Example 7

HCV Replicon Assays and Cytotoxicity Tests

HCV replicon assays and cytotoxicity tests were performed on compounds represented by formula (I), and derivatives thereof.

First, to quantify the copy number of HCV-RNA, an RNA was constructed such that a firefly-derived luciferase gene was introduced into the HCV-RNA as a reporter gene. According to the method of Krieger et al. (J. Virol., 75: 4614), the luciferase gene was introduced immediately after the Internal Ribosome Entry Site (IRES) of the HCV gene, so that the gene was fused with the neomycin-resistance gene. After this RNA was synthesized in vitro, it was introduced into Huh7 cells using electroporation methods, and then isolated as G418 resistant clones. The firefly luciferase HCV replicon cells (Huh-3-1) were suspended in Dulbecco MEM (Gibco Cat. No. 10569-010) containing 5% fetal bovine serum (Hyclone Cat. No. SH 30071.03), and then plated onto a 96-well plate at 5000 cells/well, and cultured overnight under 5% $CO_2$ at 37° C. Approximately 20 hours later, diluted test compounds were added at 10 µL/well, and the cells were cultured for three more days. The assay was carried out by preparing two types of assay plates: one an opaque white plate and the other a transparent plate. After culturing, the white plate was subjected to the Steady-Glo Luciferase Assay System (Promega Cat. No. E2520). More specifically, 100 µL of a reagent was added to each well, mixed three to four times using a pipette, allowed to stand for five minutes, and then luminescence was measured using a 1450 MicroBeta TRILUX (WALLAC). IC50 (50% inhibitory concentration) of a pharmaceutical agent was calculated by subtracting the value obtained without adding the cells as the background value from all of the values, and then defining the level of inhibition without addition of the pharmaceutical agent as 0%.

A Cell Counting Kit-8 (DOJINDO Laboratories, Cat. No. 341-07761) was used for the cytotoxicity assays. More specifically, 10 µL of Cell Counting Kit-8 was added to the transparent plate, and this was warmed at 37° C. for 30 to 60 minutes. Using a 96-well plate reader, absorbance was measured at a wavelength of 450 nm with a reference wavelength of 630 nm. CC50 (50% cytotoxic concentration) of a pharmaceutical agent was calculated by subtracting the value obtained without adding the cells as the background value from all of the values, and then defining the level of cytotoxicity without addition of the test compound as 0%.

The results of the HCV replicon assays and cytotoxicity tests are shown in Tables 1 and 2.

TABLE 1

| Compound No. | Replicon assay I C50 [µM] | Cytotoxicity C C50 [µM] |
|---|---|---|
| (1) | 0.002 | >5 |
| (2) | 0.010 | >5 |
| (3) | <0.001 | >5 |
| (4) | 0.001 | >5 |
| (5) | 0.002 | >5 |
| (6) | 0.007 | >5 |
| (7) | 0.004 | >1 |
| (8) | 0.014 | >1 |
| (9) | 0.017 | >1 |
| (10) | 0.011 | >1 |
| (11) | 0.009 | >1 |
| (12) | 0.017 | >1 |
| (13) | 0.010 | >1 |
| (14) | 0.009 | >1 |
| (15) | 0.006 | >1 |
| (16) | 0.008 | >1 |
| (17) | 0.012 | >1 |
| (18) | 0.068 | >1 |
| (19) | 0.012 | >1 |
| (20) | 0.055 | >1 |
| (21) | 0.080 | >1 |
| (22) | 0.500 | >1 |
| (23) | 0.210 | >1 |
| (24) | 0.024 | >1 |
| (25) | 0.020 | >1 |
| (26) | 0.001 | >1 |
| (27) | 0.002 | >1 |

TABLE 2

| Compound No. | Replicon assay I C50 [µM] | Cytotoxicity C C50 [µM] |
|---|---|---|
| (28) | 0.001 | >1 |
| (29) | 0.003 | >1 |
| (30) | 0.001 | >1 |
| (31) | 0.005 | >1 |
| (32) | 0.800 | >5 |
| (33) | 0.250 | >1 |
| (34) | 0.003 | >1 |
| (35) | 0.004 | >1 |
| (36) | 0.004 | >1 |
| (37) | 0.017 | >1 |
| (38) | 0.024 | >1 |
| (39) | 0.002 | >1 |
| (40) | 0.002 | >5 |
| (41) | 0.128 | >1 |
| (42) | 0.076 | >1 |
| (43) | 0.103 | >1 |
| (44) | 0.082 | >1 |
| (45) | 0.007 | >1 |
| (46) | 0.002 | >5 |
| (47) | 0.005 | >5 |
| (48) | 0.020 | >5 |
| (49) | 0.245 | >50 |
| (50) | 0.262 | >5 |
| (51) | 0.072 | >5 |
| (52) | 0.1 | >50 |
| (53) | 0.020 | 22 |
| (54) | 0.020 | >50 |

Example 8

Figure 9:
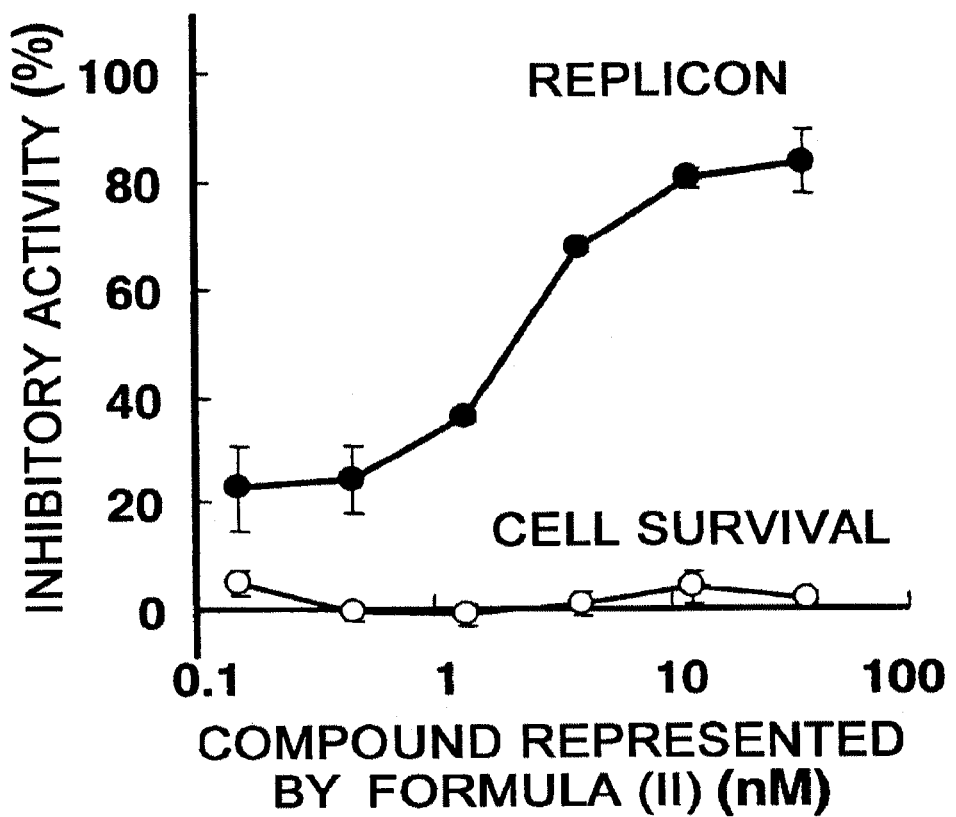
FIG. 9 shows HCV replicon inhibition and host cell toxicity caused by the compound represented by formula (II).

Inhibition of the HCV Replicon by the Compound Represented by Formula (II), and its Toxicity Towards Host Cells HCV replicon cells were treated with the compound represented by formula (II) at the concentrations indicated in FIG. 9, and the activities of inhibiting replicon replication and of inhibiting cell survival were measured. Luciferase activity of the replicon was measured using the Steady-GLO Luciferase Assay System (Promega, Cat. No. E2510), and the activity of inhibiting cell survival was measured using a Cell Counting Kit-8 (Dojindo Laboratories, Cat. No. 341-07761). As shown in FIG. 9, treatment with the compound represented by formula (II) resulted in concentration-dependent inhibitory activity against the HCV replicon (IC50=2 nM). The cytotoxicity of the compound represented by formula (II) could not be confirmed (CC50>50 nM).

Example 9

Figure 10:
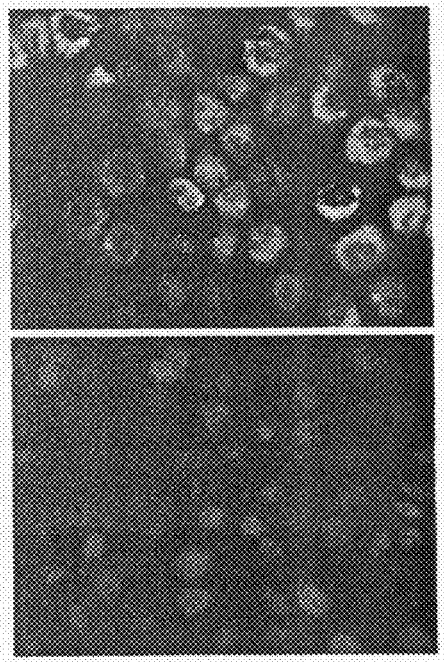
FIG. 10 shows the inhibition of HCV-NS3 protein expression by the compound represented by formula (II). Observations were made using a fluorescence microscope after immunostaining. The NS3 protein appears white, and the nuclei stained with Hoechst 33342 appear gray.

Confirmation of Inhibition of HCV-NS3 Protein Expression by the Compound Represented by Formula (II), Using an Immunostaining Method HCV replicon cells were treated with 100 nM of the compound represented by formula (II) for 96 hours, and then the cells were fixed in 3.7% formaldehyde. Blocking with 3% BSA was followed by incubation with an NS3 antibody (provided by F. Hoffman-La Roche), and then the washed cells were incubated with a Texas-Red-labeled rabbit IgG (Molecular probe), and analyzed using a fluorescence microscope (FIG. 10). The results showed that HCV-NS3 protein found to be present around the nucleus disappeared upon addition of the compound represented by formula (II), as shown in FIG. 10 (the areas that appear white indicate the NS3 protein; the

Example 10

Figure 11:
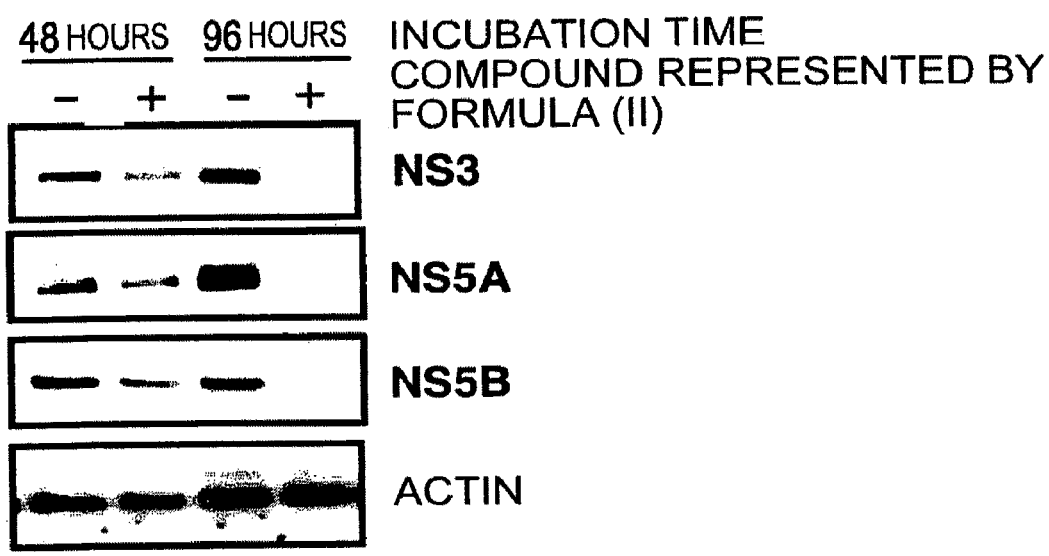
FIG. 11 shows the inhibition of expression of NS3, NS5A, and NS-5B proteins by the compound represented by formula (II). The expression of each protein was analyzed by Western blotting.

Inhibition of NS3, NS5A, and NS5B Protein Expression by the Compound Represented by Formula (II), as Analyzed by Western Blotting Replicon cells were treated with 100 nM of the compound represented by formula (II) for the lengths of time indicated in FIG. 11 (48 hours and 96 hours). Western blot analysis was performed using a method similar to that of Example 5. As a result, when the non-structural proteins of HCV, NS3, NS5A, and NS5B were detected in a time-dependent manner using their respective antibodies, the expression levels of the virus proteins were found to be reduced (FIG. 11).

Example 11

SPT Inhibitory Activity of the Compound Represented by Formula (II)

Figure 12:
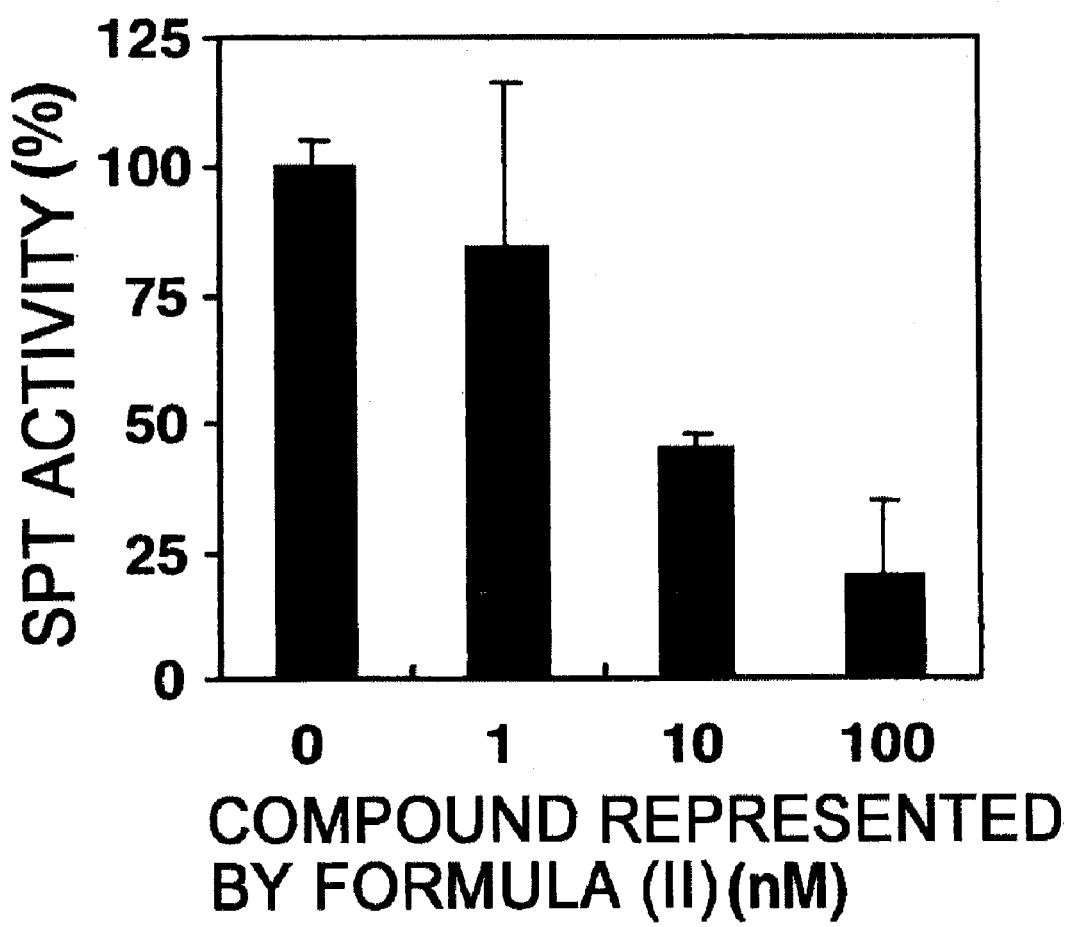
FIG. 12 shows the activity of the compound represented by formula (II) in inhibiting SPT.

Human recombinant SPT (a heterodimer of LCB1 and LCB2) protein was prepared to measure in vitro SPT inhibitory activity. The cDNAs of LCB1 and LCB2 were obtained by RT-PCR from a human liver cDNA library (Clontech, Cat. No. 639307), and incorporated into a His-tagged pBudCE4.1 vector (Invitrogen, Cat. No. V532-20). Gene transfer was carried out on HEK293 cells (ATCC, Cat. No. CRL-1573), the cells were lysed 72 hours later, and the proteins were purified on Ni-NTA agarose (Qiagen, Cat. No. 1018244). SPT activity was determined by adding the purified SPT to a reaction buffer (200 mM HEPES buffer (pH 8.0), 5 mM EDTA, 10 mM DTT, 0.05 mM pyridoxal 5-phosphate, 0.2 mM palmitoyl-CoA, 0.1 mM L-serine, and 1 mCi [3H]serine (Amersham, Cat. No. TRK308)), and reacting it for 15 minutes at 37° C. After extraction with chloroform/methanol (1:2, v/v), the organic layer was extracted twice with water, and then the radioactivity of the organic layer was measured using a liquid scintillation counter. The results showed that the compound represented by formula (II) has the SPT inhibitory activity with an IC50 of about 10 nM, as shown in FIG. 12.

Example 12

Inhibition of the De Novo Syntheses of Ceramide and Sphingomyelin by the Compound Represented by Formula (II)

Figure 13:
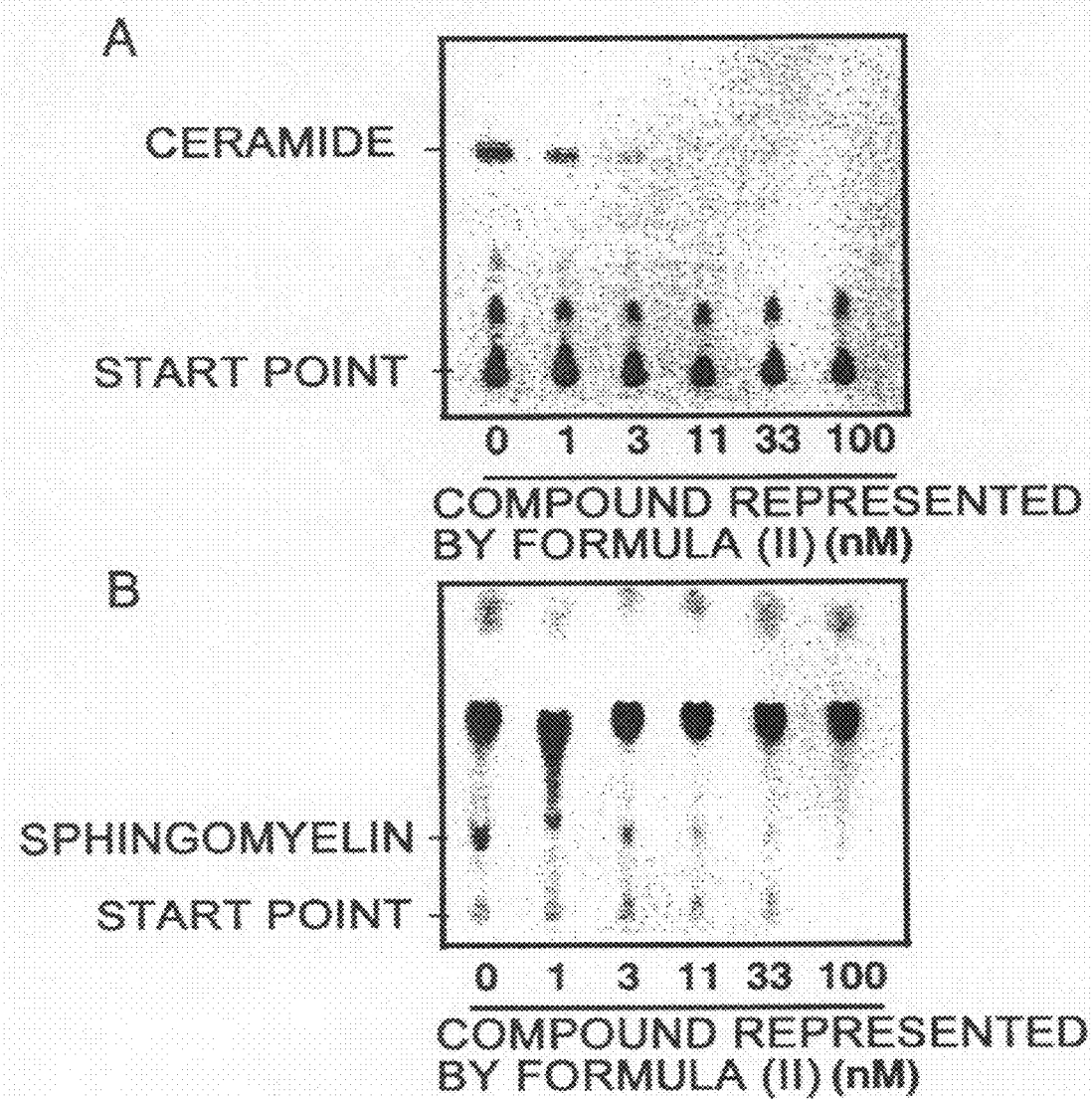
FIG. 13 shows the inhibition of the de novo syntheses of ceramide and sphingomyelin by the compound represented by formula (II).

HCV replicon cells were treated for 48 hours with the compound represented by formula (II) at the concentrations indicated in FIG. 13. The cells were then labeled for three hours with [14C]serine. After extraction with chloroform/methanol (1:2, v/v), de novo synthesized ceramide (FIG. 13A) and sphingomyelin (FIG. 13B) were separated by thin layer chromatography. The results showed that intracellular de novo syntheses of ceramide and sphingomyelin were inhibited by the compound represented by formula (II) in a concentration dependent manner, as shown in FIG. 13.

Example 13

Figure 14:
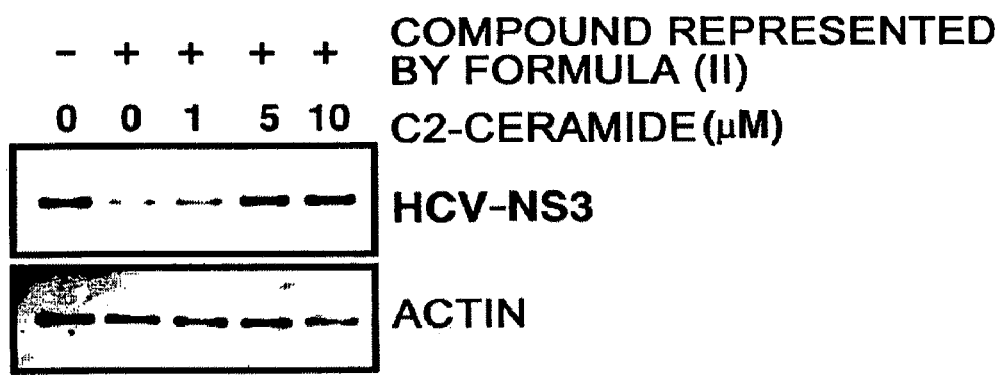
FIG. 14 shows the C2-ceramide-induced suppression of the inhibition of HCV replication by the compound represented by formula (II).

Recovery from Replication Inhibition Due to the Compound Represented by Formula (II), by the Action of C2-Ceramide To elucidate whether the inhibitory activity of the compound represented by formula (II) against the HCV replicon is dependent on the sphingolipid biosynthetic pathway, cell-permeable ceramide, C2-ceramide (Sigma, Cat. No. A7191), was added to HCV replicon cells at the same time as the compound represented by formula (II), and these were cultured for 96 hours. These cell extracts were used to perform Western blot analysis using a method similar to that of Example 5. The results showed that inhibition of HCV replication by the compound represented by formula (II) was suppressed in a manner dependent on C2-ceramide concentration (FIG. 14).

Example 14

Figure 15:
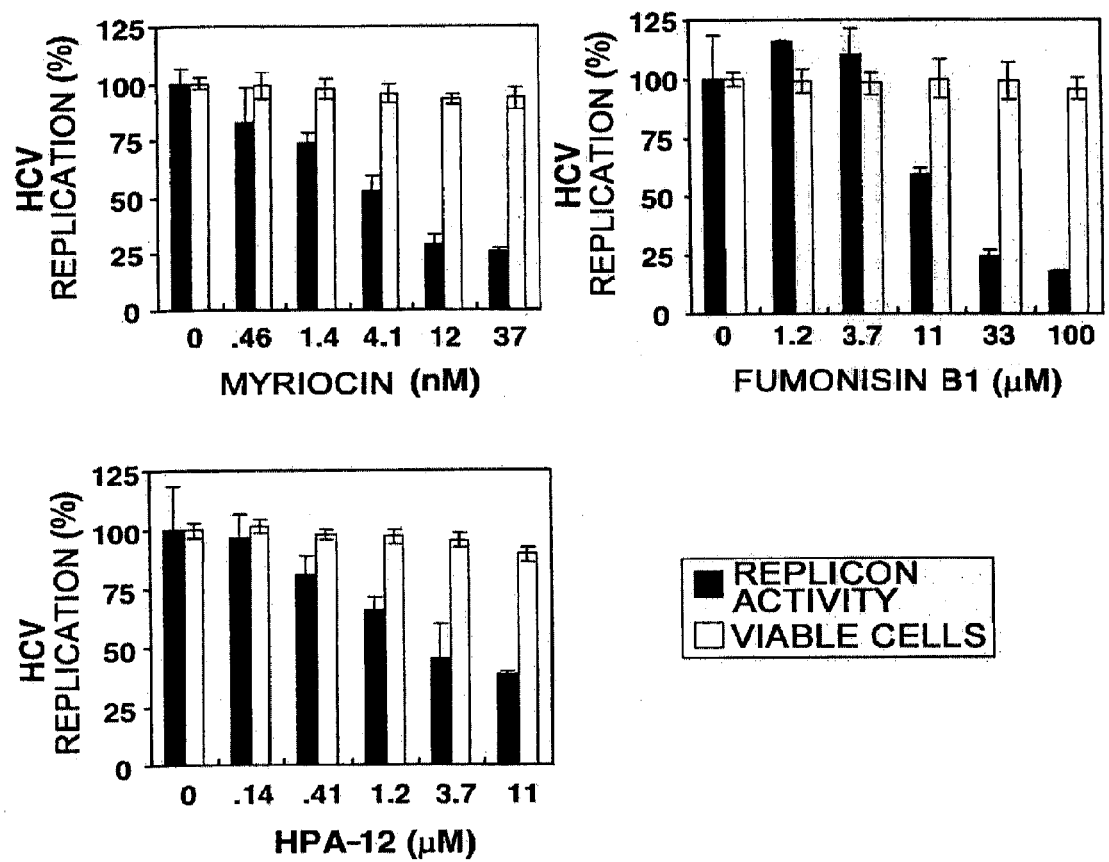
FIG. 15 shows the inhibition of HCV replication by the low-molecular-weight compounds related to raft biosynthesis.

Inhibition of HCV Replication by Low-Molecular-Weight Compounds Related to Raft Biosynthesis HCV replicon cells were treated with a known SPT inhibitor myriocin (Sigma, Cat. No. M1177), ceramide synthesis inhibitor fumonisin B1 (Sigma, Cat. No. F1147), and ceramide trafficking inhibitor HPA-12 (synthesized according to the synthetic method of Kobayashi et al., Org. lett. (2002)), and then replicon activity and viable cell count were measured 72 hours later. The results confirmed that all of these compounds have the effect of suppressing the HCV replication at non-cytotoxic concentrations (FIG. 15).

Example 15

Effect of the Compound Represented by Formula (II) on Raft Proteins (1)

Figure 16:
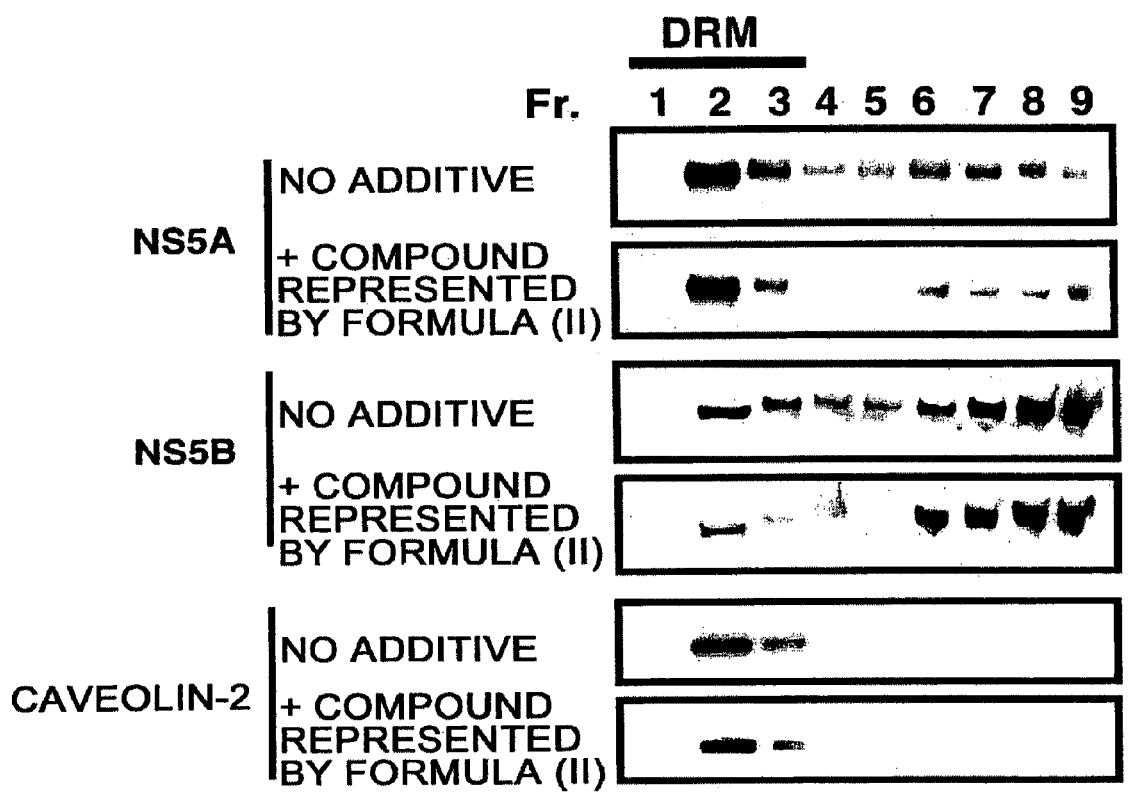
FIG. 16 shows the effect of the compound represented by formula (II) on raft proteins.

1 mM of the compound represented by formula (II) was added to the HCV replicon cells, then 72 hours later the cell extract was treated for one hour with a solubilizer, 1% Nonidet P-40 (Nacalai tesque, Cat. No. 252-23). Fractions 1 to 9 were separated by the sucrose density gradient fractionation method, and Western blot analysis was performed using a method similar to that of Example 5. The results showed the compound represented by formula (II) reduced the expression level of NS5B in the solubilizer-resistant fraction, as shown in FIG. 16. However, the effect of the compound represented by formula (II) on NS5A and the host's raft-associated protein caveolin-2 could not be confirmed. Caveolin-2 expression was confirmed using a caveolin-2 antibody (BD Transduction, Cat. No 610684).

Example 16

Effect of the Compound Represented by Formula (II) on Raft Proteins (2)

Figure 17:
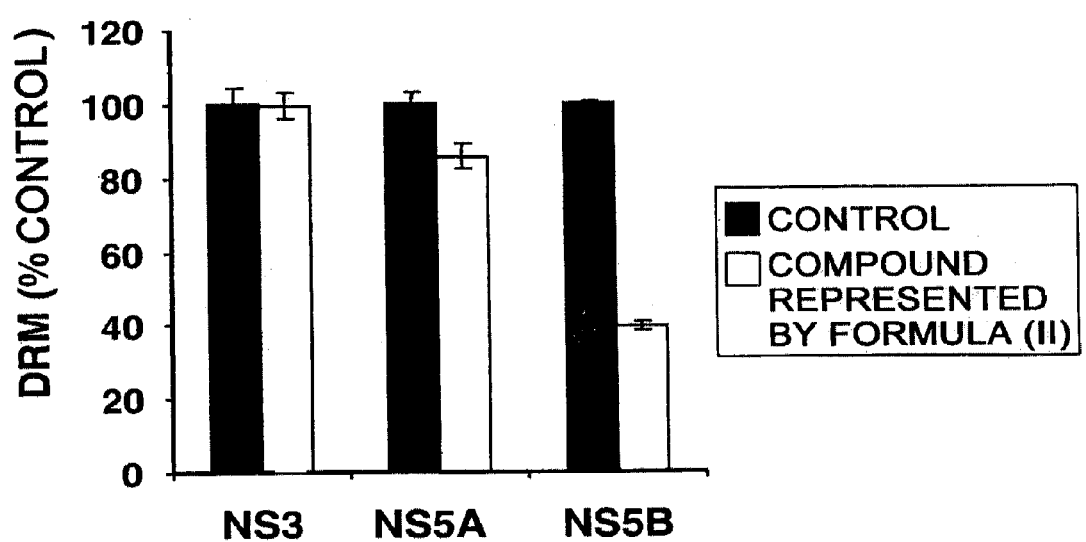
FIG. 17 shows the effect of the compound represented by formula (II) on raft proteins.

1 µM of the compound represented by formula (II) was added to the HCV replicon cells, then 72 hours later the cell extract was treated for one hour with 1% NP-40. Raft proteins (solubilizer-resistant) and non-raft proteins were separated using the sucrose density gradient fractionation method, diluted with PBS, concentrated, and then quantified by ELISA analysis. The results showed the compound represented by formula (II) caused significant dissociation of NS5B from the raft (FIG. 17).

INDUSTRIAL APPLICABILITY

The present invention showed that sphingolipid biosynthesis is involved in HCV infection, and that compounds that inhibit the activity or expression of enzymes involved in sphingolipid biosynthesis may become very useful therapeutic agents or preventive agents for HCV infections. Further, since sphingomyelin, a sphingolipid, is a component of rafts on cell membranes, and since viruses such as influenza virus and HIV replicate via rafts (Takeda M. et al. (2003) PNAS, 100, 25; Lucero H. A., et al. (2004) Archives of Biochemistry and Biophysics, 426, 208; Simons K. (1997) Nature, 387, 569; G.-Z. Leu et al. (2004)), HCV was strongly suggested to replicate via rafts. Therefore, pharmaceutical agents that comprise as active ingredients a compound of the present invention that targets rafts may be used as pharmaceutical agents for preventing or treating HCV infections.

Since the cascades targeted in vivo by conventional pharmaceutical agents for preventing or treating HCV infections have so far been unclear, side effects have been of some concern; however, the pharmaceutical agents of the present invention have a more specific target, and this is thought to allow simple elimination of side effects, regulation of the effects of the pharmaceutical agents, and so on.

The pharmaceutical agents of the present invention may be used not only as pharmaceutical agents for preventing or treating HCV infections, but also as pharmaceutical agents useful for preventing or treating diseases induced by abnormalities in sphingolipid synthesis; for example, sphingolipidosis, which is a disease that shows abnormal accumulation of lipids (sphingomyelin), Alzheimer's disease, which involves β-amyloid proteins with a sphingolipid binding motif; HIV infection, which involves gp120 proteins; prion diseases, which involves PrP proteins; amyotrophic lateral sclerosis, which causes nerve cell death upon an increase of ceramide in the spinal motor neurons (Cutler, R. G., et al., Ann. Neurol., 52, 448-457, 2002), and infection by viruses that infect host cells by binding to rafts (for example, influenza virus and HIV).

The invention claimed is:

1. A method of screening for a pharmaceutical agent for treating a hepatitis C virus (HCV) infection, wherein the method comprises:
   (a) contacting a cell with a test compound;
   (b) measuring the amount of a product synthesized in the process of sphingomyelin biosynthesis from palmitoyl CoA in the cell in the presence of the test compound;
   (c) selecting a test compound that reduces the amount of the product synthesized in the presence of the test compound in (b), as compared to a measured amount of the product synthesized when the test compound is absent; and
   (d) assaying whether the test compound selected in (c) has inhibitory activity against HCV replication.

2. The screening method of claim 1, wherein the assaying in (d) comprises detection of HCV RNA in a cell contacted with the test compound selected in (c).

3. The screening method of claim 1, wherein the assaying in (d) comprises detection of HCV protein expression in a cell contacted with the test compound selected in (c).

4. The screening method of claim 1, wherein the product synthesized in the process of sphingomyelin biosynthesis is sphingomyelin.

5. The screening method of claim 1, further comprising (e) preparing a pharmaceutical agent for treating a HCV infection, wherein the pharmaceutical agent comprises the test compound assayed in (d), the test compound having been shown in (d) to have inhibitory activity against HCV replication.

6. A method of screening for a pharmaceutical agent for treating a HCV infection, wherein the method comprises:
   (a) contacting a cell with a test compound;
   (b) measuring the amount of 3-ketodihydrosphingosine, dihydrosphingosine, dihydroceramide, or ceramide synthesized in the cell in the presence of the test compound;
   (c) selecting a test compound that reduces the amount of 3-ketodihydrosphingosine, dihydrosphingosine, dihydroceramide, or ceramide synthesized in the presence of the test compound in (b), as compared to a measured amount of 3-ketodihydrosphingosine, dihydrosphingosine, dihydroceramide, or ceramide, respectively, synthesized when the test compound is absent; and
   (d) assaying whether the test compound selected in (c) has inhibitory activity against HCV replication.

7. The screening method of claim 6, wherein the assaying in (d) comprises detection of HCV RNA in a cell contacted with the test compound selected in (c).

8. The screening method of claim 6, wherein the assaying in (d) comprises detection of HCV protein expression in a cell contacted with the test compound selected in (c).

9. The screening method of claim 6, further comprising (e) preparing a pharmaceutical agent for treating a HCV infection, wherein the pharmaceutical agent comprises the test compound assayed in (d), the test compound having been shown in (d) to have inhibitory activity against HCV replication.

10. A method of screening for a pharmaceutical agent for treating a HCV infection, wherein the method comprises:
    (a) providing an enzyme in the palmitoyl CoA to sphingomyelin biosynthetic pathway;
    (b) contacting the enzyme with a test compound and a substrate of the enzyme;
    (c) measuring the amount of a product synthesized by the enzyme over time in the presence of the test compound;
    (d) determining that the test compound reduces the amount of the product synthesized by the enzyme over time in the presence of the test compound in (c), as compared to a measured amount of the product synthesized by the enzyme when the test compound is absent; and (e) assaying whether the test compound has inhibitory activity against HCV replication.

11. The screening method of claim 10, wherein the enzyme is present in a cell extract.

12. The screening method of claim 10, wherein the enzyme is present in a purified state.

13. The screening method of claim 10, wherein the assaying in (e) comprises detection of HCV RNA in a cell contacted with the test compound.

14. The screening method of claim 10, wherein the assaying in (e) comprises detection of HCV protein expression in a cell contacted with the test compound.

15. The screening method of claim 10, further comprising (f) preparing a pharmaceutical agent for treating a HCV infection, wherein the pharmaceutical agent comprises the test compound assayed in (e), the test compound having been shown in (e) to have inhibitory activity against HCV replication.

16. A method of screening for a pharmaceutical agent for treating a HCV infection, wherein the method comprises:
(a) contacting an enzyme in the palmitoyl CoA to sphingomyelin biosynthetic pathway with a test compound and a substrate of the enzyme;
(b) measuring the activity of the enzyme;
(c) selecting a test compound that reduces the activity of the enzyme in the presence of the test compound in (b), as compared to a measured activity of the enzyme when the test compound is absent; and
(d) assaying whether the test compound selected in (c) has inhibitory activity against HCV replication.

17. The screening method of claim 16, wherein the enzyme is present in a cell extract.

18. The screening method of claim 16, wherein the enzyme is present in a purified state.

19. The screening method of claim 16, wherein the assaying in (d) comprises detection of HCV RNA in a cell contacted with the test compound selected in (c).

20. The screening method of claim 16, wherein the assaying in (d) comprises detection of HCV protein expression in a cell contacted with the test compound selected in (c).

21. The screening method of claim 16, further comprising (e) preparing a pharmaceutical agent for treating a HCV infection, wherein the pharmaceutical agent comprises the test compound assayed in (d), the test compound having been shown in (d) to have inhibitory activity against HCV replication.

22. A method of screening for a pharmaceutical agent for treating a HCV infection, wherein the method comprises:
(a) contacting an enzyme in the palmitoyl CoA to sphingomyelin biosynthetic pathway with a test compound and a substrate of the enzyme;
(b) measuring the activity of the enzyme;
(c) selecting a test compound that reduces the activity of the enzyme in the presence of the test compound in (b), as compared to a measured activity of the enzyme when the test compound is absent; and
(d) providing a pharmaceutical agent for treating a HCV infection, the pharmaceutical agent comprising the selected test compound.

23. The screening method of claim 22, wherein the enzyme is present in a cell extract.

24. The screening method of claim 22, wherein the enzyme is present in a purified state.

25. A method of screening for a pharmaceutical agent for treating a HCV infection, wherein the method comprises:
(a) contacting a cell with a test compound;
(b) measuring the amount of a product synthesized in the process of sphingomyelin biosynthesis from palmitoyl CoA in the cell in the presence of the test compound;
(c) selecting a test compound that reduces the amount of the product synthesized in the presence of the test compound in (b), as compared to a measured amount of the product synthesized when the test compound is absent; and
(d) providing a pharmaceutical agent for treating a HCV infection, the pharmaceutical agent comprising the selected test compound.

26. A method of screening for a pharmaceutical agent for treating a HCV infection, wherein the method comprises:
(a) contacting a cell with a test compound;
(b) measuring the amount of 3-ketodihydrosphingosine, dihydrosphingosine, dihydroceramide, or ceramide, respectively, synthesized in the cell in the presence of the test compound;
(c) selecting a test compound that reduces the amount of 3-ketodihydrosphingosine, dihydrosphingosine, dihydroceramide, or ceramide synthesized in the presence of the test compound in (b), as compared to a measured amount of 3-ketodihydrosphingosine, dihydrosphingosine, dihydroceramide, or ceramide, respectively, synthesized when the test compound is absent; and
(d) providing a pharmaceutical agent for treating a HCV infection, the pharmaceutical agent comprising the selected test compound.

27. A method of screening for a pharmaceutical agent for treating a HCV infection, wherein the method comprises:
(a) providing an enzyme in the palmitoyl CoA to sphingomyelin biosynthetic pathway;
(b) contacting the enzyme with a test compound and a substrate of the enzyme;
(c) measuring the amount of a product synthesized by the enzyme over time in the presence of the test compound;
(d) selecting a test compound that reduces the amount of the product synthesized by the enzyme over time in the presence of the test compound in (c), as compared to a measured amount of the product synthesized by the enzyme when the test compound is absent; and
(e) providing a pharmaceutical agent for treating a HCV infection, the pharmaceutical agent comprising the selected test compound.

28. The screening method of claim 27, wherein the enzyme is present in a cell extract.

29. The screening method of claim 27, wherein the enzyme is present in a purified state.

* * * * *